United States Patent [19]
Bumol et al.

[11] Patent Number: 5,348,887
[45] Date of Patent: Sep. 20, 1994

[54] VECTORS AND DNAS FOR EXPRESSION OF A HUMAN ADENOCARCINOMA ANTIGEN

[75] Inventors: Thomas F. Bumol, Carmel; Robert A. Gadski; Amy E. Hamilton, both of Indianapolis, all of Ind.; J. Richard Sportsman, Palo Alto, Calif.; Joann Strnad, Yardley, Pa.

[73] Assignee: Eli Lilly and Company, Indianapolis, Ind.

[21] Appl. No.: 976,301

[22] Filed: Nov. 13, 1992

Related U.S. Application Data

[63] Continuation of Ser. No. 184,569, Apr. 21, 1988, abandoned which is a continuation-in-part of Ser. No. 150,252, Jan. 29, 1988 abandoned.

[51] Int. Cl.$^5$ .................... C12N 15/12; C12N 15/70
[52] U.S. Cl. .................. 435/320.1; 435/69.3; 435/172.3; 435/240.1; 435/252.3; 435/252.33; 536/23.5
[58] Field of Search ............... 435/69.3, 172.3, 320.1, 435/225.3, 252.33, 240.1; 536/23.5

[56] References Cited

PUBLICATIONS

Sportsman et al. Biotechnol. Appl. Biochem. 10:536–544 (1988).
Strnad et al. Cancer Research 49:314–317 (1989).
Milstein, Ouervian: Monoclonal Antibodies. In: "Handbook of Experimental Immunology", 4th Ed., Blackwall Scientific Publications, Inc. CA (1986), Title Page.
Young et al. 1987 Efficient Isolation of Genes by Using Antibody Probes. Proc. Natl. Acad. Sci. USA, 80:1194.
Pouwells et al *Cloning Vectors* (1985), pp. I–B–i–8, VIII–B–6–i–6.
Promega Catalogue 1987/1988. Section 2, pp. 4 and 9.
Shortle et al., *Ann Rev. Genet.* 1981 15 288–94.
Zimmerman et al., 1987, *PNAS* 84:2960–2964.
Rose et al., 1986, *PNAS* 83:1261–1265.
Varki et al., 1984, *Cancer Research* 44:681–687.

*Primary Examiner*—Richard A. Schwartz
*Assistant Examiner*—J. LeGuyader
*Attorney, Agent, or Firm*—Ronald S. Maciak; Douglas K. Norman; Gerald V. Dahling

[57] ABSTRACT

The present invention comprises novel recombinant DNA compounds which encode the ~40,000 dalton adenocarcinoma antigen recognized by monoclonal antibody KS 1/4. Eukaryotic and prokaryotic expression vectors have been constructed that comprise novel KSA-encoding DNA and drive expression of KSA when transformed into an appropriate host cell. The novel expression vectors can be used to produce KSA derivatives, such as non-glycosylated KSA, and to produce KSA precursors, such as nascent KSA, and to produce subfragments of KSA. The recombinant-produced KSA is useful for the diagnosis, prognosis and treatment of disease states including adenocarcinomas of the lung, prostate, breast, ovary and colon/rectum; and for the creation of novel antibodies for treatment or diagnosis of the above.

27 Claims, 21 Drawing Sheets

VECTORS AND DNAS FOR EXPRESSION OF A HUMAN ADENOCARCINOMA ANTIGEN

CROSS REFERENCE

This application is a continuation of application Ser. No. 7/184,569, filed on Apr. 21, 1988, now abandoned, which is a continuation-in-part of U.S. application Ser. No. 07/150,252 filed Jan. 29, 1988, now abandoned.

SUMMARY OF THE INVENTION

The present invention provides novel DNA compounds and recombinant DNA cloning vectors that encode the ~40,000 dalton cell surface glycoprotein antigen of UCLA-P3 cells which is recognized by the monoclonal antibody KS 1/4. The vectors allow expression of the novel DNA compounds in either eukaryotic or prokaryotic host cells. The present invention also provides host cells transformed with these novel cloning vectors. The transformed host cells express the KS 1/4 antigen or precursors, derivatives, or subfragments thereof. Many of the present DNA compounds can be used to produce KS 1/4 antigen derivatives never before synthesized either in nature or in the laboratory, and the present invention also comprises these unique proteins.

Lung cancer, the leading cause of cancer death, is divided into four major histological types, large-cell undifferentiated (15%), small-Cell (20%), epidermoid or squamous (30%), and adenocarcinoma (35%). The most effective forms of therapy are radiation treatment and surgery, yet fewer than 30% of all lung cancer patients have tumors which can be totally resected at diagnosis. Unfortunately, even after apparent complete removal of the tumor, fewer than one-third of these patients survive beyond five years. It is therefore important to develop methods for early diagnosis and more effective treatment of this disease.

In recent years, immunological techniques have been utilized to manipulate the immune response of lung cancer patients. These techniques provide an alternative method for diagnosis, prognosis and therapy. Antibodies raised against specific lung cancer cell surface antigens are instrumental for an immunological regimen of diagnosis and therapy, because antibodies to such cell surface structures potentially recognize targets more specifically. The use of monoclonal antibodies (MoAbs) raised against such antigens for site directed therapy is now under intense worldwide clinical evaluation. To facilitate protein engineering and the production of specific monoclonal antibodies, it is advantageous to know the detailed amino acid structure of the target antigen. Thus, the cloning of the KS 1/4 reactive antigen provides the essential information needed to design novel antibodies.

The KS 1/4 antigen (KSA) is an approximately 40,000 dalton cell surface glycoprotein antigen that is found in high epitope density in virtually all human adenocarcinomas (lung, prostate, breast and colon) examined to date and also in some corresponding human epithelial tissues. This antigen, as expressed in UCLA-P3 cells, is specifically recognized by monoclonal antibody KS 1/4, as described by Varki et al., (1984) Cancer Research 44:681-687. The KSA is synthesized as a 314 amino acid residue preproprotein of 34,922 daltons. This preprotein is then processed to a 233 amino acid residue cell surface protein of 26,340 daltons. The discrepancy between this figure and the observed weight of ~40,000 daltons is accounted for by the post-translational modification (glycosylation) of the nascent protein. The maturation of the cell surface KSA is believed to include the cleavage of a signal peptide of ~21 amino acid residues (residues 1-21 of preproKSA), then removal of a propeptide of ~60 amino acid residues (residues 22-81 of preproKSA).

The KSA shows structural features which are common to membrane proteins such as a cysteine-rich domain, N-glycosylation sites, a hydrophobic transmembrane domain, and a highly charged cytoplasmic anchorage domain. It is assumed that the cytoplasmic anchorage domain comprises the ~26 amino acid residues found at the carboxy terminus of the nascent protein (residues 289-314 of preproKSA), while the transmembrane region comprises the ~23 amino acid residues immediately preceding the cytoplasmic anchorage domain (residues 266-288 of preproKSA). The remainder of the amino acid residues comprise the extracellular KSA itself, which, when expressed in certain cells, is glycosylated and folded into a conformation which is recognized by monoclonal antibody KS 1/4. Since prokaryotes usually do not glycosylate or properly fold proteins expressed from recombinant genes, the present invention is significant in that it allows for the first time the synthesis of KSA derivatives which have not undergone the post-translational modifications of normal KSA. These unique derivatives have enormous research and clinical value, as discussed more fully below.

For purposes of the present invention, as disclosed and claimed herein, the following terms are as defined below.

Ag—an antigen.

$Ap^R$—the ampicillin-resistant phenotype or gene conferring same.

dhfr—the dihydrofolate reductase phenotype or gene conferring same.

Enh—an enhancer sequence obtained from the BK virus.

$G418^R$—the G418-resistant phenotype or gene conferring same. May also be identified as $Km^R$.

$Hm^R$—the hygromycin-resitant phenotype or gene conferring same.

IVS—DNA encoding an intron, also called an intervening sequence.

KSA—the cloned ~40,000 dalton cell surface glycoprotein antigen of UCLA-P3 cells that is recognized by monoclonal antibody KS 1/4 or any antigenic fragment thereof, regardless of whether said fragment is recognized by KS 1/4.

LP—a DNA segment comprising the promoter activity of the adenovirus late promoter.

MoAB—monoclonal antibody.

Nascent protein—the polypeptide produced upon translation of a mRNA transcript, prior to any post-translational modifications.

pA—a DNA sequence encoding a polyadenylation signal.

pL—a DNA segment comprising the promoter activity of the bacteriophage A leftward promoter.

prepro-KSA—KSA with a prepropeptide attached to the amino terminus.

pro-KSA—KSA with a propeptide attached to the amino terminus.

Promoter—a DNA sequence that directs transcription of DNA into RNA.

Recombinant DNA Cloning Vector—any autonomously replicating agent, including, but not limited to, plasmids and phages, comprising a DNA molecule to which one or more additional DNA segments can be or have been added.

Recombinant DNA Expression Vector—any recombinant DNA cloning vector into which a promoter has been incorporated.

Replicon—A DNA sequence that controls and allows for autonomous replication of a plasmid or other vector.

Restriction Fragment—any linear DNA sequence generated by the action of one or more restriction endonuclease enzymes.

Sensitive Host Cell—a host cell that cannot grow in the presence of a given antibiotic or other toxic compound without a DNA segment that confers resistance thereto.

Structural Gene—any DNA sequence that encodes a functional polypeptide, inclusive of translational start and stop signals.

$Tc^R$—the tetracycline-resistant phenotype or gene conferring same.

Transformation—the introduction of DNA into a recipient host cell that changes the genotype of the recipient cell.

Transformant—a recipient host cell that has undergone transformation.

Translational Activating Sequence—any DNA sequence, inclusive of that encoding a ribosome binding site and translational start codon, such as 5'-ATG-3', that provides for the translation of a mRNA transcript into a peptide or polypeptide.

DETAILED DESCRIPTION OF THE INVENTION

Figure 1:
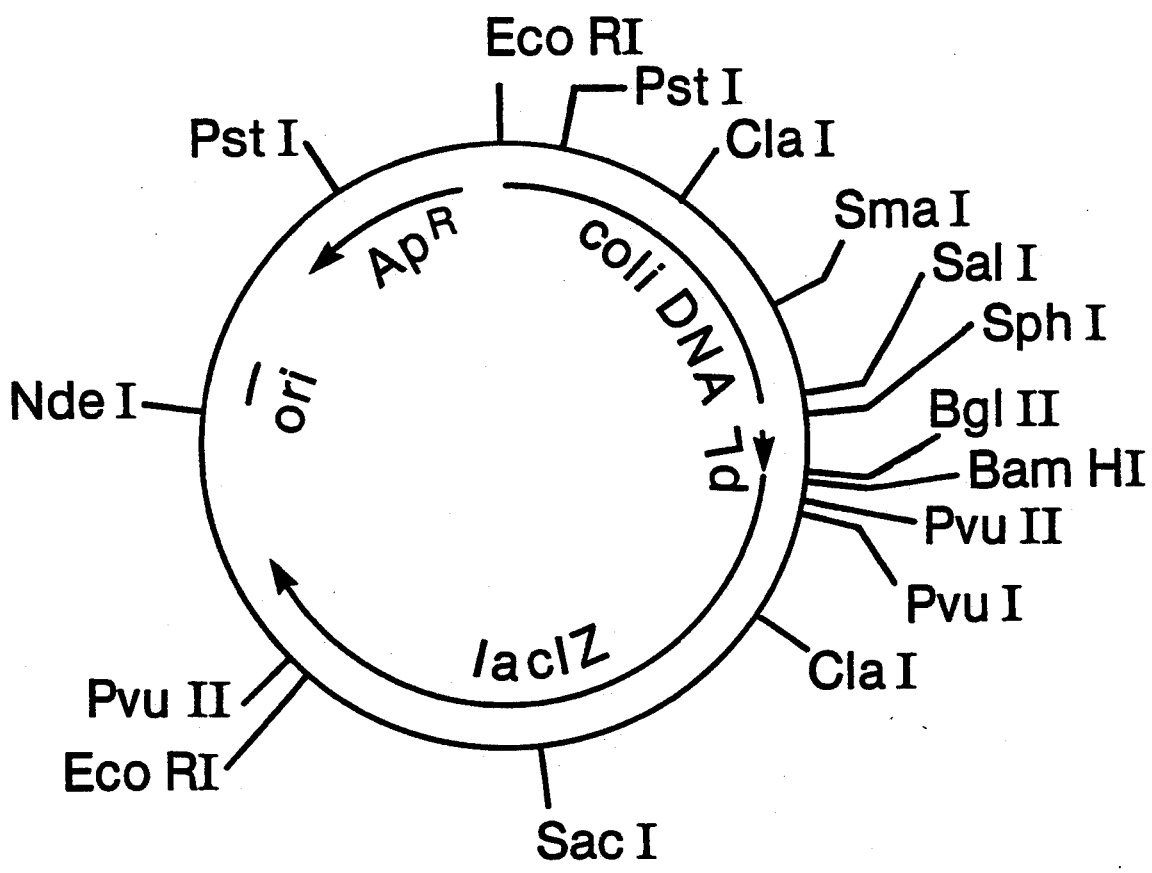
FIG. 1—the restriction site and function map of plasmid pKC283. For the purpose of this disclosure, the figures are not drawn exactly to scale.

The present invention is a recombinant DNA compound which comprises DNA encoding a protein with the amino acid residue sequence:

```
ALA LYS PRO GLU GLY ALA LEU GLN ASN ASN ASP GLY LEU TYR ASP PRO
ASP CYS ASP GLU SER GLY LEU PHE LYS ALA LYS GLN CYS ASN GLY THR
SER THR CYS TRP CYS VAL ASN THR ALA GLY VAL ARG ARG THR ASP LYS
ASP THR GLU ILE THR CYS SER GLU ARG VAL ARG THR TYR TRP ILE ILE
ILE GLU LEU LYS HIS LYS ALA ARG GLU LYS PRO TYR ASP SER LYS SER
LEU ARG THR ALA LEU GLN LYS GLU ILE THR THR ARG TYR GLN LEU ASP
PRO LYS PHE ILE THR SER ILE LEU TYR GLU ASN ASN VAL ILE THR ILE
ASP LEU VAL GLN ASN SER SER GLN LYS THR GLN ASN ASP VAL ASP ILE
ALA ASP VAL ALA TYR TYR PHE GLU LYS ASP VAL LYS GLY GLU SER LEU
PHE HIS SER LYS LYS MET ASP LEU THR VAL ASN GLY GLU GLN LEU ASP
LEU ASP PRO GLY GLN THR LEU ILE TYR TYR VAL ASP GLU LYS ALA PRO
GLU PHE SER MET GLN GLY LEU LYS ALA GLY VAL ILE ALA VAL ILE VAL
VAL VAL VAL MET ALA VAL VAL ALA GLY ILE VAL VAL LEU VAL ILE SER
ARG LYS LYS ARG MET ALA LYS TYR GLU LYS ALA GLU ILE LYS GLU MET
GLY GLU MET HIS ARG GLU LEU ASN ALA—COOH
``` wherein ALA is an alanine residue, ARG is an arginine residue, ASN is an asparagine residue, ASP is an aspartic acid residue, CYS is a cysteine residue, GLN is a glutamine residue, GLU is a glutamic acid residue, GLY is a glycine residue, HIS is a histidine residue, ILE is an isoleucine residue, LEU is a leucine residue, LYS is a lysine residue, MET is a methionine residue, PHE is a phenylalanine residue, PRO is a proline residue, SER is a serine residue, THR is a threonine residue, TRP is a tryptophan residue, TYR is a tyrosine residue, and VAL is a valine residue.

The compounds of the present invention represent recombinant KSA, and the heretofore unknown amino acid and nucleotide sequences of nascent KSA. The nucleotide sequence of KSA is:

```
5'-GCA AAA CCT GAA GGG GCC
              CTC CAG AAC AAT GAT GGG CTT TAT GAT
CCT GAC TGC GAT GAG AGC GGG
```

-continued
```
            CTC TTT AAG GCC AAG CAG TGC AAC
GGC ACC TCC ACG TGC TGG TGT
            GTG AAC ACT GCT GGG GTC AGA AGA
ACA GAC AAG GAC ACT GAA ATA
            ACC TGC TCT GAG CGA GTG AGA ACC
TAC TGG ATC ATC ATT GAA CTA
            AAA CAC AAA GCA AGA GAA AAA CCT
TAT GAT AGT AAA AGT TTG CGG
            ACT GCA CTT CAG AAG GAG ATC ACA
ACG CGT TAT CAA CTG GAT CCA
            AAA TTT ATC ACG AGT ATT TTG TAT
GAG AAT AAT GTT ATC ACT ATT
            GAT CTG GTT CAA AAT TCT TCT CAA
AAA ACT CAG AAT GAT GTG GAC
            ATA GCT GAT GTG GCT TAT TAT TTT
GAA AAA GAT GTT AAA GGT GAA
            TCC TTG TTT CAT TCT AAG AAA ATG
GAC CTG ACA GTA AAT GGG GAA
            CAA CTG GAT CTG GAT CCT GGT CAA
ACT TTA ATT TAT TAT GTT GAT
            GAA AAA GCA CCT GAA TTC TCA ATG
```

-continued
```
            CAG GGT CTA AAA GCT GGT GTT
            ATT GCT GTT ATT GTG GTT GTG GTG
            ATG GCA GTT GTT GCT GGA ATT
            GTT GTG CTG GTT ATT TCC AGA AAG
            AAG AGA ATG GCA AAG TAT GAG
            AAG GCT GAG ATA AAG GAG ATG GGT
            GAG ATG CAT AGG GAA CTC AAT GCA-3'
``` wherein A is deoxyadenyl, G is deoxyguanyl, C is deoxycytidyl, and T is thymidyl.

The present invention further comprises a recombinant DNA compound which comprises DNA encoding a protein with the amino acid residue sequence:

```
ALA ALA GLN GLU GLU CYS VAL CYS GLU ASN TYR LYS LEU ALA VAL
ASN CYS PHE VAL ASN ASN ASN ARG GLN CYS GLN CYS THR SER VAL
GLY ALA GLN ASN THR VAL ILE CYS SER LYS LEU ALA ALA LYS CYS
LEU VAL MET LYS ALA GLU MET ASN GLY SER LYS LEU GLY ARG ARG
ALA LYS PRO GLU GLY ALA LEU GLN ASN ASN ASP GLY LEU TYR ASP
PRO ASP CYS ASP GLU SER GLY LEU P

```
ACT TTA ATT TAT TAT GTT GAT GAA AAA GCA CCT GAA TTC TCA ATG
CAG GGT CTA AAA GCT GGT GTT ATT GCT GTT ATT GTG GTT GTG GTG
ATG GCA GTT GTT GCT GGA ATT GTT GTG CTG GTT ATT TCC AGA AGA
AAG AGA ATG GCA AAG TAT GAG AAG GCT GAG ATA AAG GAG ATG GGT
GAG ATG CAT AGG GAA CTC AAT GCA-3'
``` wherein A is deoxyadenyl, G is deoxyguanyl, C is deoxycytidyl, and T is thymidyl.

The present invention further comprises a recombinant DNA compound which comprises DNA encoding a protein with the amino acid residue sequence:

```
NH2—MET ALA PRO PRO GLN VAL LEU ALA PHE GLY LEU LEU LEU ALA ALA ALA
     THR ALA THR PHE ALA ALA ALA GLN GLU GLU CYS VAL CYS GLU ASN TYR
     LYS LEU ALA VAL ASN CYS PHE VAL ASN ASN ASN ARG GLN CYS GLN CYS
     THR SER VAL GLY ALA GLN ASN THR VAL ILE CYS SER LYS LEU ALA ALA
     LYS CYS LEU VAL MET LYS ALA GLU MET ASN GLY SER LYS LEU GLY ARG
     ARG ALA LYS PRO GLU GLY ALA LEU GLN ASN ASN ASP GLY LEU TYR ASP
     PRO ASP CYS ASP GLU SER GLY LEU PHE LYS ALA LYS GLN CYS ASN GLY
     THR SER THR CYS TRP CYS VAL ASN THR ALA GLY VAL ARG ARG THR ASP
     LYS ASP THR GLU ILE THR CYS SER GLU ARG VAL ARG THR TYR TRP ILE
     ILE ILE GLU LEU LYS HIS LYS ALA ARG GLU LYS PRO TYR ASP SER LYS
     SER LEU ARG THR ALA LEU GLN LYS GLU ILE THR THR ARG TYR GLN LEU

ASP PRO LYS PHE ILE THR SER ILE LEU TYR GLU ASN ASN VAL ILE THR
     ILE ASP LEU VAL GLN ASN SER SER GLN LYS THR GLN ASN ASP VAL ASP
     ILE ALA ASP VAL ALA TYR TYR PHE GLU LYS ASP VAL LYS GLY GLU SER
     LEU PHE HIS SER LYS LYS MET ASP LEU THR VAL ASN GLY GLU GLN LEU
     ASP LEU ASP PRO GLY GLN THR LEU ILE TYR TYR VAL ASP GLU LYS ALA
     PRO GLU PHE SER MET GLN GLY LEU LYS ALA GLY VAL ILE ALA VAL ILE
     VAL VAL VAL VAL MET ALA VAL VAL ALA GLY ILE VAL VAL LEU VAL ILE
     SER ARG LYS LYS ARG MET ALA LYS TYR GLU LYS ALA GLU ILE LYS GLU
     MET GLY GLU MET HIS ARG GLU LEU ALA—COOH
``` wherein ALA is an alanine residue, ARG is an arginine residue, ASN is an asparagine residue, ASP is an aspartic acid residue, CYS is a cysteine residue, GLN is a glutamine residue, GLU is a glutamic acid residue, GLY is a glycine residue, HIS is a histidine residue, ILE is an isoleucine residue, LEU is a leucine residue, LYS is a lysine residue, MET is a methionine residue, PHE is a phenylalanine residue, PRO is a proline residue, SER is a serine residue, THR is a threonine residue, TRP is a tryptophan residue, TYR is a tyrosine residue, and VAL is a valine residue.

This compound represents recombinant KSA with a prepropeptide attached to the amino terminus, and the heretofore unknown amino acid and nucleotide sequences of nascent preproKSA. The nucleotide sequence of preproKSA for which only the coding strand is shown for convenience, is:

```
5'-ATG GCG CCC CCG CAG GTC CTC GCG TTC GGG CTT CTG CTT GCC GCG
    GCG ACG GCG ACT TTT GCC GCA GCT CAG GAA GAA TGT GTC TGT GAA
    AAC TAC AAG CTG GCC GTA AAC TGC TTT GTG AAT AAT AAT CGT CAA
    TGC CAG TGT ACT TCA GTT GGT GCA CAA AAT ACT GTC ATT TGC TCA
    AGG CTG GCT GCC AAA TGT TTG GTG ATG AAG GCA GAA ATG AAT GGC
    TCA AAA CTT GGG AGA AGA GCA AAA CCT GAA GGG GCC CTC CAG AAC
    AAT GAT GGG CTT TAT GAT CCT GAC TGC GAT GAG AGC GGG CTC TTT
    AAG GCC AAG CAG TGC AAC GGC ACC TCC ACG TGC TGG TGT GTG AAC
    ACT GCT GGG GTC AGA AGA ACA GAC AAG GAC ACT GAA ATA ACC TGC
    TCT GAG CGA GTG AGA ACC TAC TGG ATC ATC ATT GAA CTA AAA CAC
    AAA GCA AGA GAA AAA CCT TAT GAT AGT AAA AGT TGG CGG ACT GCA
    CTT CAG AAG GAG ATC ACA ACG CGT TAT CAA CTG GAT CCA AAA TTT
    ATC ACG AGT ATT TTG TAT GAG AAT AAT GTT ATC ACT ATT GAT CTG
    GTT CAA AAT TCT TCT CAA AAA ACT CAG AAT GAT GTG GAC ATA GCT
    GAT GTG GCT TAT TAT TTT GAA AAA GAT GTT AAA GGT GAA TCC TTG
    TTT CAT TCT AAG AAA ATG GAC CTG ACA GTA AAT GGG GAA CAA CTG
    GAT CTG GAT CCT GGT CAA ACT TTA ATT TAT TAT GTT GAT GAA AAA
    GCA CCT GAA TTC TCA ATG CAG GGT CTA AAA GCT GGT GTT ATT GCT
    GTT ATT GTG GTT GTG GTG ATG GCA GTT GTT GCT GGA ATT GTT GTG
    CTG GTT ATT TCC AGA AAG AAG AGA ATG GCA AAG TAT GAG AAG GCT
    GAG ATA AAG GAG ATG GGT GAG ATG CAT AGG GAA CTC AAT GCA-3'
``` wherein A is deoxyadenyl, G is deoxyguanyl, C is deoxycytidyl, and T is thymidyl.

Figure 17:
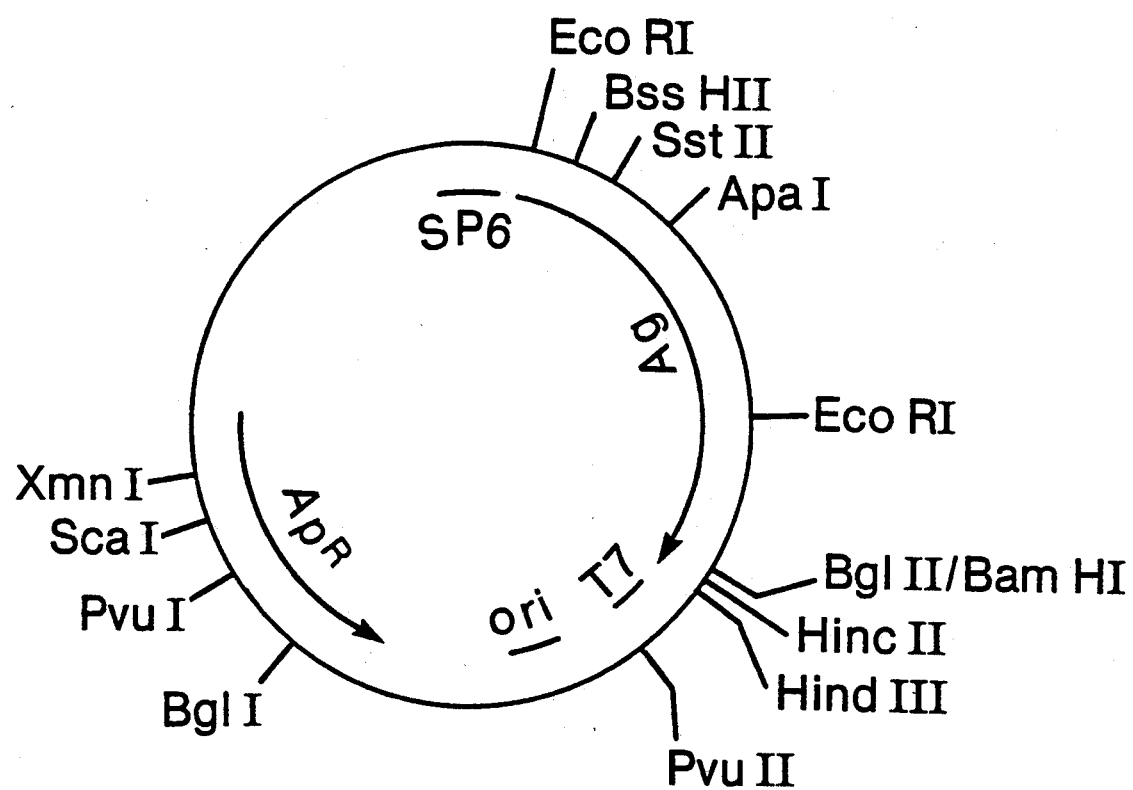
FIG. 17—the restriction site and function map of plasmid pGAG1317.

The DNA compounds of the present invention are derived from cDNA clones prepared from the mRNA from UCLA-P3 cells. Two of these cDNA clones were manipulated to construct a DNA molecule comprising both the nascent prepro-KSA and also portions of the DNA encoding the untranslated mRNA at the 5' and 3' ends of the coding region. These two cDNA containing plasmids were designated pAg932 and pAg1338. Plasmid pAg932 was digested with restriction enzymes EcoRI and SstII, and the resultant ~205 base pair fragment was isolated. Plasmid pAg1338 was digested with restriction enzyme SstII and BglII, and the resultant ~1100 base pair fragment was isolated. These two fragments were next ligated into plasmid pGEM TM-4 which had previously been digested with restriction enzymes EcoRI and BamHI. This ligation resulted in plasmid pGAG1317. A more detailed description of the construction of plasmid pGAG1317 is provided in Example 11. A restriction site and function map of plasmid pGAG1317 is presented in FIG. 17 of the accompanying drawings.

Figure 14:
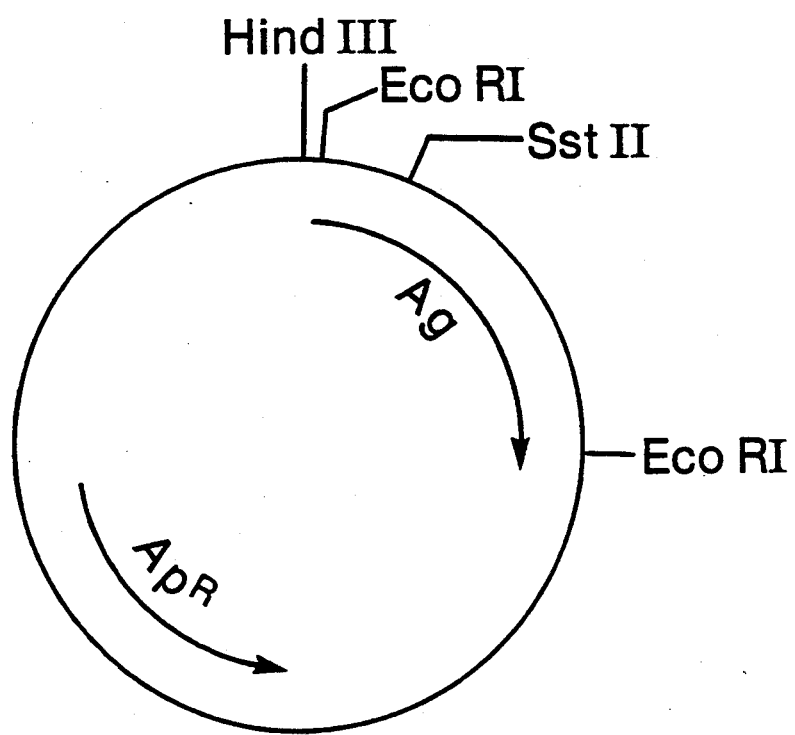
FIG. 14—the restriction site and function map of plasmid pAg932.
Figure 15:
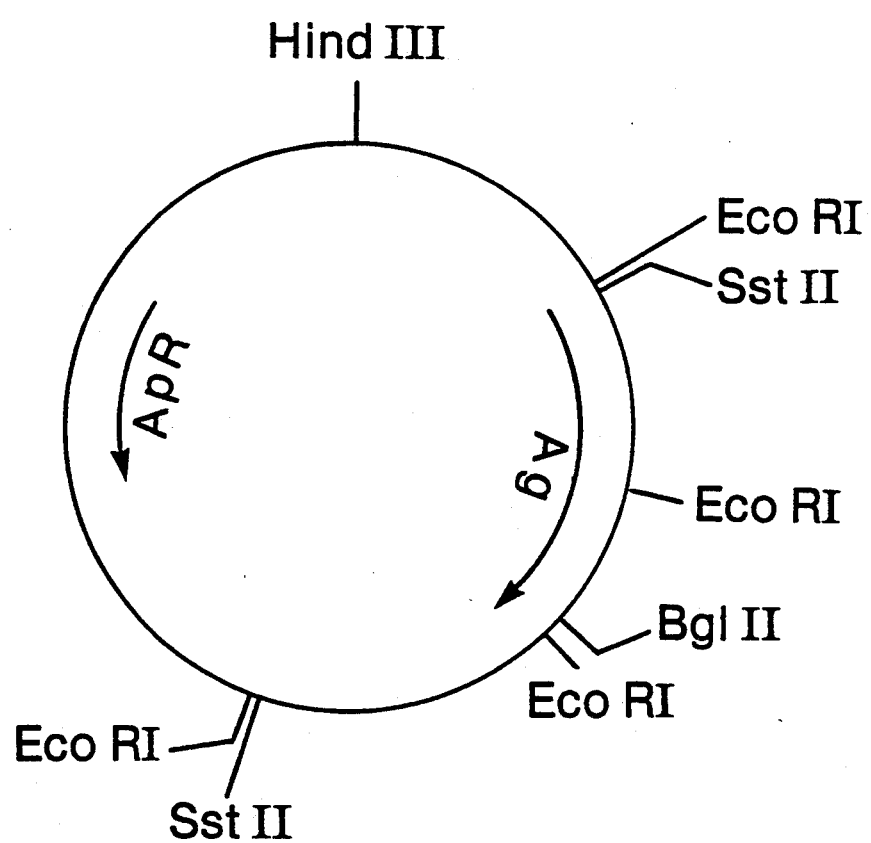
FIG. 15—the restriction site and function map of plasmid pAg1338.
Figure 16:
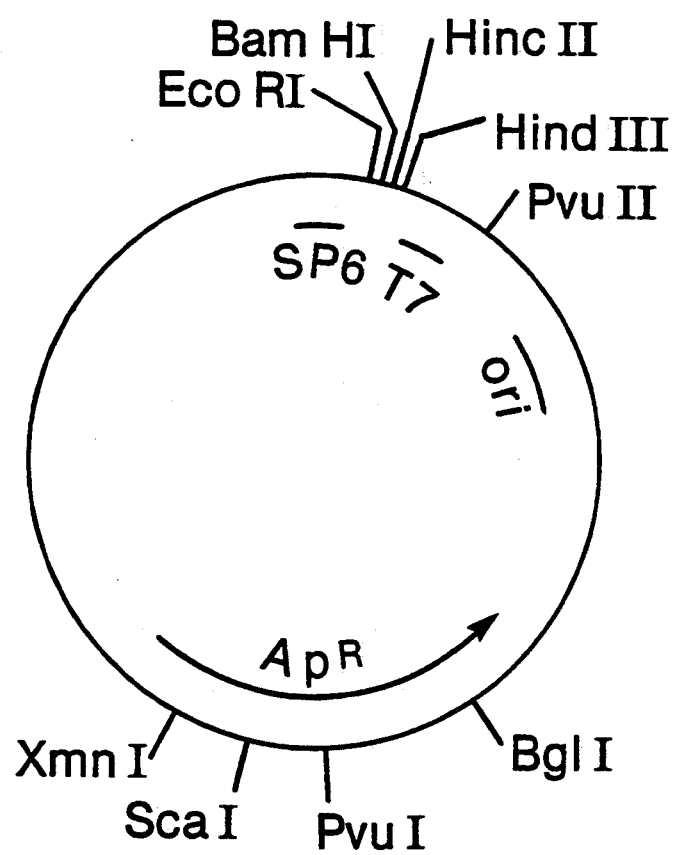
FIG. 16—the restriction site and function map of plasmid pGEM TM 4.

Plasmid pAg932 can be conventionally isolated from *E. coli* K12 DH5/pAg932, a strain deposited with and made part of the permanent stock culture collection of the Northern Regional Research Laboratory (NRRL), Peoria, Ill. A culture of *E. coli* K12 DH5/pAg932 can be obtained from the NRRL under the accession number NRRL B-18266. A restriction site and function map of plasmid pAg932 is presented in FIG. 14 of the accompanying drawings. Likewise, plasmid pAg1338 can be isolated from *E. coli* K12 DH5/pAg1338, also deposited and made part of the permanent stock culture collection of the NRRL. A culture of *E. coli* K12 DH5/pAg1338 can be obtained from the NRRL under the accession number NRRL B-18265. A restriction site and function map of plasmid pAg1338 is presented in FIG. 15 of the accompanying drawings. Plasmid pGEM TM-4 is publicly available and may be purchased from Promega Biotech, 2800 South Fish Hatchery Road, Madison, Wis. 53711. A restriction site and function map of plasmid pGEM TM-4 is presented in FIG. 16 of the accompanying drawings.

Plasmid pGAG1317 comprises both the coding sequence of preproKSA and also additional sequences which comprise the 5' and 3' untranslated regions of preproKSA. These additional sequences are:

```
5'-A ATT CCG AGC GAG CAC CTT CGA CGC GGT CCG GGG ACC CCC
   TCG TCG CTG TCC TCC CGA CGC GGA CCC CGC TGC CCC AGG
   CCT CGC GCT GCC CGG CCG GCT CCT CGT GTC CCA CTC CCG
   GCG CAC GCC CTC CCG CGC CCC TCT TCT CGG CGC GCG CGC
   AGC-3'
```
and
```
5'-TAA CTA TAT AAT TTG AAG ATT ATA GAA GAA GGG AAA TAG
   CAA ATG GAC ACA AAT TAC AAA TGT GTG TGC GTG GGA CGA
   AGA CAT CTT TGA AGG TCA TGA GTT TGT TAG TTT AAC ATC
   ATA TAT TTG TAA TAG TGA AAC CTG TAC TCA AAA TAT AAG
   CAG CTT GAA ACT GGC TTT ACC AAT CTT CAA ATT TGA CCA
   CAA GTG TCT TAT ATA TGC A-3'
``` wherein A is deoxyadenyl, G is deoxyguanyl, C is deoxycytidyl, and T is thymidyl, at the 5' and 3' ends, respectfully, of the coding strand of the nascent preproKSA coding sequence. Due to the complementary nature of DNA base-pairing, the sequence of one strand of a double-stranded DNA molecule is sufficient to determine the sequence of the opposing strand.

A variety of recombinant DNA expression vectors comprising the KSA encoding DNA have been constructed. The present vectors are of two types: those designed to transform eukaryotic, especially mammalian host cells; and those designed to transform *E. coli*. The eukaryotic or mammalian vectors exemplified herein can also transform *E. coli*, but the eukaryotic promoter present on these plasmids for transcription of KSA encoding DNA functions inefficiently in *E. coli*.

The present DNA compounds which encode nascent KSA are especially preferred for the construction of vectors for transformation and expression of KSA in mammalian and other eukaryotic cells. Many mammalian host cells possess the necessary cellular machinery for the recognition and proper processing of signal (pre) peptide present on the amino-terminus of KSA. Some mammalian host cells also provide the post-translational modifications, such as glycosylation, that are observed in KSA present on the surface of adenocarcinoma cells. A wide variety of vectors exist for the transformation of eukaryotic host cells, and the specific vector exemplified below is in no way intended to limit the scope of the present invention.

The BK enhancer-type vector of the present invention comprises a BK enhancer-adenovirus late promoter cassette plus a hygromycin resistance conferring gene and a murine dihydrofolate reductase (dhfr) gene. The use of the BK virus enhancer in conjunction with the adenovirus late promoter significantly increases transcription of a recombinant gene in eukaryotic host cells. The hygromycin resistance-conferring gene is present as a selectable marker for use in eukaryotic host cells. The murine dihydrofolate reductase gene, under appropriate conditions, is amplified in the host chromosome. This amplification, described in a review by Schimke, 1984, Cell 37:705–713, can also involve DNA sequences closely contiguous with the dhfr gene. The dhfr gene is a selectable marker in dhfr-negative cells and can be used to increase the copy number of a DNA segment by exposing the host cell to increasing levels of methotrexate.

Plasmid pLPChd may be used to construct a eukaryotic expression vector for expression of the novel KSA structural gene of the present invention. Plasmid pLPChd contains the dhfr gene, the Adenovirus type-2 promoter and the BK virus enhancer. The BK virus, which contains the BK virus enhancer, can be purchased or readily isolated in large quantities as described in Example 13. The BK virus is also available from the American Type Culture Collection under the accession number ATCC VR-837.

The BK viral genome was combined with a portion of plasmid pdBPV-MMTneo to construct plasmids pBKneo1 and pBKneo2. Plasmid pdBPV-MMTneo, about 15 kb in size and available from the ATCC under the accession number ATCC 37224, comprises the replicon and β-lactamase gene from plasmid pBR322, the mouse metallothionein promoter positioned to drive expression of a structural gene that encodes a neomycin resistance-conferring enzyme, and about 8 kb of bovine papilloma virus (BPV) DNA. Plasmid pdBPV-MMTneo can be digested with restriction enzyme BamHI to generate two fragments: the ~8 kb fragment that comprises the BPV DNA and an ~7 kb fragment that comprises the other sequences described above. BK virus has only one BamHI restriction site, and plasmids pBKneo1 and pBKneo2 were constructed by ligating the ~7 kb BamHI restriction fragment of plasmid pdBPV-MMTneo to BamHI-linearized BK virus DNA. The construction of plasmids pBKneo1 and pBKneo2, which differ only with respect to the orientation of the BK virus DNA, is described in Example 14. Plasmid pBKneo1 contains an ~2.1 kb SalI-HindIII restriction fragment, whereas plasmid pBKneo2 contains an ~1.0 kb restriction fragment.

Plasmids pBKneo1 and pBKneo2 each comprise the entire genome of the BK virus, including the enhancer sequence, and thus serve as useful starting materials for the expression vector of the present invention. Expression vector, plasmid pBLcat, comprises the BK enhancer sequence in tandem with the human adenovirus-type-2 late promoter positioned to drive expression of the chloramphenicol acetyltransferase enzyme (CAT). Plasmid pSV2cat serves as a convenient source of the CAT gene and can be obtained from the ATCC under the accession number ATCC 37155. Human adenovirus-type-2 DNA is commercially available and can also be obtained from the ATCC under the accession number ATCC VR-2.

Illustrative plasmid pBLcat was constructed by ligating the ~0.32 kb late-promoter-containing AccI-PvuII restriction fragment of human adenovirus-type-2 DNA to blunt-ended BclI linkers that attached only to the PvuII end of the AccI-PvuII restriction fragment. The resulting fragment was then ligated to the ~4.51 kb AccI-StuI restriction fragment of plasmid pSV2cat to yield intermediate plasmid pLPcat. The desired plasmid pBLcat was constructed from plasmid pLPcat by ligating the origin of replication and enhancer-containing ~1.28 kb AccI-PvuII restriction fragment of BK virus DNA to the ~4.81 kb AccI-StuI restriction fragment of plasmid pLPcat. The construction of plasmid pBLcat is further described in Example 15.

Plasmid pL133 was next constructed from plasmids pHC7, pSV2gpt and pSV2-β-globin. Plasmid pHC7 comprises a DNA sequence which encodes human protein C. Plasmid pHC7 can be isolated from *E. coli* K12 RR1/pHC7 which is available from the NRRL under accession number NRRL B-15926. Plasmid pHC7 was cut with restriction enzyme BanI and the ~1.25 kb restriction fragment was isolated. Linkers were added, and the fragment was then cut with restriction enzymes ApaI and HindIII, then the desired ~1.23 kb restriction fragment was isolated. Plasmid pHC7 was next cut with restriction enzyme PstI, the ~0.88 kb restriction fragment was isolated, linkers were added, the fragment was re-cut with restriction enzymes ApaI and BglII and the ~0.19 kb ApaI-BglII restriction fragment was isolated. Plasmid pSV2gpt (ATCC 37145) was digested with restriction enzymes HindIII and BglII and the ~5.1 kb fragment was isolated. The ~1.23 kb HindIII-ApaI restriction fragment, the ~0.19 kb ApaI-BglII fragment and the ~5.1 kb HindIII-BglII fragment were then ligated together to form intermediate plasmid pSV2-HPC8. A more detailed explanation of the construction of plasmid pSV2-HPC8 is presented in Example 16.

Plasmid pSV2-HPC8 was then cut with restriction enzymes HindIII and SalI, and the ~0.29 kb restriction fragment was isolated. Likewise, plasmid pSV2-HPC8 was also cut with restriction enzymes BglII and SalI, and the ~1.15 kb restriction fragment was isolated. Plasmid pSV2-β-globin (NRRL B-15928) was cut with restriction enzymes BglII and HindIII and the ~4.2 kb restriction fragment was isolated. These three fragments were then ligated together to form plasmid pL133. A detailed description of the construction of plasmid pL133 is found in Example 16.

Plasmid pL133 was digested with restriction enzyme HindIII, then treated with alkaline phosphatase. Plasmid pBLcat was also cut with restriction enzyme HindIII and the ~0.87 kb restriction fragment was isolated. This fragment was ligated into the HindIII cut, phosphatased plasmid pL133 vector to form plasmid pLPC. Because the HindIII fragment of plasmid pBLcat can be inserted into plasmid pL133 in two orientations, it should be noted that pLPC is the plasmid wherein the proper orientation provides an ~1.0 kb NdeI-StuI fragment. Plasmid pLPC, like plasmid pL133, comprises the enhancer, early and late promoters, T-antigen-binding sites, and origin of replication of SV40. A detailed protocol for the construction of plasmid pLPC is provided in Example 17.

The SV40 elements present on plasmid pLPC are situated closely together and difficult to delineate. The binding of T antigen to the T-antigen-binding sites, which is necessary for SV40 replication, is known to enhance transcription from the SV40 late promoter and surprisingly has a similar effect on the BK late promoter. Because the high level of T-antigen-driven replication of a plasmid that comprises the SV40 origin of replication is generally lethal to the host cell, neither plasmid pLPC nor plasmid pL133 are stably maintained as episomal (ectrachromosomal) elements in the presence of SV40 T antigen, but rather, the two plasmids must integrate into the chromosomal DNA of the host cell to be stably maintained.

The overall structure of the BK enhancer region is quite similar to that of SV40, for the BK enhancer, origin of replication, early and late promoters, and the BK analogue of the T-antigen-binding sites are all closely situated and difficult to delineate on the BK viral DNA. However, when grown in the presence of BK T antigen, a plasmid that comprises the BK origin of replication and T-antigen-binding sites does not replicate to an extent that proves lethal and is stably maintained as an episomal element in the host cell. In addition, the T-antigen-driven replication can be used to increase the copy number of a vector comprising the BK origin of replication so that when selective pressure is applied more copies of the plasmid integrate into the host cell's chromosomal DNA. Apparently due to the similar structure-function relationships between the BK and SV40 T antigens and their respective binding sites, BK replication is also stimulated by SV40 T antigen.

Episomal maintenance of a recombinant DNA expression vector is not always preferred over integration into the host cell chromosome. However, due to the absence of a selectable marker that functions in eukaryotic cells, the identification of stable, eukaryotic transformants of plasmid pLPC is difficult, unless plasmid pLPC is cotransformed with another plasmid that does comprise a selectable marker. Consequently, plasmid pLPC has been modified to produce derivative plasmids that are selectable in eukaryotic host cells.

This was done by ligating plasmid pLPC to a portion of plasmid pSV2hyg, a plasmid that comprises a hygromycin resistance-conferring gene. Plasmid pSV2hyg can be obtained from the Northern Regional Research Laboratory (NRRL), Peoria, Ill. 61640, under the accession number NRRL B-18039. Plasmid pSV2hyg was digested with restriction enzyme BamHI, and the ~2.5 kb BamHI restriction fragment, which comprises the entire hygromycin resistance-conferring gene, was isolated, treated with Klenow enzyme (the large fragment produced upon subtilisin cleavage of *E. coli* DNA polymerase I), and then ligated to the Klenow-treated, ~5.82 kb NdeI-StuI restriction fragment of plasmid pLPC to yield plasmids pLPChyg1 and pLPChyg2. Plasmids pLPChyg1 and pLPChyg2 differ only with respect to the orientation of the hygromycin resistance-conferring fragment. Plasmid pLPChyg1 contains an ~5.0 kb HindIII fragment whereas plasmid pLPChyg2 contains an ~1.0 kb fragment. The construction protocol for plasmids pLPChyg1 and pLPChyg2 is described in Example 18.

Plasmid pBW32, which contains the murine dihydrofolate reductase (dhfr) gene, was constructed next. Plasmid pTPA102 (NRRL B-15834) was cut with restriction enzyme Tth111I and the ~4.4 kb restriction fragment was isolated. This fragment was treated with Klenow, linkers were added, then the fragment was cut with restriction enzymes HindIII and BamHI to yield an ~2.0 kb restriction fragment. Plasmid pRC was then constructed by ligating the ~288 bp ClaI-EcoRI restriction fragment of pTPA102 into ClaI-EcoRI cut vector pKC7. Plasmid pKC7 can be obtained from the ATCC under the accession number ATCC 37084. Plasmid pRC was digested with restriction enzymes BamHI and HindIII, then ligated to the ~2.0 kb restriction fragment of plasmid pTPA102, formed above, to yield plasmid pTPA103. The construction protocol for plasmid pTPA103 is described in Example 19A.

Plasmid pTPA103 was cut with restriction enzyme BglII, treated with Klenow, and the NdeI linkers were added. This mixture was then ligated to form plasmid pTPA103derNdeI. Plasmid pTPA103derNdeI was cut with restriction enzyme AvaII, and the ~1.4 kb fragment was isolated. This fragment was treated with Klenow, then, after the addition of HpaI linkers, was cut with restriction enzyme EcoRI. The ~770 bp fragment, containing trpPO and the amino terminus of TPA, was ligated into EcoRI-SmaI digested vector pUC19, to form pUC19TPAFE. Plasmid pUC19TPAFE was partially digested with restriction enzyme HpaI, then totally cut with restriction enzyme BamHI. The resultant ~3.42 kb HpaI-BamHI restriction fragment was then ligated to the ~1.015 ScaI-BamHI fragment derived from plasmid pTPA103 to form plasmid pBW25. The construction protocol for plasmid pBW25 is described in Example 19B.

Plasmid pBW25 was cut with restriction enzymes HindIII and EcoRI and the resultant ~810 bp fragment was ligated into HindIII-EcoRI cut phage M13mp8 (New England Biolabs) to form phage pM8BW26. An in vitro mutagenesis reaction was then performed on phage pM8BW26 (deleting DNA coding for amino acid residues) to form phage pM8BW27. Phage pM8BW27 was cut with restriction enzymes EcoRI and NdeI and the ~560 bp restriction fragment was isolated. A synthetic NdeI-XbaI linker of ~48 bp was synthesized. Plasmid pTPA103 was cut with restriction enzymes EcoRI and BamHI and the ~689 bp fragment was isolated. Plasmid pL110 (constructed in Example 9) was partially digested with restriction enzyme BamHI, then totally cut with XbaI and the ~6.0 kb fragment was isolated. This ~6.0 kb vector fragment, the ~689 bp fragment of plasmid pTPA103, the ~560 bp fragment of phage pM8BW27, and the ~48 bp linker were all then ligated together to form plasmid pBW28. The construction protocol of plasmid pBW28 is described in Example 19C.

Plasmid pTPA301 was next formed by ligating the ~2.0 kb HindIII-BglII fragment of plasmid pTPA103 to the ~4.2 kb HindIII-BglII fragment of plasmid pSv2-β-globin. Plasmid pSV2-dhfr (ATCC 37146) was cut with restriction enzyme PvuII. Following the addition of BamHI linkers, the ~1.9 kb dhfr gene-containing fragment was ligated into BamHI cut, phosphatased plasmid pTPA301 to form plasmid pTPA303. Plasmid pTPA301 was cut with restriction enzymes EcoRI and BglII to yield an ~2.7 kb fragment. Plasmid pTPA303 was cut with restriction enzymes HindIII and EcoRI to yield the ~2340 bp dhfr gene containing fragment. Plasmid pTPA303 was cut with restriction enzymes HindIII and SstI to yield an ~1.7 kb fragment. Plasmid pBW28 was cut with restriction enzymes XhoII and SstI to yield an ~680 bp fragment. The ~2.7 kb EcoRI-BglII fragment of plasmid pTPA301, the ~2340 bp HindIII-EcoRI fragment of plasmid pTPA303, the ~1.7 kb HindIII-SstI fragment of plasmid pTPA303 and the ~680 bp XhaII-SstI fragment of plasmid pBW28 were all ligated together to form plasmid pBW32. The construction protocol of plasmid pBW32 is described in Example 19D.

Figure 20:
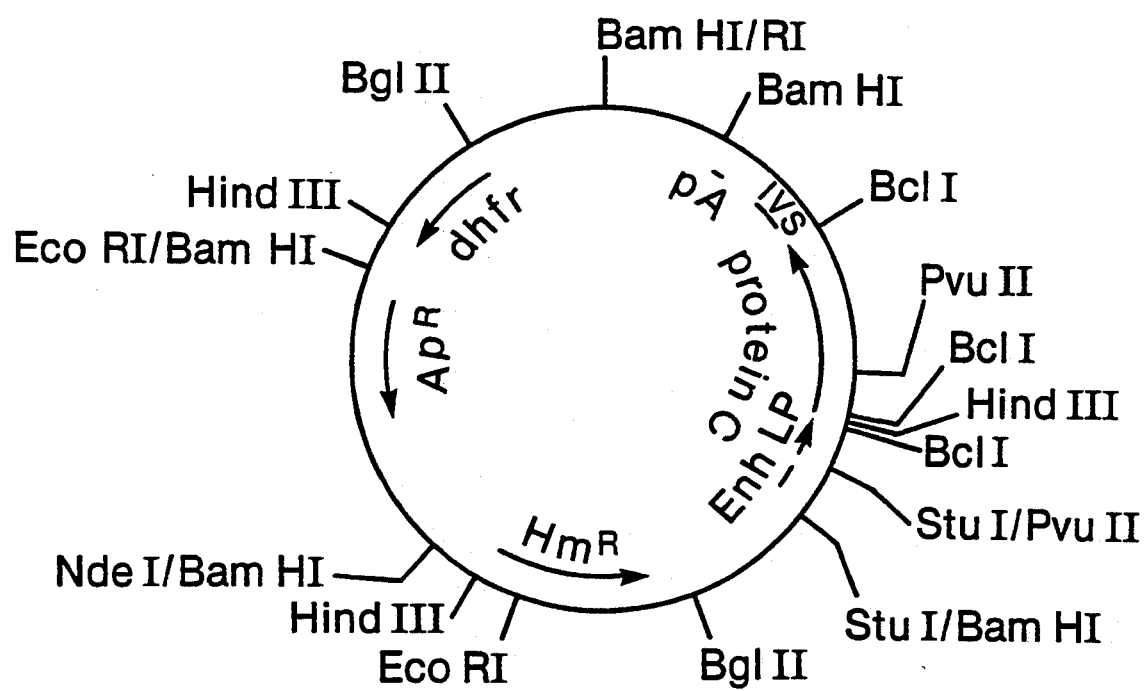
FIG. 20—the restriction site and function map of plasmid pLPChd.

The dhfr gene-containing, ~1.9 kb BamHI restriction fragment of plasmid pBW32 was isolated, treated with Klenow enzyme, and inserted into partially-EcoRI-digested plasmid pLPChyg1 to yield plasmids pLPChd1 and pLPChd2. Plasmid pLPChyg1 contains two EcoRI restriction enzyme recognition sites, one in the hygromycin resistance-conferring gene and one in the plasmid pBR322-derived sequences. The fragment comprising the dhfr gene was inserted into the EcoRI site located in the pBR322-derived sequences of plasmid pLPChyg1 to yield plasmids pLPChd1 and pLPChd2. For the purposes of this disclosure, plasmid pLPChd1 has been designated plasmid pLPChd. A restriction site and function map of plasmid pLPChd is presented in FIG. 20 of the accompanying drawings. The construction of plasmids pLPChd1 and pLPChd2, which differ only with respect to the orientation of the dhfr gene-containing DNA segment, is described in Example 20.

Figure 21:
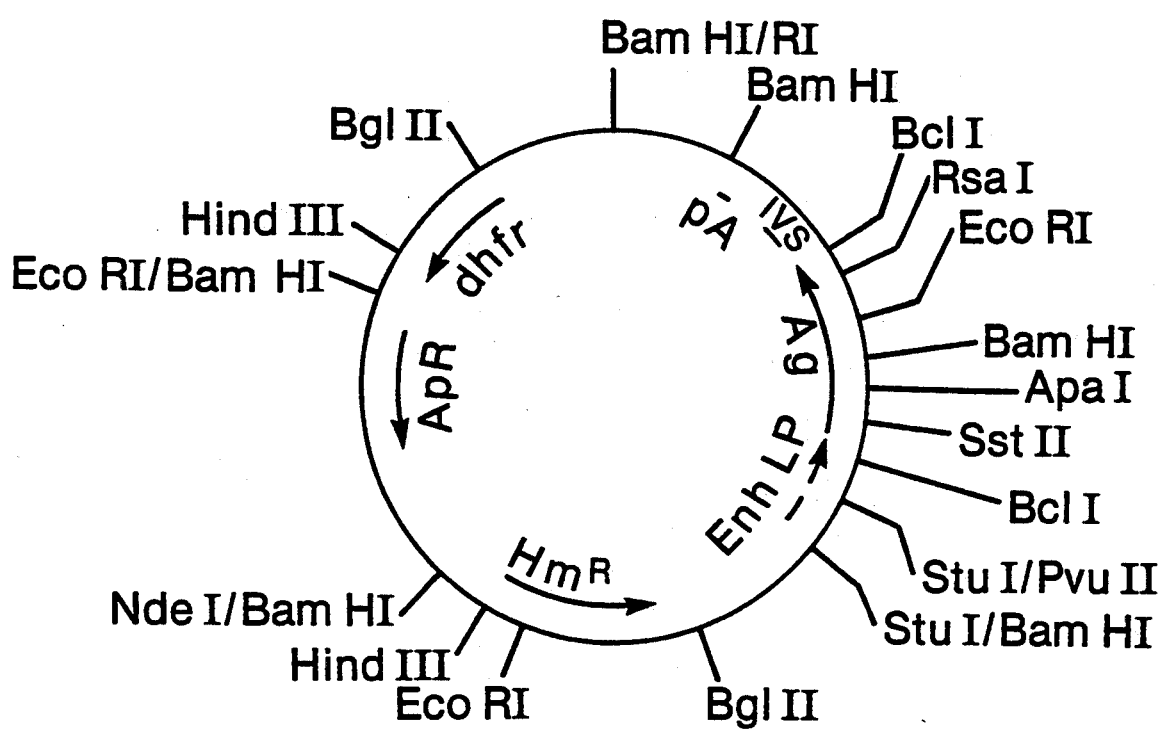
FIG. 21—the restriction site and function map of plasmid pALPKSA.

Plasmid pALPKSA is a vector of the present invention derived from plasmid pGAG1317 and plasmid pLPChd. The ~1200 base pair BssHII-HincII fragment of plasmid pGAG1317 is treated with Klenow to fill in the 5' overhang. This fragment represents the entire KSA coding region. This fragment is then ligated into the BclI-digested, purified vector pLPChd. This essentially substitutes the protein C structural gene of plasmid pLPChd with the KSA structural gene of plasmid pGAG1317 to form preferred expression vector pALPKSA. A more detailed description of the construction of plasmid pALPKSA is provided in Example 21. A restriction site and function map of plasmid pALPKSA is presented in FIG. 21 of the accompanying drawings.

The present invention is in no way limited to the use of the particular eukaryotic promoters exemplified herein. Other promoters, such as the SV40 late promoter or promoters from eukaryotic genes, such as for example, the estrogen-inducible chicken ovalbumin gene, the interferon genes, the glucocorticoid-inducible tyrosine aminotransferase gene, the thymidine kinase gene, the major early adenovirus gene, and the SV40 early promoter, can be readily isolated and modified for use on recombinant DNA expression vectors designed to produce KSA in eukaryotic host cells. Eukaryotic promoters can also be used in tandem to drive expression of KSA. Furthermore, a large number of retroviruses are known that infect a wide range of eukaryotic host cells. Long terminal repeats in the retrovirus DNA often encode promoter activity and can be used, in place of the BK enhancer-adenovirus late promoter described above, to drive expression of KSA.

The vector pALPKSA can be transformed into and expressed in a variety of eukaryotic, especially mammalian host cells. Plasmid pALPKSA also comprises sequences that allow for replication in *E. coli*, as it is usually more efficient to prepare plasmid DNA in *E. coli* than in other host cells. Expression of KSA occurs in host cells in which the particular promoter associated with the nascent KSA structural gene functions. Skilled artisans will understand that a variety of eukaryotic host cells can be used to express KSA using the BK enhancer-adenovirus late promoter, so long as the host cell expresses an immediate-early gene product of a large DNA virus. Because the immediate-early gene product can be introduced into host cells by many means, such as transformation with a plasmid or other vector, virtually any eukaryotic cell can be used in the present method. Human cells are preferred host cells in the method of the present invention, because human cells are the natural host for BK virus and may contain cellular factors that serve to stimulate the BK enhancer. While human kidney cells are especially preferred as host cells, the adenovirus 5-transformed embryonic cell line 293, which expresses the E1A gene product, is most preferred and is available from the American Type Culture Collection in Rockville, Md., under the accession number ATCC CRL 15753.

The present DNA compounds can also be expressed in prokaryotic host cells such as, for example, *E. coli*, Bacillus and Streptomyces. Since prokaryotic host cells usually do not glycosylate, and often do not properly fold, mammalian proteins made from recombinant genes, a variety of novel KSA derivatives can be produced by expressing the present KSA-encoding DNA in prokaryotic host cells. The novel KSA derivatives expressed in prokaryotic host cells may show varying degrees of reactivity with monoclonal antibody KS 1/4 and can be used to determine the folding and post-translational modification requirements for specific antibody/antigen interactions. The novel KSA derivatives may also be used to create novel, heretofore unknown antibodies which react only to specific portions of KSA. Skilled artisans will readily understand that the ability of an antibody to recognize certain portions of an antigen is essential when using competitive assays for diagnosis or therapy.

Before expressing the KSA-encoding DNA compounds of the present invention in prokaryotic host cells, the DNA encoding the eukaryotic signal peptide (prepeptide) and the eukaryotic propeptide was removed. Although the present invention is not limited or dependent on any theory of mode of action, it is believed that the first 21 amino acid residues at the amino-terminus of nascent preproKSA act as a signal peptide (prepeptide). The present invention is not limited to the use of a particular eukaryotic signal peptide for expression of KSA in eukaryotic host cells. Furthermore, the next 60 amino acid residues at the amino-terminus of nascent prepro-KSA act as a propeptide. The removal of the prepropeptide forms a molecule which has a nascent chain that is substantially the same as the nascent chain of the KSA found on the cell surface of UCLA-P3 cells. As a general rule, prokaryotes do not efficiently process eukaryotic signal peptides; therefore it is somewhat inefficient to express the signal peptide-encoding portion of the nascent KSA structural gene in prokaryotes. Although not specifically exemplified herein, the present invention also comprises the fusion of a prokaryotic signal peptide-encoding DNA to the KSA-encoding DNA of the present invention for expression and secretion of KSA in prokaryotes.

In addition to the modifications stated above, certain other regions of the KSA-encoding DNA were removed before the molecule was expressed in prokaryotes. Specifically, the DNA encoding the 49 amino acid residues at the carboxy-terminus of nascent KSA was removed. This represents the removal of the entire cytoplasmic domain and transmembrane region of nascent KSA. Therefore expression of the DNA of this molecule will lead to a KSA derivative which contains substantially the same amino acid structure as the nascent chain KSA found on the surface of UCLA-P3 cells.

As stated above, amino acid residues 1–21 of nascent KSA which may encode a "signal" (prepeptide) for extracellular secretion of a portion of KSA, are not present in the nascent KSA found on the surface of adenocarcinoma cells. Residues 22–81 of nascent KSA, which comprise a propeptide of KSA, are also removed during the processing of the protein and are believed to be responsible for the correct folding and modification of the molecule. Residues 82–265 of nascent KSA are encoded in the prokaryotic expression vector exemplified below, but residues 266–314 are not; those residues comprise the cytoplasmic domain and transmembrane region.

However, the present invention is not limited to the expression of a particular KSA derivative. The present DNA compounds are readily modified to delete certain portions encoding various amino acid residues of the KSA. Those skilled in the art recognize that restriction enzyme digestion or site-directed mutagenesis upon the DNA compounds of the present invention will yield an almost limitless group of molecules which will encode for KSA derivatives. Such manipulations are within the scope of this invention, and can be performed given the detailed sequences disclosed herein.

Plasmid pLKSA is a plasmid of the present invention designed to express amino acid residues 82–265 of the KSA in *E. coli*. Plasmid pLKSA was constructed from plasmid pGAG1317 and plasmid pL110C. Plasmid pGAG1317 was described and disclosed earlier. A brief description of the construction of plasmid pL110C is provided below and a detailed description is provided in Examples 1–10. A restriction site and function map of plasmid pL110C is presented in FIG. 13 of the accompanying drawings.

Plasmid pKC283 was first obtained from *E. coli* K12 BE1201/pKC283. This culture may be obtained from the NRRL under accession number NRRL B-15830. Plasmid pKC283 comprises a hybrid lpp-pL promoter of bacterio-phage λ. This plasmid is obtained in *E. coli* K12 BE1201 cells because these cells comprise a temperature sensitive cI repressor integrated into the cellular DNA. A detailed description of the isolation of plasmid pKC283 is presented in Example 1. A restriction site and function map of plasmid pKC283 is presented in FIG. 1 of the accompanying drawings.

Figure 2:
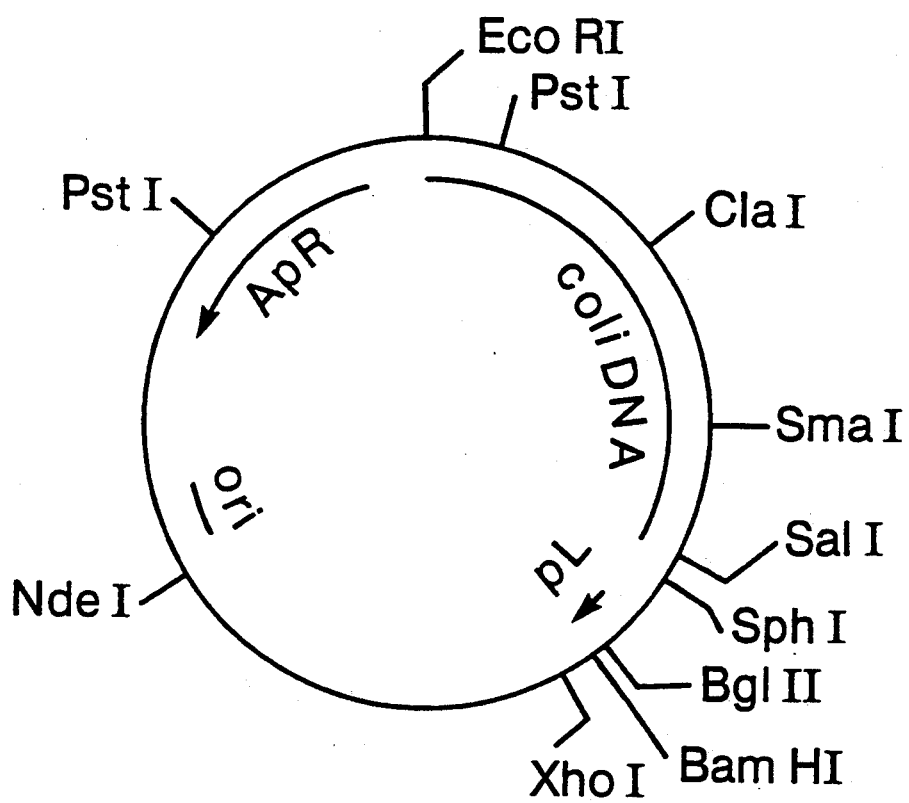
FIG. 2—the restriction site and function map of plasmid pKC283PX.

The unneeded lacZ portion of plasmid pKC283 was excised by first digesting the plasmid with restriction enzyme PvuII. Specific DNA linkers were then added to the digested DNA to convert the pVuII sites into a single XhoI site, which created plasmid pKC283PX. A detailed description of the isolation of plasmid pKC283PX is presented in Example 2. A restriction site and function map of plasmid pKC283PX is presented in FIG. 2 of the accompanying drawings. As explained in Example 3, plasmid pKC283PX is transformed into *E. coli* K12 MO(λ+). *E. coli* K12 MO(λ+) is available from the NRRL under the accession number NRRL B-15993.

Figure 3:
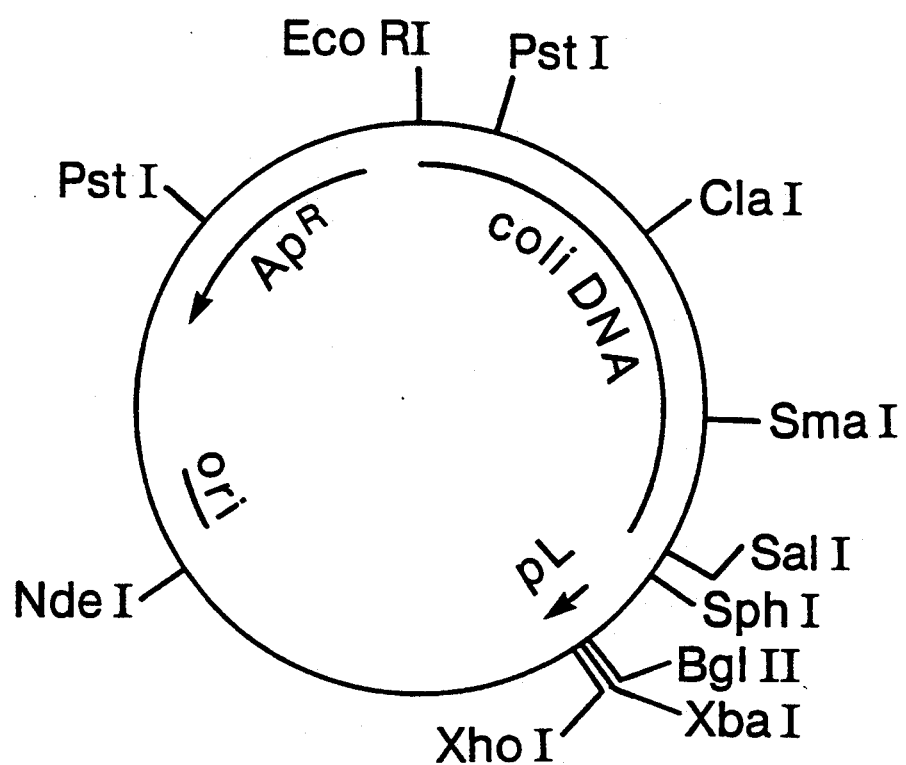
FIG. 3—the restriction site and function map of plasmid pKC283-L.

Plasmid pKC283PX was next digested with restriction enzymes BglII and XhoI. After the vector was purified, DNA linkers with BglII and XhoI ends were ligated into the vector to form plasmid pKC283-L. The BglII-XhoI linker also contained an XbaI site. A detailed description of the construction of plasmid pKC283-L is presented in Example 4. A restriction site and function map of plasmid pKC283-L is presented in FIG. 3 of the accompanying drawings.

Figure 4:
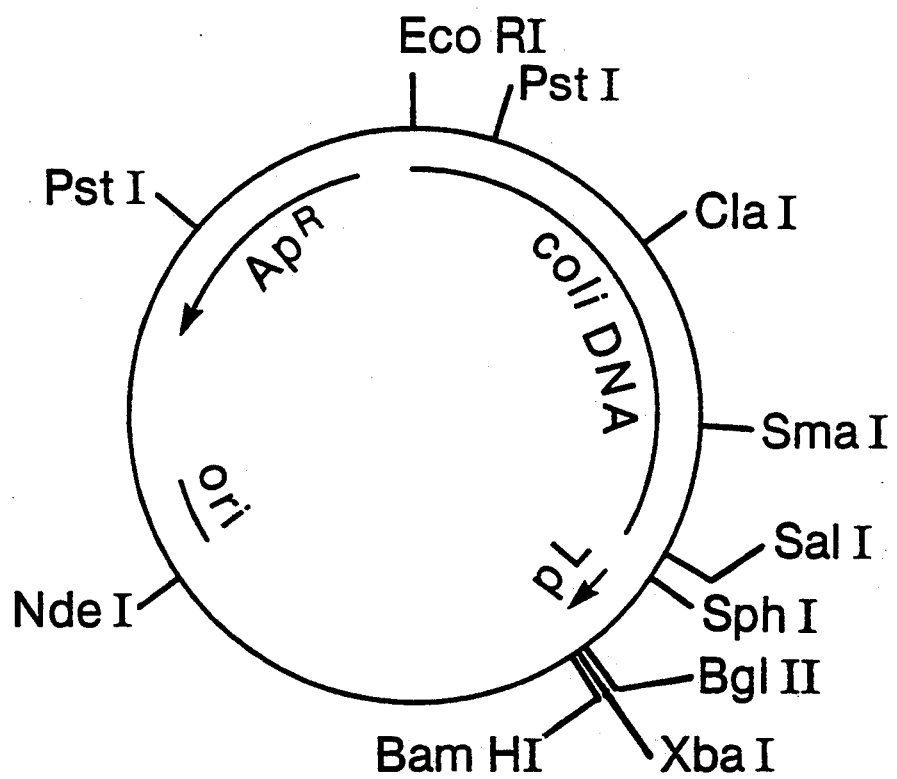
FIG. 4—the restriction site and function map of plasmid pKC283-LB.

The XhoI site of plasmid pKC283-L was next converted into a BamHI site. This was accomplished by a total digestion of plasmid pKC283-L with restriction enzyme XhoI, followed by treatment with Klenow, then addition of BamHI linkers, to form plasmid pKC283-LB. A detailed description of the construction of plasmid pKC283-LB is presented in Example 5. A restriction site and function map of plasmid pKC283-LB is presented in FIG. 4 of the accompanying drawings.

Figure 5:
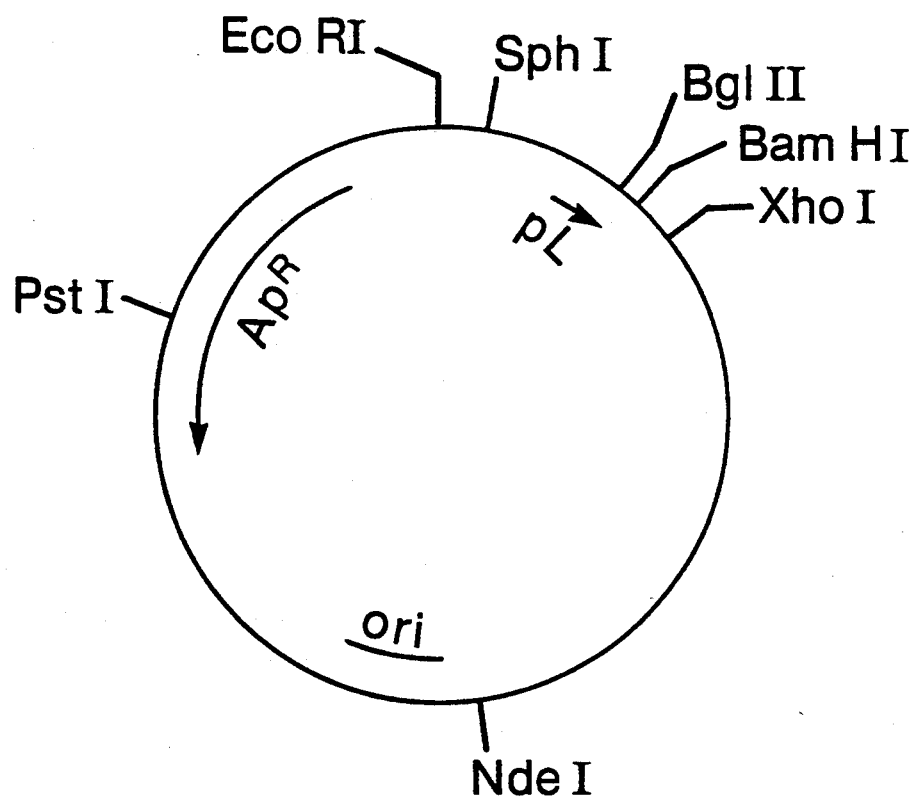
FIG. 5—the restriction site and function map of plasmid pKC283PRS.

The extraneous E. coli DNA was next excised from plasmid pKC283PX by total digestion with restriction enzyme SalI, followed by treatment of the ~4.0 kb vector with Klenow, then addition of EcoRI linkers. Upon recircularization via ligation, this formed plasmid pKC283PRS. A detailed description of the construction of plasmid pKC283PRS is presented in Example 6. A restriction site and function map of plasmid pKC283PRS is presented in FIG. 5 of the accompanying drawings.

Figure 6:
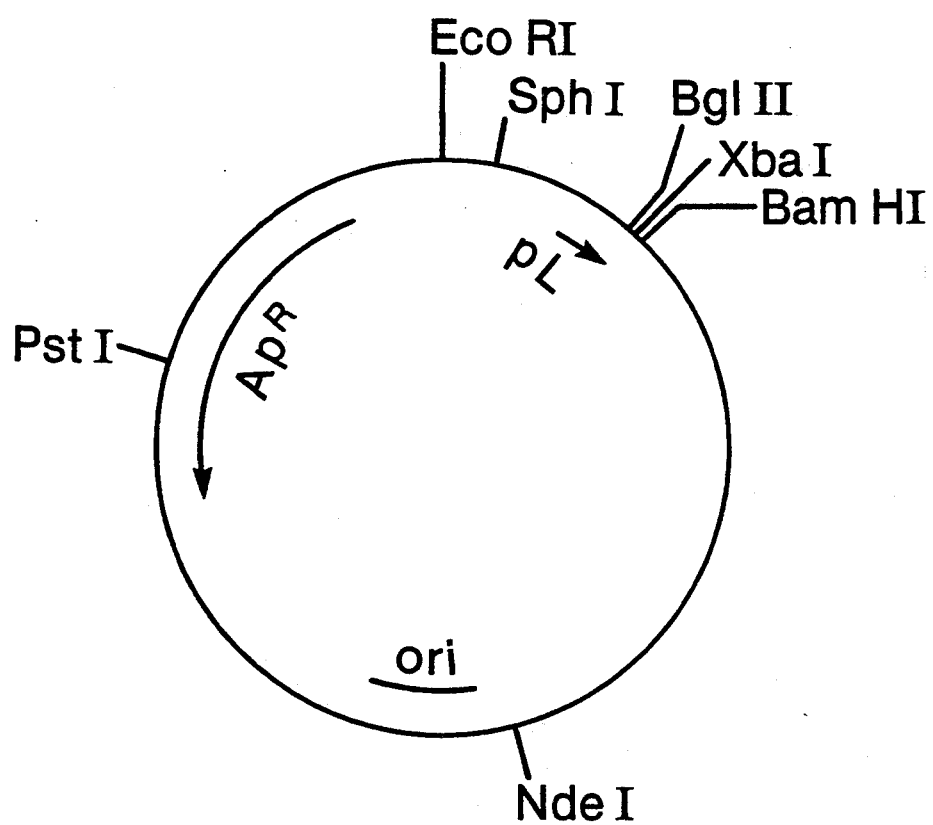
FIG. 6—the restriction site and function map of plasmid pL32.

Plasmid pKC283PRS was then digested with restriction enzymes PstI and SphI and the ~0.85 kb PstI-SphI restriction fragment was isolated. In an analogous manner, plasmid pKC283-LB was digested with restriction enzymes PstI and SphI and the ~3.0 kb fragment was isolated. The ~0.85 kb PstI-SphI fragment of pKC283PRS was then ligated into the ~3.0 kb PstI-SphI vector fragment of pKC283-LB to form plasmid pL32. A detailed description of the construction of plasmid pL32 is presented in Example 6. A restriction site and function map of plasmid pL32 is presented in FIG. 6 of the accompanying drawings.

Figure 7:
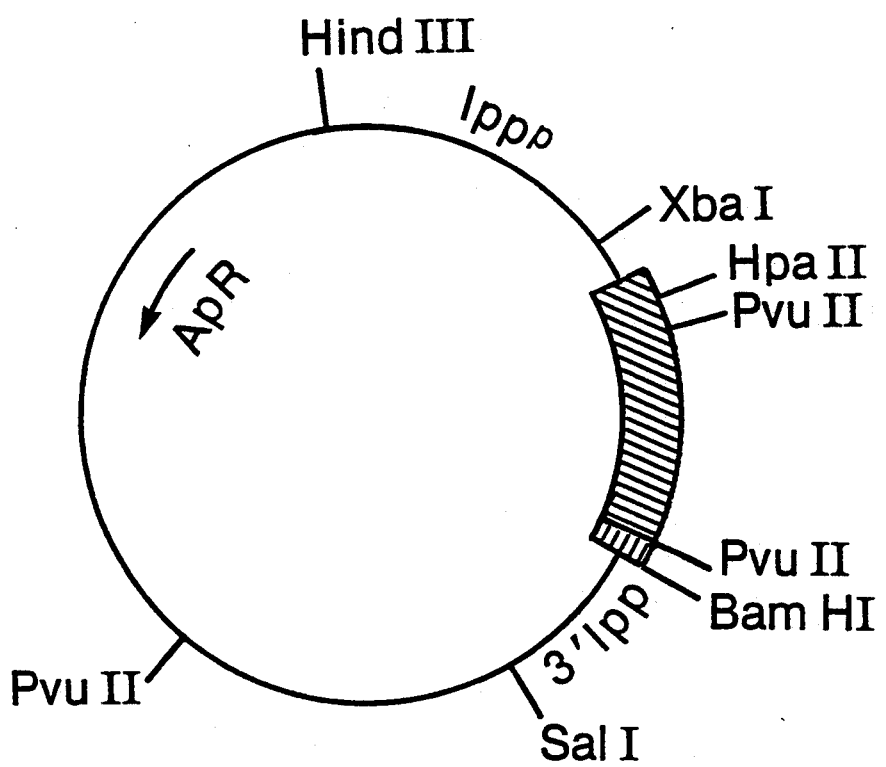
FIG. 7—the restriction site and function map of plasmid pNM789.
Figure 8:
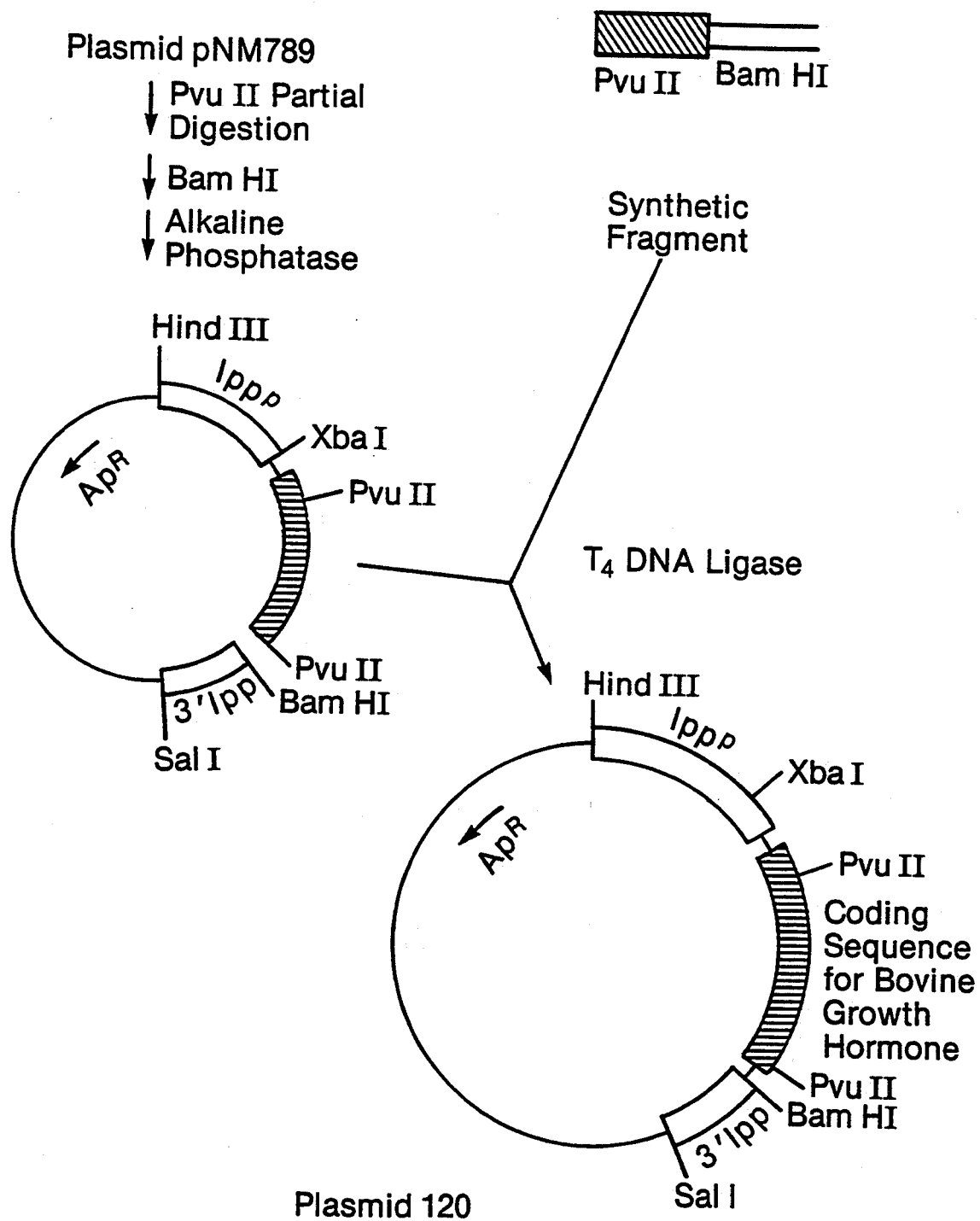
FIG. 8—a chart designating the construction of and a restriction site and function map of plasmid 120.

Plasmid pNM789 is obtained from the NRRL in E. coli K12 RV308/pNM789 under the accession number B-18216. A restriction site and function map of plasmid pNM789 is presented in FIG. 7 of the accompanying drawings. Plasmid pNM789 was partially digested with restriction enzyme PvuII, fully digested with restriction enzyme BamHI, then treated with alkaline phosphatase. Next, a new PvuII-BamHI linker was ligated into the digested, phosphatased vector pNM789 to form plasmid 120. A detailed description of the construction of plasmid 120 is presented in Example 7. A restriction site and function map of plasmid 120 is presented in FIG. 8 of the accompanying drawings.

Figure 9:
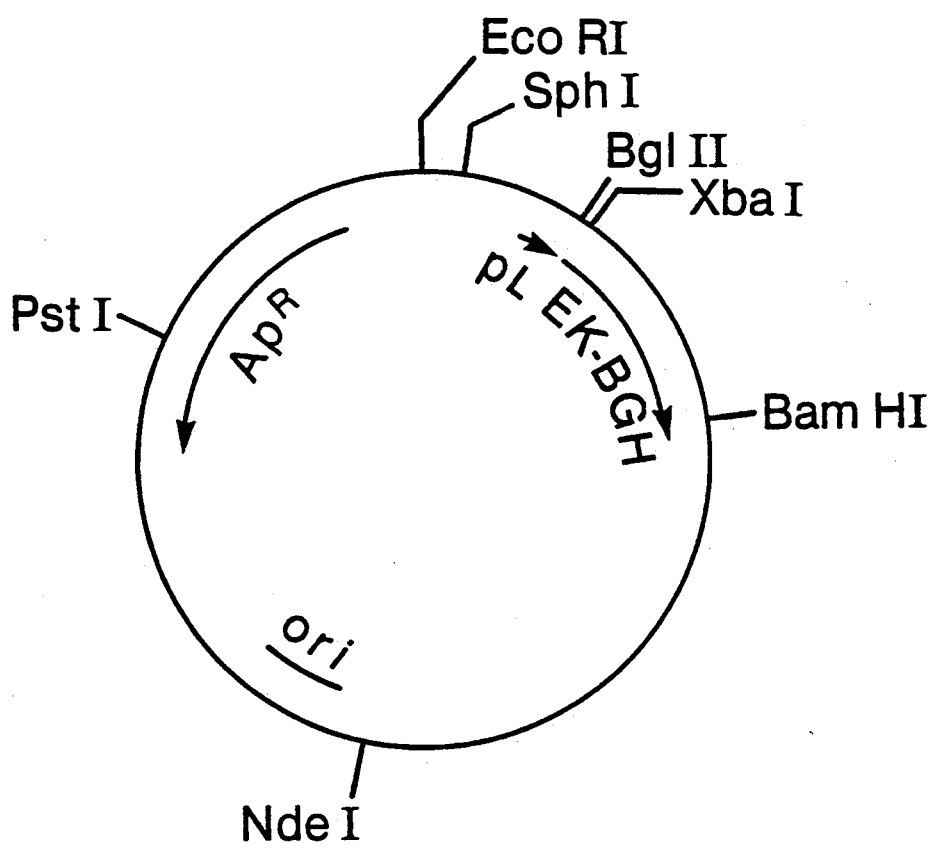
FIG. 9—the restriction site and function map of plasmid pL47.

Plasmid 120 was then totally digested with restriction enzymes XbaI and BamHI and the ~0.6 kb XbaI-BamHI EK-BGH-encoding restriction fragment was isolated. Plasmid pL32 was also digested with restriction enzymes XbaI and BamHI and the ~3.9 kb vector fragment was isolated. The ~0.6 kb XbaI-BamHI fragment of plasmid 120 was then ligated into the ~3.9 kb vector fragment of plasmid pL32 to form plasmid pL47. A detailed description of the construction of plasmid pL47 is presented in Example 7. A restriction site and function map of plasmid pL47 is presented in FIG. 9 of the accompanying drawings.

Figure 10:
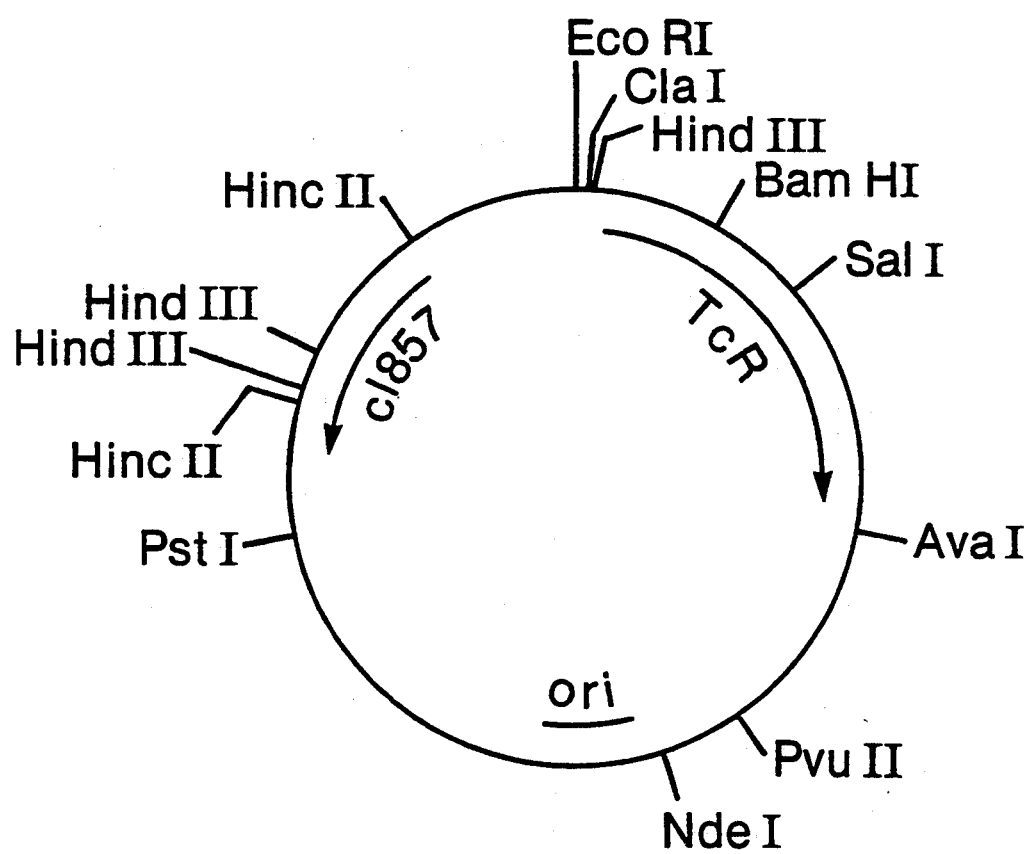
FIG. 10—the restriction site and function map of plasmid pPR12.
Figure 11:
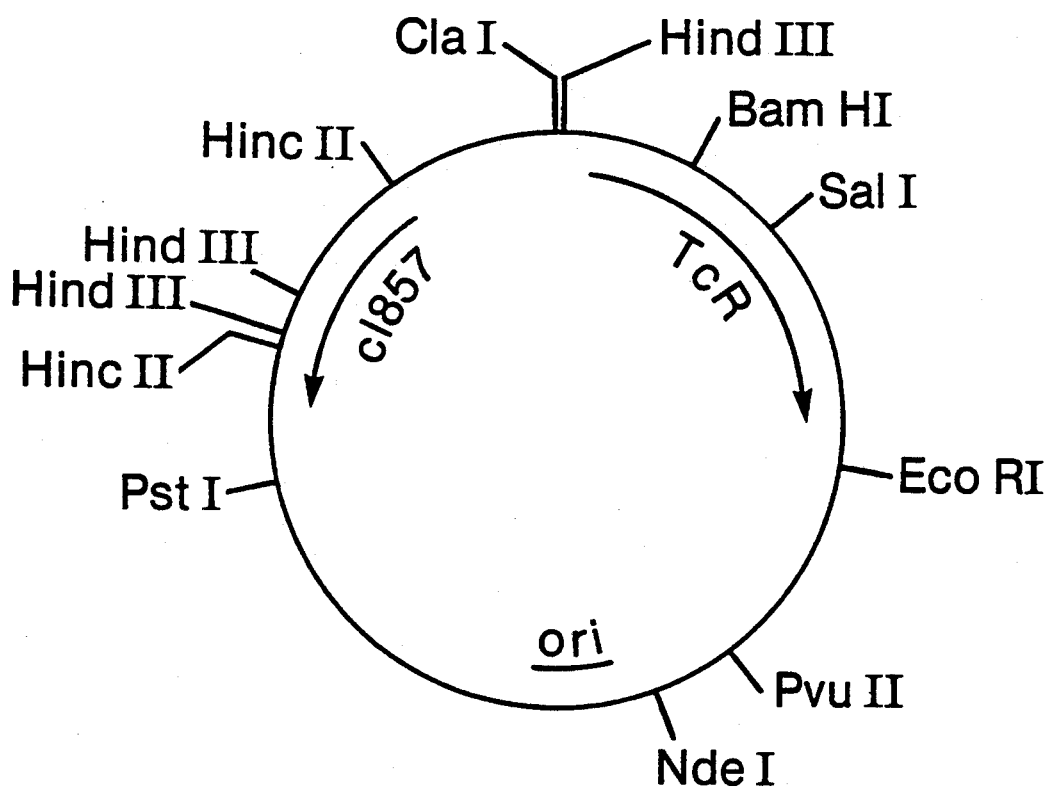
FIG. 11—the restriction site and function map of plasmid pPR12AR1.

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued Mar. 13, 1984. A restriction site and function map of plasmid pPR12 is presented in FIG. 10 of the accompanying drawings. The EcoRI site was removed from plasmid pPR12 by first totally digesting the plasmid with restriction enzyme EcoRI, followed by treatment with Klenow. The vector was then recircularized by ligation to form plasmid pBR12ΔR1. Plasmid pPR12ΔR1 was then digested with restriction enzyme AvaI and treated with Klenow. The AvaI-digested, Klenow treated pPR12ΔR1 was next ligated to EcoRI linkers, cut with restriction enzyme EcoRI, then recircularized to form plasmid pPR12AR1. A detailed description of the construction of plasmid pPR12AR1 is presented in Example 8. A restriction site and function map of plasmid pPR12AR1 is presented in FIG. 11 of the accompanying drawings.

Figure 12:
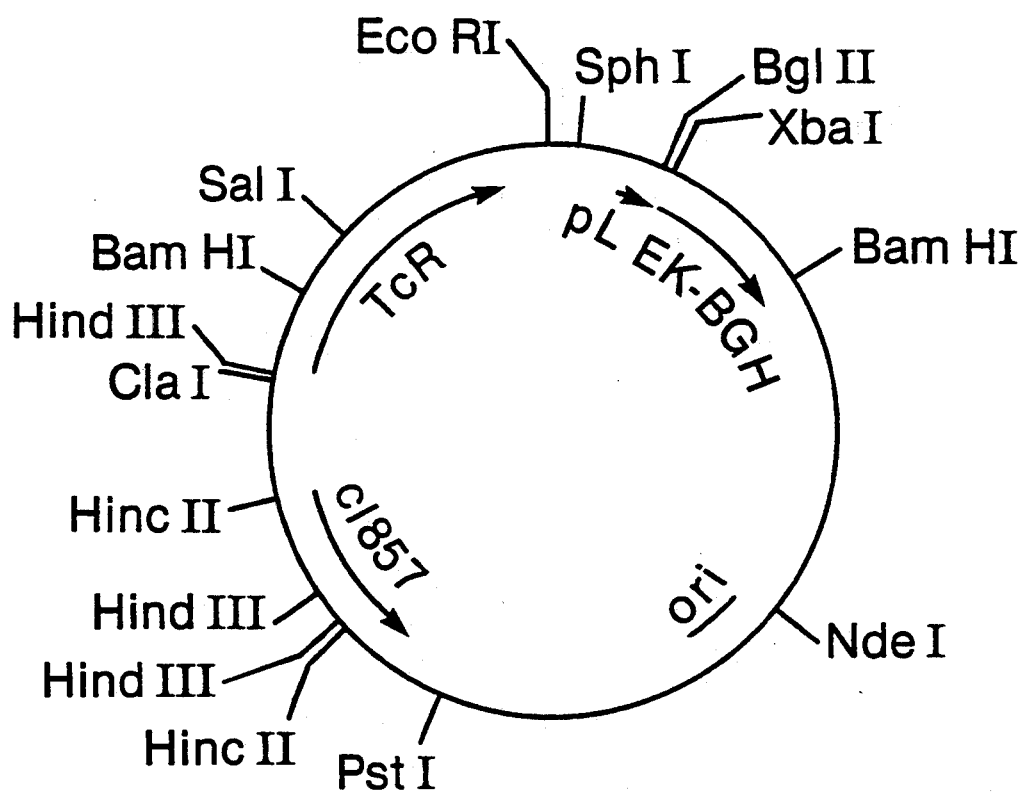
FIG. 12—the restriction site and function map of plasmid pL110.

The ~2.9 kb PstI-EcoRI restriction fragment of plasmid pPR12AR1 was isolated after the plasmid was first-digested with restriction enzymes PstI and EcoRI. Plasmid pL47 was digested with restriction enzymes PstI and BamHI and the ~2.7 kb PstI-BamHI restriction fragment was isolated. In a separate reaction, plasmid pL47 was digested with restriction enzymes EcoRI and BamHI and the ~1.03 kb EcoRI-BamHI fragment was isolated. The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to form plasmid pL110. A detailed description of the construction of plasmid pL110 is presented in Example 9. A restriction site and function map of plasmid pL110 is presented in FIG. 12 of the accompanying drawings.

Plasmid pL110 was cut with restriction enzyme NdeI, treated with Klenow, then recircularized to form plasmid pL110A. Plasmid pL110 was also cut with restriction enzymes HindIII and EcoRI and the tetracycline resistance-conferring fragment was isolated. This fragment was ligated to the ~7.25 kb HindIII to EcoRI restriction fragment of phage m13mp18 to form phage M13Tc3. Phage m13mp18 may be purchased from New England Biolabs. Single-stranded phage M13Tc3 was then isolated and an in Vitro mutagenesis reaction was performed to change the nucleotide C to an A in the BamHI site of the tetracycline gene. This does not alter the amino acid composition of the tetracycline resistance-conferring protein but eliminates the BamHI site. The newly mutagenized plasmid was transformed and a replicative form which lacked the BamHI site was selected and designated plasmid pL110B.

Plasmid pL110B was cut with restriction enzymes NheI and SalI, then the tetracycline resistance-conferring fragment was isolated. Plasmid pL110A was likewise cut with restriction enzymes NheI and SalI, then the large vector fragment was isolated. The tetracycline-resistance conferring fragment of plasmid pL110B was then ligated into the NheI-SalI cut vector fragment of pL110A to form plasmid pL110C. A detailed description of the construction of pL110C is presented in Example 10. A detailed construction protocol and restriction site and function map of plasmid pL110C is presented in FIG. 13 of the accompanying drawings.

Figure 18:
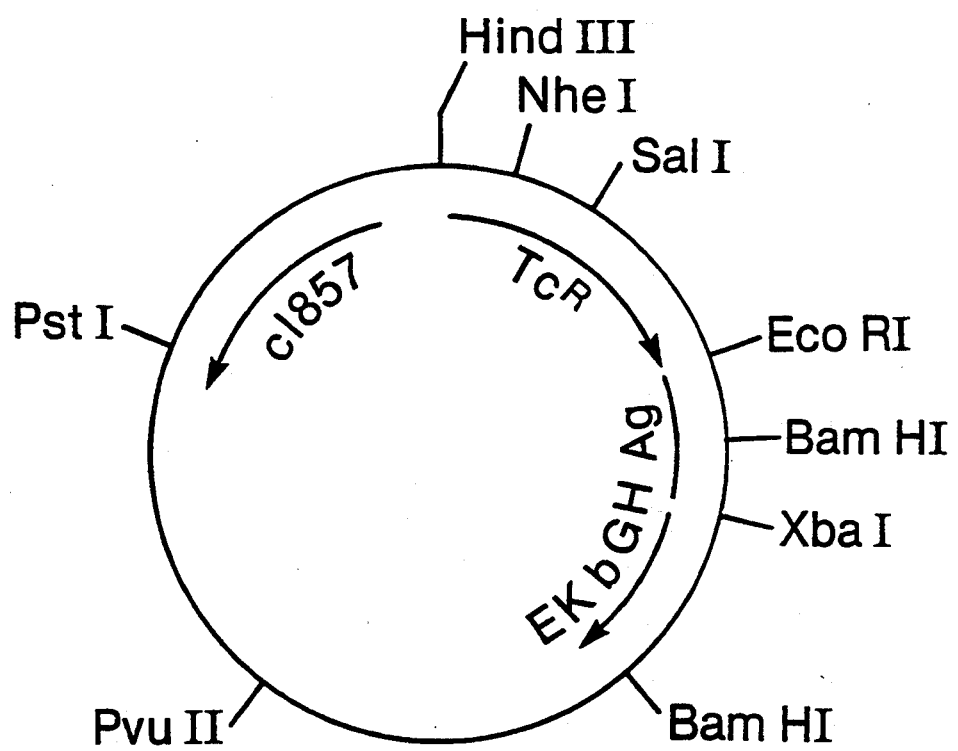
FIG. 18—the restriction site and function map of plasmid pLKSA-B.

Plasmid pGAG1317 was cut with restriction enzyme ApaI, then treated with alkaline phosphatase. Linkers were ligated onto the molecule which comprise the DNA that encodes the first six amino acid residues of KSA plus an added methionine residue. These linkers also comprise an XbaI restriction site at the 5' end. The DNA was then digested with XbaI and EcoRI, and the ~500 kb XbaI-EcoRI restriction fragment was isolated. Plasmid pL110C was digested with EcoRI and XbaI and the large vector fragment was isolated. The ~500 kb EcoRI-XbaI fragment of pGAG1317 was then ligated into the EcoRI-XbaI vector fragment of pL110C to form plasmid pLKSA-B. A detailed description of the construction of plasmid pLKSA-B is presented in Example 12. A restriction site and function map of plasmid pLKSA-B is presented in FIG. 18 of the accompanying drawings.

Figure 19:
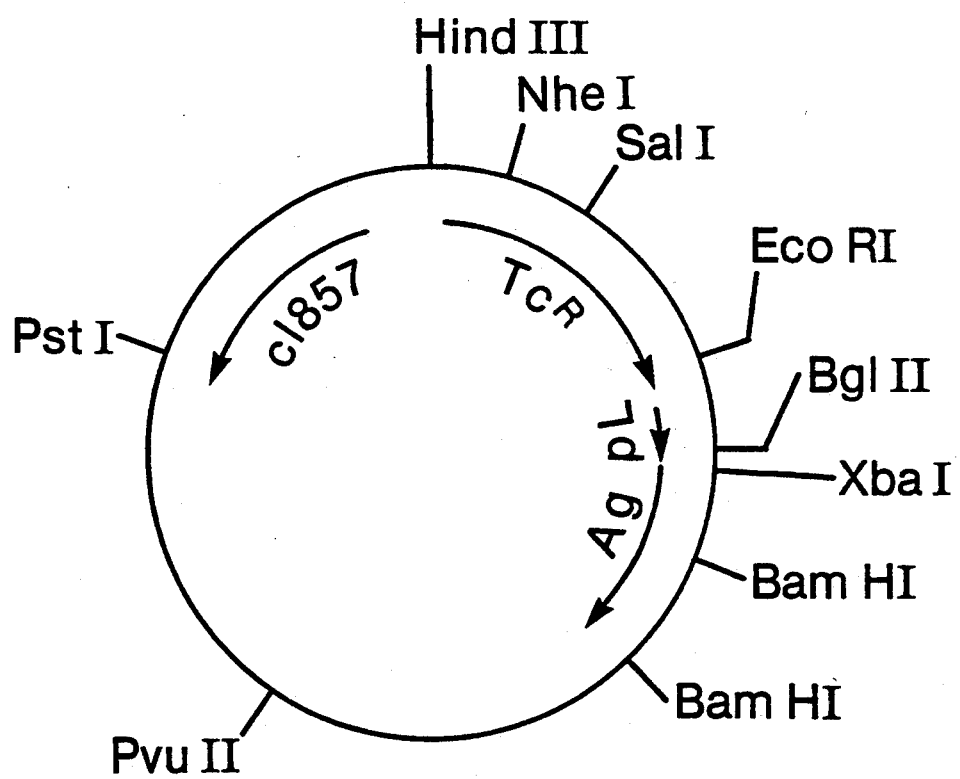
FIG. 19—the restriction site and function map of plasmid pLKSA.

Plasmid pLKSA-B was digested with restriction enzyme EcoRI, then dephosphorylated with alkaline phosphatase. EcoRI-BamHI linkers were then ligated onto the EcoRI-cut molecule. These linkers also comprise DNA encoding the eight amino acid residues between the EcoRI site and the transmembrane region of KSA plus a transcriptional "stop" codon. This plasmid was then cut with restriction enzyme XbaI and the XbaI-BamHI KSA-encoding fragment was isolated. Next, pL110C was cut with restriction enzymes XbaI and BamHI and the large vector fragment was isolated. The KSA-encoding XbaI-BamHI restriction fragment of pLKSA-B was then ligated into the XbaI-BamHI vector fragment of plasmid pL110C to form plasmid pLKSA. A detailed description of the construction of plasmid pLKSA is presented in Example 12. A restriction site and function map of plasmid pLKSA is presented in FIG. 19 of the accompanying drawings.

Plasmid pLKSA comprises the tetracycline resistance-conferring gene, the temperature sensitive cI857 repressor gene, the hybrid pL/lpp promoter system and amino acid residues 82-265 of the nascent prepro KSA. Amino acid residues 82-265 of the nascent prepro KSA comprise the nascent amino acid antigen structure that is found on the cell surface of adenocarcinoma cells such as UCLA-P3 cells. Expression of KSA in *E. coli* is in no way limited to the use of a particular promoter, since the choice of a specific promoter is not critical to the operability of the present invention. Promoters which can be substituted for the previously exemplified pL promoter include, but are not limited to, the *E. coli* lactose (lac), the *E. coli* trp, bacteriophage λP$_L$O$_L$, and bacteriophage λ P$_R$O$_R$ promoters. In addition, one or more promoters can be used in tandem, such as, for example, the trp and lac promoters, or hybrid promoters, such as the tac promoter, can be used to drive expression of the KSA structural gene. All of the aforementioned promoters have been previously characterized, are well known in the art, and can be constructed either synthetically or from known plasmids.

Skilled artisans will recognize that the present invention is not limited to the use of any given replicon-containing plasmid for expression of KSA in *E. coli*. Many replicons, such as those from pBR322, pBR328, pACYC184, and the like, are known in the art and are suitable for the construction of recombinant DNA cloning and expression vectors designed to drive expression of the KSA-encoding DNA compounds of the present invention. Neither is the present invention limited to the actual selectable marker exemplified on the plasmids exemplified herein. A wide variety of selectable markers exist, both for eukaryotic and prokaryotic host cells, that are suitable for use on a recombinant DNA cloning or expression vector comprising a DNA compound (or sequence) of the present invention.

Many modifications and variations of the present illustrative DNA sequences and plasmids are possible. For example, the degeneracy of the genetic code allows for the substitution of nucleotides throughout polypeptide coding regions as well as for the substitution of the

translational stop signals for the

translational stop signal specifically exemplified. Such sequences can be deduced from the now-known amino acid or DNA sequence of KSA and can be constructed by following conventional synthetic procedures. Such synthetic methods can be carried out in substantial accordance with the procedures of Itakura et al., 1977 Science 198:1056 and Crea et al., 1978, Proc. Nat. Acad. Sci. USA 75:5765. In addition, synthetic genes and linkers can be synthesized either by using a Systec 1450A DNA synthesizer (Systec Inc., 3816 Chandler Drive, Minneapolis, Minn.) or an ABS 380A DNA synthesizer (Applied Biosystems, Inc., 850 Lincoln Center Drive, Foster City, Calif. 94404). Many other DNA synthesizing instruments are known in the art and can be used to make synthetic DNA fragments. Therefore, the present invention is in no way limited to the DNA sequences and plasmids specifically exemplified.

The prokaryotic expression vectors and method of this invention can be applied to a wide range of host organisms, especially Gram-negative prokaryotic organisms such as *Escherichia coli, E. coli* K12, *E. coli* K12 RV308, *E. coli* K12 HB101, *E. coli* K12 C600, *E. coli* K12 RR1, *E. coli* K12 RR1ΔM15, *E. coli* K12 MM294, *E. Coli* K12 DH5, and the like. Although all of the embodiments of the present invention are useful, some of the vectors and transformants are preferred. A preferred transformant is *E. coli* K12 RV308/pLKSA.

Those skilled in the art will recognize that the expression vectors of this invention are used to transform either eukaryotic or prokaryotic host cells, such that a polypeptide with nascent chain KSA structure is expressed by the host cell. If the host cell is transformed with a vector comprising a promoter that functions in the host cell and drives transcription of the nascent KSA structural gene, and if the host cell possesses the cellular machinery with which to process the signal peptide, mature KSA can be found on the surface of such cells. Under other expression conditions, such as when plasmid pLKSA is in *E. coli* RV308, the KSA must be isolated from the host cell.

As stated above, KSA produced by recombinant methodology will have a profound effect upon the diagnosis, prognosis, treatment and study of cancers of epithelial origin. Furthermore, because KSA is also expressed on a subset of normal human epithelial cells, the amino acid and nucleotide sequences disclosed will be useful in understanding the role of such cell surface antigens in normal tissue differentiation, development and non-malignant disease states. The KSA gene (or subfragments thereof) can be used to probe DNA libraries derived from a wide range of cell types, to find other related genes or variants thereof. These new antigen genes can then be used to construct novel antibodies in a further attempt to combat cancer.

Monoclonal antibody KS 1/4 has been shown to be an effective agent for the diagnosis, prognosis and treatment of cancer by Bumol in Reisfeld, R. A. and Sell, S. eds. Monoclonal Antibodies and Cancer Therapy. New York: Alan R. Liss, Inc., 1985, 257–259. Spearman et al., 1987, J. Pharmacol. and Exp. Therapeutics 241:695–703, the teaching of which is herein incorporated by reference, disclosed the use of a monoclonal antibody-vinca alkaloid conjugate in the localization and treatment of tumors. This KS 1/4-DAVLB (4-desacetylvinblastine) conjugate was also responsible for tumor growth suppression as disclosed by Bumol et al. in Ceriani, R. L. ed. Immunological Approaches to the Diagnosis and Therapy of Breast Cancer. New York and London: Plenum Press; 1987, 205–215, the teaching of which is herein incorporated by reference. In light of these teachings recombinant KSA will be useful in modifying the affinity of KS 1/4. Following binding of KS 1/4 to the cell-surface soluable portion of KSA, X-Ray crystallographic analysis will demonstrate which amino acid residues of the antigen appear in close proximity to certain amino acid residues of KS 1/4. By using protein engineering techniques, KS 1/4 can then be modified to provide negative residues near positive residues on the antigen. Such "engineered" antibodies will then display increased affinity to cell surface KSA in cancer patients. In an analogous manner, these protein engineering techniques can be used to create low affinity KS 1/4 derivatives also.

Skilled artisans will recognize that such "high-affinity" antibodies, made possible only by the sequences of the present invention, will have increased efficacy when compared to normal KS 1/4. Because the newly engineered antibodies more tightly bind the KSA, fewer molecules will need to be administered to patients. This decreases the total amount of circulating antibody in the patients' system and thereby decreases the probability that such antibodies will bind to low-epitope cells, such as normal colon cells. Adenocarcinoma cells, on the other hand, which display a high epitope density of the antigen, will be more apt to be recognized by the novel antibodies.

Furthermore, recombinant KSA and its derivatives can be isolated from any cell in which they are expressed using solubilization procedures that are well known in the art. Kahan, in "Methods of Cancer Research," Vol. IX, Busch, ed., p. 283–338 (Academic Press, New York, 1973) describes a variety of extraction techniques, as does Graham, in "New Techniques in Biophysics and Cell Biology," Vol. 2, Pain et al., eds., pp. 1–42 (Wiley, London 1975). The antigen fractions can then be used to create novel antibodies according to the teaching of Köhler and Milstein, 1975, Nature 256:495–497 or Goldenberg, U.S. Pat. No. 4,444,744. These KS 1/4 "sister" antibodies, which can be isolated due to their specific reactivity to recombinant KSA or UCLA-P3 cells, are also useful for the diagnosis and treatment of disease states.

Recombinant KSA and its derivatives can also be used to raise polyclonal antibodies which react with tumor cells. Occasionally, such polyclonal antibodies will demonstrate an increased reactivity to tumor surface markers. Polyclonal antibodies are raised by methods which are well known in the art. An animal is challenged with the antigen or any subunit thereof, then, following an appropriate amount of time in which the animal's immune system produces antibodies against the antigen, the animal is bled. The antibodies are then isolated according to well known techniques such as those disclosed in "Immunodiagnosis of Cancer," Herberman et al., Eds. (Marcel Dekker, Inc., New York and Basel, 1979) and "Tumor Markers," Sell, Ed. (Humana Press, Clifton, N.J., 1980). These antibodies are then used in immunological assays to test the presence of adenocarcinoma cells in tissue.

Recombinant KSA and its derivatives can also be prepared to offer large quantities of defined antigen for the standardization of analytical methodology. For example, functional immunoassays can be developed to monitor fermentation and production of KS 1/4 antibody or newly developed derivatives thereof. Affinity chromatography, using recombinant KSA, will greatly simplify the purification of monoclonal antibody KS 1/4. The recombinant KSA and its derivatives can also be used in the purification, formulation analysis and stability studies of various monoclonal antibody based products. Recombinant KSA can also be used for development of potential anti-adenocarcinoma vaccines.

The following examples further illustrate the invention disclosed herein. The examples describe the procedures for the construction of the present invention, and explanations of the procedures as provided where appropriate.

EXAMPLE 1

Isolation of Plasmid pKC283

Lyophils of E. coli K12 BE1201/pKC283 are obtained from the Northern Regional Research Laboratory, Peoria, Ill. 61604, under the accession number NRRL B-15830. The lyophils are decanted into tubes containing 10 ml LB medium (10 g Bacto-tryptone, 5 g Bacto-yeast extract, and 10 g NaCl per liter; pH is adjusted to 7.5) and incubated two hours at 32° C., at which time the cultures are made 50 μg/ml in ampicillin and then incubated at 32° C. overnight. The E. coli K12 BE1201/pKC283 cells were cultured at 32° C., because the cells comprise a temperature-sensitive cI repressor gene integrated into the cellular DNA. When cells that comprise a wild-type lambda pL repressor gene or do not comprise a lambda pL promoter are utilized in this plasmid isolation procedure, as described in subsequent Examples herein, the temperature of incubation is 37° C.

A small portion of the overnight culture is placed on LB-agar (LB medium with 15 g/l Bacto-agar) plates containing 50 μg/ml ampicillin in a manner so as to obtain a single colony isolate of E. coli K12 BE1201/pKC283. The single colony obtained was inoculated into 10 ml of LB medium containing 50 μg/ml ampicillin and incubated overnight at 32° C. with vigorous shaking. The 10 ml overnight culture was inoculated into 500 ml LB medium containing 50 μg/ml ampicillin and incubated at 32° C. with vigorous shaking until the culture reached stationary phase.

The following procedure is adapted from Maniatis et al., 1982, Molecular Cloning (Cold Spring Harbor Laboratory).

The cells were harvested by centrifugation at 4000 g for 10 minutes at 4° C., and the supernatant was discarded. The cell pellet was washed in 100 ml of ice-cold STE buffer (0.1M NaCl; 10 mM Tris-HCl, pH 7.8; and 1 mM EDTA). After washing, the cell pellet was resuspended in 10 ml of Solution 1 (50 mM glucose; 25 mM Tris-HCl, pH 8.0; and 10 mM EDTA) containing 5 mg/ml lysozyme and left at room temperature for 10 minutes. Twenty ml of Solution 2 (0.2 N NaOH and 1% SDS) were then added to the lysozyme-treated cells, and the solution was gently mixed by inversion. The mixture was incubated on ice for 10 minutes.

Fifteen ml of ice-cold 5M potassium acetate, pH 4.8, were added to the lysed-cell mixture and the solution mixed by inversion. The solution was incubated on ice for 10 minutes. The 5M potassium acetate solution was prepared by adding 11.5 ml of glacial acetic acid to 28.5 ml of water and 60 ml of 5M potassium acetate; the resulting solution is 3M with respect to potassium and 5M with respect to acetate..

The lysed cell mixture was centrifuged in a Beckman SW27 (or its equivalent) at 20,000 rpm for 20 minutes at 4° C. The cell DNA and-debris formed a pellet on the bottom of the tube. About 36 ml of supernatant were recovered, and 0.6 volumes of isopropanol were added, mixed, and the resulting solution left at room temperature for 15 minutes. The plasmid DNA was collected by centrifugation at 12,000 g for 30 minutes at room temperature. The supernatant was discarded, and the DNA pellet was washed with 70% ethanol at room temperature. The ethanol wash was decanted, and the pellet was dried in a vacuum desiccator. The pellet was then resuspended in 8 ml of TE buffer (10 mM Tris-HCl, pH 8.0, and 1 mM EDTA).

Eight grams of CsCl were added to the DNA solution. About 0.8 ml of a 10 mg/ml solution of ethidium bromide in water were added for each 10 ml of CsCl-DNA solution. The final density of the solution was about 1.55 g/ml, and the ethidium bromide concentraton was about 600 $\mu$g/ml. The solution was transferred to a Beckman Type 50 centrifuge tube, filled to the top with paraffin oil, sealed, and centrifuged at 45,000 rpm for 24 hours at 20° C. After centrifugation, two bands of DNA were visible in ordinary light. After removing the cap from the tube, the lower DNA band was removed by using a syringe with a #21 hypodermic needle inserted through the side of the centrifuge tube.

The ethidium bromide was removed by several extractions with water-saturated 1-butanol. The CsCl was removed by dialysis against TE buffer. After extractions with buffered phenol and then chloroform, the DNA was precipitated, washed with 70% ethanol, and dried. About 1 mg of plasmid pKC283 was obtained and stored at 4° C. in TE buffer at a concentration of about 1 $\mu$g/$\mu$l. A restriction site and function map of plasmid pKC283 is presented in FIG. 1 of the accompanying drawings.

EXAMPLE 2

Construction of Plasmid pKC283PX

About 10 $\mu$l of the plasmid pKC283 DNA prepared in Example 1 were mixed with 20 $\mu$l 10 X medium-salt restriction buffer (500 mM NaCl; 100 mM Tris-HCl, pH 7.5; 100 mM MgCl$_2$; and 10 mM DTT), 20 $\mu$l 1 mg/ml BSA, 5 $\mu$l restriction enzyme PvuII (~50 Units, as defined by Bethesda Research Laboratories (BRL), from which all restriction enzymes used herein were obtained), and 145 $\mu$l of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 $\mu$l of TE buffer.

About 600 picomoles (pM) of XhoI linkers (5'-CCTCGAGG-3') were kinased in a mixture containing 10 $\mu$l 5 X Kinase Buffer (300 mM Tris-HCl, pH 7.8; 50 mM MgCl$_2$; and 25 mM DTT), 5 $\mu$l 5 mM ATP, 24 $\mu$l H$_2$O, 0.5 $\mu$l of T4 polynucleotide kinase (about 2.5 units as defined by P-L Biochemicals), 5 $\mu$l 1 mg/ml BSA, and 5 $\mu$l of 10 mM spermidine by incubating the mixture at 37° C. for 30 minutes.

About 12.5 $\mu$l of the kinased XhoI linkers were added to the 5 $\mu$l of PvuII-digested plasmid pKC283 DNA, and then 2.5 $\mu$l of 10 X ligase buffer (300 mM Tris-HCl, pH 7.6; 100 mM MgCl$_2$; and 50 mM DTT), 2.5 $\mu$l of 1 mg/ml BSA, 7 $\mu$l of 5 mM ATP, 2.5 $\mu$l (about 2.5 units as defined by P-L Biochemicals) of T4 DNA ligase, 2.5 $\mu$l of 10 mM spermidine, and 3 $\mu$l of water were added to the DNA. The resulting ligation reaction was incubated at 4° C. overnight. After the ligation reaction, the reaction mixture was adjusted to have the composition of high-salt buffer (0.1M NaCl; 0.05M Tris-HCl, pH 7.5; 10.0 mM MgCl$_2$; and 1 mM DTT). About 10 $\mu$l (100 units) of restriction enzyme XhoI were added to the mixture, and the resulting reaction was incubated at 37° C. for 2 hours.

The reaction was terminated, and the XhoI-digested DNA was precipitated, resuspended, and ligated as described above, except that no XhoI linkers were added to the ligation mixture. The ligated DNA constituted the desired plasmid pKC283PX. A restriction site and function map of plasmid pKC283PX is presented in FIG. 2 of the accompanying drawings.

EXAMPLE 3

Construction of E. coli K12 MO($\lambda$+)/pKC283PX

E. coli K12 MO($\lambda$+) can be obtained from the Northern Regional Research Laboratories in lyophylized form under the accession number NRRL B-15993. E. coli K12 MO($\lambda$+) comprises the wild-type lambda pL cI repressor gene, so that transcription from the hybrid pL-lpp promoter of the present invention does not occur in E. coli K12 MO($\lambda$+) cells. The lyophils are reconstituted, single colonies of MO($\lambda$+) are isolated, and a 10 ml overnight culture of the MO($\lambda$+)cells is prepared in substantial accordance with the procedure of Example 1, except that the temperature of incubation is 37° C. and no ampicillin is used in the growth media.

Fifty $\mu$l of the overnight culture were used to inoculate 5 ml of LB media which also contained 10 mM MgSO$_4$ and 10 mM MgCl$_2$. The culture was incubated at 37° C. overnight with vigorous shaking. The following morning, the culture was diluted to 200 ml with LB media containing 10 mM MgSO$_4$ and 10 mM MgCl$_2$. The diluted culture was incubated at 37° C. with vigorous shaking until the absorbance at 550 nm (A$_{550}$) was about 0.5, which indicated a cell density of about $1 \times 10^8$ cells/ml. The culture was cooled for ten minutes in an ice-water bath, and the cells were then collected by centrifugation at 4000 g for 10 minutes at 4° C. The cell pellet was resuspended in 100 ml of cold 10 mM MgSO$_4$ and then immediately re-pelleted by centrifugation. The cell pellet was resuspended in 100 ml of 30 mM CaCl$_2$ and incubated on ice for 20 minutes.

The cells were again collected by centrifugation and resuspended in 10 ml of 30 mM CaCl$_2$. A one-half ml aliquot of the cells was added to the ligated DNA prepared in Example 2; the DNA had been made 30 mM in CaCl$_2$. The cell-DNA mixture was incubated on ice for one hour, heat-shocked at 42° C. for 90 seconds, and then chilled on ice for about two minutes. The cell-DNA mixture was diluted into 10 ml of LB media in 125 ml flasks and incubated at 37° C. for one hour. One hundred μl aliquots were plated on LB-agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in accordance with the procedure of Example 1, but the CsCl gradient step was omitted until the desired E. coli K12 MO(λ+)/pKC283PX transformants were identified. A restriction site and function map of plasmid pKC283PX is presented in FIG. 2 of the accompanying drawings.

EXAMPLE 4

Construction of E. coli K12 MO(λ+)/pKC283-L

Ten μg of plasmid pKC283PX DNA prepared in accordance with the procedure of Example 1 were dissolved in 20 μl of 10X high-salt buffer, 20 μl 1 mg/ml BSA, 5 μl (~50 units) restriction enzyme BglII, 5 μl (~50 units) restriction enzyme XhoI, and 150 μl of water, and the resulting reaction was incubated at 37° C. for two hours. The reaction was stopped, and after precipitating the BglII-XhoI digested DNA, the DNA was resuspended in 5 μl of TE buffer.

A DNA linker with single-stranded DNA ends characteristic of BglII and XhoI restriction enzyme cleavage was synthesized and kinased. The linker was kinased in substantial accordance with the procedure of Example 2. The DNA linker had the following structure:

The linker depicted above was synthesized from single-stranded deoxyoligonucleotides by procedures well known in the art. The single-stranded deoxyoligonucleotides can be synthesized with commercially available instruments, such as the 380A DNA Synthesizer marketed by Applied Biosystems (850 Lincoln Centre Drive, Foster City, Calif. 94404), which utilizes phosphoramidite chemistry. Other procedures for synthesizing DNA are also known in the art. The conventional modified phosphotriester method of synthesizing single stranded DNA is described in Itakura et al., 1977, Science 198:1056 and in Crea et al., 1978, Proc. Nat. Acad. Sci. USA 75:5765. In addition, an especially preferred method of synthesizing DNA is disclosed in Hsiung et al., 1983, Nucleic Acid Research 11:3227 and Narang et al., 1980, Methods in Enzymology 68:90.

The linker and BglII-XhoI-digested plasmid pKC283PX were ligated in substantial accordance with the procedure of Example 2. The ligated DNA constituted the desired plasmid pKC283-L. A restriction site and function map of plasmid pKC283-L is presented in FIG. 3 of the accompanying drawings. The plasmid pKC283-L DNA was used to transform E. coli K12 MO(λ+) and the resulting E. coli K12 MO(λ+)/pKC283-L transformants were identified in substantial accordance with the procedure of Example 3.

EXAMPLE 5

Construction of E. coli K12 MO(λ+)/pKC283-LB

About 10 μg of plasmid pKC283-L DNA, prepared in substantial accordance with the procedures of Example 1, were dissolved in 20 μl 10X high-salt buffer, 20 μl 1 mg/ml BSA, 5 μl (~50 units) restriction enzyme XhoI, and 155 μl of H$_2$O, and the resulting reaction was incubated at 37° C. for two hours. The XhoI-digested plasmid pKC283-L DNA was then precipitated from the reaction mixture by the addition of three volumes of 95% ethanol and one-tenth volume of 3M sodium acetate, incubation in a dry ice-ethanol bath for five minutes, and centrifugation. The resulting DNA pellet was washed with 70% ethanol, dried, and resuspended in 2 μl 10X nick-translation buffer (0.5M Tris-HCl, pH 7.2; 0.1M MgSO$_4$; and 1 mM DTT), 1 μl of a solution 2 mM in each of the deoxynucleotide triphosphates, 15 μl of H$_2$O, 1 μl (~6 units as defined by P-L Biochemicals) of Klenow, which is the large fragment of E. coli DNA polymerase I, and 1 μl of 1 mg/ml BSA. The resulting reaction was incubated at 25° C. for 30 minutes; the reaction was stopped by incubating the solution at 70° C. for five minutes.

BamHI linkers (5'-CGGGATCCCG-3') were kinased and ligated to the XhoI-digested, Klenow-treated plasmid pKC283-L DNA in substantial accordance with the procedure of Example 2. After the ligation reaction, the DNA was digested with about 100 units of BamHI for about 2 hours at 37° C. in high-salt buffer. After the BamHI digestion, the DNA was prepared for ligation in substantial accordance with the procedure of Example 2.

The ~5.9 kb BamHI restriction fragment was circularized by ligation and transformed into E. coli K12 MO(λ+) in substantial accordance with the procedures of Examples 2 and 3. The E. coli K12 MO(λ$^{30}$)/pKC283-LB transformants were identified, and then plasmid pKC283-LB DNA was prepared in substantial accordance with the procedure of Example 1. A restriction site and function map of plasmid pKC283-LB is presented in FIG. 4 of the accompanying drawings.

EXAMPLE 6

Construction of E. coli K12 MO(λ+)/pL32

About 10 μg of plasmid pKC283PX were digested with restriction enzyme SalI in high-salt buffer, treated with Klenow, and ligated to EcoRI linkers (5'-GAGGAATTCCTC-3') in substantial accordance with the procedure of Example 5, with the exception of the starting plasmid, restriction enzymes, and linkers used. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform E. coli K12 MO(λ+) in substantial accordance with the procedure of Example 3. After the E. coli K12 MO(λ+)/pKC283PRS transformants were identified, plasmid pKC283PRS DNA was prepared in substantial accordance with the procedure of Example 1. A restriction site and function map of plasmid pKC283PRS is presented in FIG. 5 of the accompanying drawings.

About 10 μg of plasmid pKC283PRS were digested in 200 μl of high-salt buffer with about 50 units each of restriction enzymes PstI and SphI. After incubating the reaction at 37° C. for about 2 hours, the reaction mixture was electrophoresed on a 0.6% low-gelling-temperature agarose (FMC Corporation, Marine Colloids Division, Rockland, Me. 04841) gel for 2–3 hours at ~130 V and ~75 mA in Tris-Acetate buffer.

The gel was stained in a dilute solution of ethidium bromide, and the band of DNA constituting the ~0.85 kb PstI-SphI restriction fragment, which was visualized with long-wave UV light, was cut from the gel in a small segment. The volume of the segment was determined by weight and density of the segment, and an equal volume of 10 mM Tris-HCl, pH 7.6, was added to the tube containing the segment. The segment was then melted by incubation at 72° C. About 1 ug of the ~0.85 kb PstI-SphI restriction fragment of plasmid pKC283PRS was obtained in a volume of about 100 μl. In an analogous manner, plasmid pKC283-LB was digested with restriction enzymes pstI and SphI, and the resulting ~3.0 kb restriction fragment was isolated by agarose gel electrophoresis and prepared for ligation.

The ~0.85 kb PstI-SphI restriction fragment of plasmid pKC283PRS was ligated to the ~3.0 kb PstI-SphI restriction fragment of plasmid pKC283-LB in substantial accordance with the procedure of Example 2. The ligated DNA constituted the desired plasmid pL32. A restriction site and function map of plasmid pL32 is presented in FIG. 6 of the accompanying drawings. Plasmid pL32 was transformed into E. coli K12 MO(λ+) cells in substantial accordance with the procedure of Example 3. Plasmid pL32 DNA was prepared from the E. coli K12 MO(λ+)/pL32 transformants in substantial accordance with the procedure of Example 1. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together. Alternatively, plasmid pL32 may be constructed by carrying out the SalI-EcoRI excision and ligation of the first paragraph of this Example upon plasmid pKC283-LB.

EXAMPLE 7 construction of E. coli K12 MO(λ+)/pL47

E. coli K12 RV308/pNM789 can be obtained from the Northern Regional Research Laboratories in lyophilized form under the accession number NRRL B-18216. A restriction site and function map of pNM789 is presented in FIG. 7 of the accompanying drawings. Plasmid DNA is extracted from the culture in substantial accordance with the teaching of Example 1, except that the temperature of incubation is 37° C. Ten micrograms of pNM789 are suspended in 200 μl PvuII buffer (50 mM Tris-HCl (pH 7.5), 60 mM NaCl and 6 mM MgCl$_2$). One unit of PvuII is added and the reaction mix is incubated for 5 minutes at 37° C. The enzyme is inactivated by heating 10 minutes at 65° C. 30 μl of 10X BamHI buffer (200 mM Tris-HCl (pH 8.0), 1M NaCl and 70 mM MgCl$_2$), 70 μl H$_2$O and 10 units of BamHI are next added and the reaction is incubated for 1 hour at 37° C. This is followed by the addition of 5 units of alkaline phosphatase and incubation for 1 hour at 65° C. The DNA fragments are separated on a 1 percent agarose gel, and a DNA fragment (FIG. 8) the size of a single cut fragment is purified.

A DNA linker with a blunt end and a BamHI end is synthesized in substantial accordance with the teaching of Example 4. This linker (shown at 118 in FIG. 8) has the following structure:

```
5'-CTGTGCCTTCTAG-3'
   |||||||||||||
3'-GACACGGAAGATCCTAG-5'
```

The linker is kinased and ligated into the BamHI-PvuII digested plasmid pNM789 in substantial accordance with the teaching of Example 2. This ligation mixture is used to transform E. coli K12 RV308 cells and plasmid isolation is performed upon these transformants in substantial accordance with the teaching of Example 3. Several plasmids are selected which contain the appropriate size PvuII fragment (494bp) and XbaI-BamHI fragment (628bp). The sequence of at least two of these is determined by sequencing from the BamHI site toward the unique SmaI site and one clone is selected with the desired sequence. This intermediate plasmid is designated plasmid 120. A schematic outline of this procedure and a restriction site and function map of plasmid 120 is presented in FIG. 8 of the accompanying drawings.

To isolate the EK-BGH-encoding DNA, about 10 μg of plasmid 120 were digested in 200 μl of high-salt buffer containing about 50 units each of restriction enzymes XbaI and BamHI. The digestion products were separated by agarose gel electrophoresis, and the ~0.6 kb XbaI-BamHI restriction fragment which encodes EK-BGH was isolated and prepared for ligation in substantial accordance with the procedure of Example 6.

Plasmid pL32 was also digested with restriction enzymes XbaI and BamHI, and the ~3.9 kb restriction fragment was isolated and prepared for ligation. The ~3.9 kb XbaI-BamHI restriction fragment of plasmid pL32 was ligated to the ~0.6 kb XbaI-BamHI restriction fragment of plasmid 120 in substantial accordance with the procedure of Example 2 to yield plasmid pL47. A restriction site and function map of plasmid pL47 is presented in FIG. 9 of the accompanying drawings. Plasmid pL47 was transformed into E. coli K12 MO(λ+) in substantial accordance with the procedure of Example 3, and the E. coli K12 MO(λ+)/pL47 transformants were identified. Plasmid pL47 DNA was prepared from the transformants in substantial accordance with the procedures of Example 1.

EXAMPLE 8

Construction of E. coli K12 RV308/pPR12AR1

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued Mar. 13, 1984. A restriction site and function map of plasmid pPR12 is presented in FIG. 10 of the accompanying drawings.

About 10 μg of plasmid pPR12 were digested with about 50 units of restriction enzyme EcoRI in 200 μl of high-salt buffer at 37° C. for two hours. The EcoRI-digested plasmid pPR12 DNA was precipitated and treated with Klenow in substantial accordance with the procedure of Example 5. After the Klenow reaction, the EcoRI-digested, Klenow-treated plasmid pPR12 DNA was recircularized by ligation in substantial accordance with the procedure of Example 2. The ligated DNA, which constituted the desired plasmid pPR12ΔR1, was used to transform *E. coli* K12 RV308 in substantial accordance with the procedure of Example 3, except that selection was based on tetracycline (5 μg/ml) resistance, not ampicillin resistance. *E. coli* K12 RV308 is available from the NRRL under the accession number NRRL B-15624. After the *E. coli* K12 RV308/pPR12ΔR1 transformants were identified, plasmid pPR12ΔR1 DNA was prepared from the transformants in substantial accordance with the procedure of Example 1.

About 10 μg of plasmid pPR12ΔR1 were digested with about 50 units of restriction enzyme AvaI in 200 μl of medium-salt buffer at 37° C. for 2 hours. The AvaI-digested plasmid pPR12ΔR1 DNA was precipitated and treated with Klenow in substantial accordance with the procedure of Example 5. After the Klenow reaction, the AvaI-digested, Klenow-treated plasmid pPR12ΔR1 DNA was ligated to EcoR1 linkers (5'-GAGGAATTCCTC-3') in substantial accordance with the procedure of Example 2. After the linker ligation, the DNA was precipitated and then resuspended in about 200 μl of high-salt buffer containing about 50 units of restriction enzyme EcoR1. The resulting reaction was incubated at 37° C. for about 2 hours. After the EcoR1 digestion, the reaction mixture was loaded onto an agarose gel, and the ~5.1 kb EcoR1 restriction fragment was purified in substantial accordance with the procedure of Example 6. The ~5.1 kb EcoR1 restriction fragment was recircularized by ligation in substantial accordance with the procedure of Example 2. The ligated DNA constituted the desired plasmid pPR12AR1. The plasmid pPR12AR1 DNA was transformed into *E. coli* K12 RV308 in substantial accordance with the procedure of Example 3, except that selection was based on tetracycline resistance, not ampicillin resistance. After identifying the *E. coli* K12 RV308/pPR12AR1 transformants, plasmid pPR12AR1 DNA was prepared in substantial accordance with the procedure of Example 1. A restriction site and function map of plasmid pPR12AR1 is presented in FIG. 11 of the accompanying drawings.

EXAMPLE 9

Construction of *E. coli* K12 RV308/pL110

About 10 μg of plasmid pPR12AR1 DNA were suspended in about 200 ml of high-salt buffer containing about 50 units each of restriction enzymes PstI and EcoRI, and the digestion reaction was incubated at 37° C. for about 2 hours. The reaction mixture was then loaded onto an agarose gel, and the ~2.9 kb PstI-EcoR1 restriction fragment of plasmid pPR12AR1 was isolated and prepared for ligation in substantial accordance with the procedure of Example 6.

About 10 μg of plasmid pL47 were digested with restriction enzymes PstI and BamHI in 200 ul of high-salt buffer at 37° C. for two hours. The PstI-BamHI-digested DNA was loaded onto an agarose gel, and the ~2.7 kb PstI-BamHI restriction fragment that comprised the origin of replication and a portion of the ampicillin resistance-conferring gene was isolated and prepared for ligation in substantial accordance with the procedure of Example 6. In a separate reaction, about 10 ug of plasmid pL47 DNA were digested with restriction enzymes EcoRI and BamHI in 200 ul of high-salt buffer at 37° C. for two hours, and the ~1.03 kb EcoRI-BamHI restriction fragment that comprised the novel transcriptional and translational activating sequence and the EK-BGH-encoding DNA was isolated and prepared for ligation in substantial accordance with the procedure of Example 6. The ~2 ug of the ~1.03 kb EcoRI-BamHI restriction fragment obtained were used in the construction of plasmid pL110.

The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to construct plasmid pL110, and the ligated DNA was used to transform *E. coli* K12 RV308 in substantial accordance with the procedure of Examples 2 and 3, except that tetracycline resistance, not ampicillin resistance, was used as the basis for selecting transformants.

Two PstI restriction enzyme recognition sites are present in the EK-BGH coding region that are not depicted in the restriction site and function maps presented in the accompanying drawings. A restriction site and function map of plasmid pL110 is presented in FIG. 12 of the accompanying drawings.

EXAMPLE 10

Construction of *E. coli* K12 RV308/pL110C

A. Construction of *E. coli* K12 RV308/pL110A

About 1 μg of plasmid pL110 DNA was digested with restriction enzyme NdeI in 20 μl total volume containing 2 μl of 10X high-salt buffer (1.0M NaCl; 0.50M Tris-HCl, pH=7.5; 0.10M MgCl$_2$; and 10 mM dithiothreitol) and 3 units of NdeI enzyme for 1 hour at 37° C. The reaction mixture was extracted with phenol/chloroform and the DNA precipitated with ethanol. The NdeI-digested plasmid pL110 DNA was dissolved in 50 μl of 1X Klenow buffer (40 mM KPO$_4$, pH=7.5; 6.6 mM MgCl$_2$; 1.0 mM 2-mercaptoethanol; 33 μM dATP; 33 μM dCTP; 33 μM dGTP; and 33 μM TTP). Two μl (~10 units, New England Biolabs) of the large fragment of *E. coli* DNA polymerase I, known as Klenow, were added to and mixed with the DNA, and the resulting reaction was incubated at 16° C. for 1 hour. The reaction was terminated by phenol extraction and the DNA conventionally purified. The NdeI-digested, Klenow-treated DNA was then ligated with T4 DNA ligase at 4° C. for 16 hours. The resulting DNA was used to conventionally transform *E. coli* K12 strain RV308 (NRRL B-15624). Transformants were selected on L-agar plates containing 100 μg/ml ampicillin and plasmids isolated from resistant colonies by the rapid alkaline extraction procedure described by Birnboim and Doly. A plasmid (pL110A in FIG. 13) lacking an NdeI site was selected.

B. Construction of Phage pL110B by Site-Specific Mutagenesis

Figure 13:
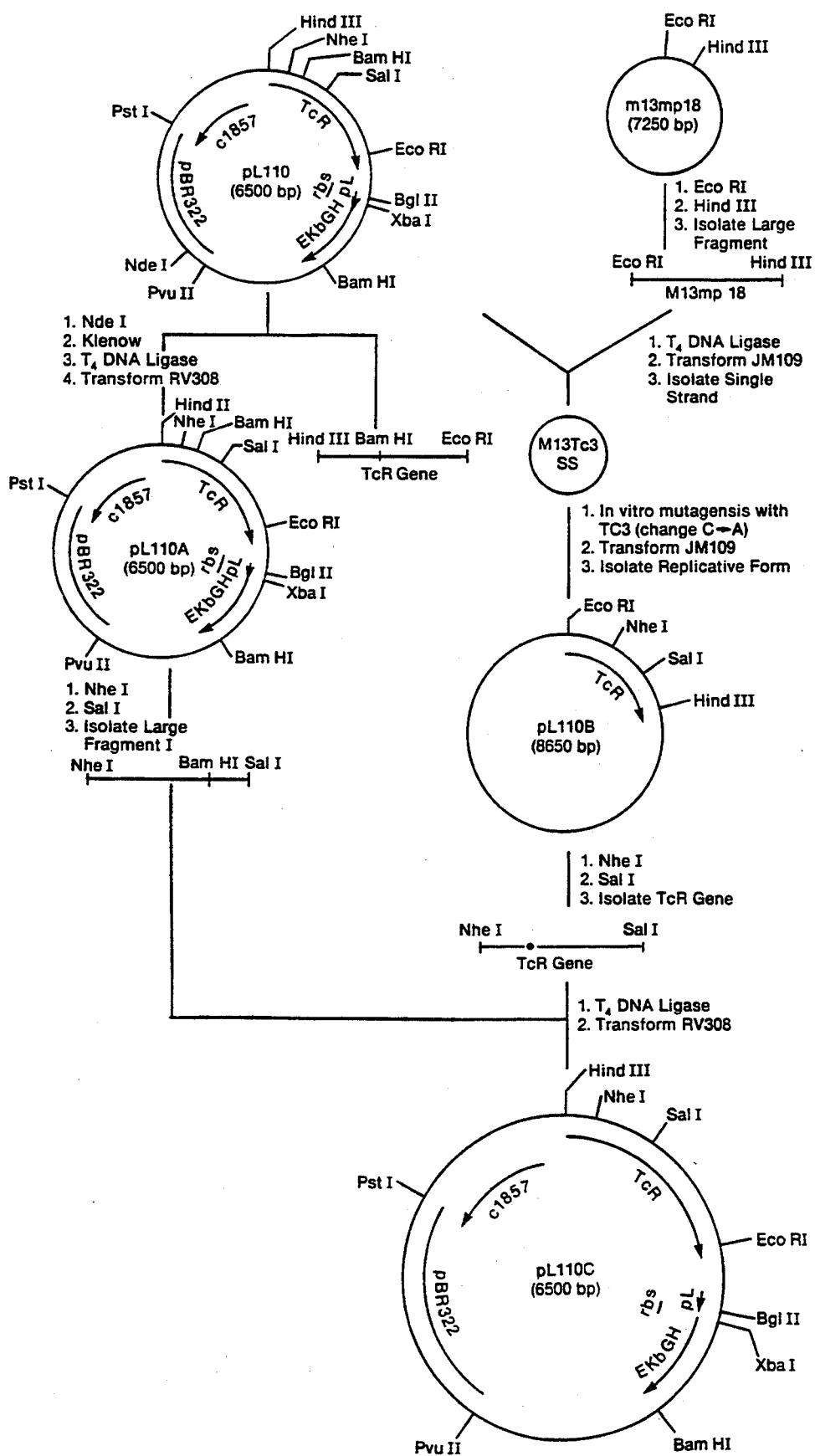
FIG. 13—a chart designating the construction of and a restriction site and function map of plasmid pL110C.

The protocol for eliminating the BamHI site in the tetracycline resistance-conferring gene by site-specific mutagenesis is shown on the right hand side of FIG. 13 of the accompanying drawings.

B(i) Construction of Phage M13Tc3

Plasmid pL110 served as the source of the tetracycline resistance-conferring gene. About 50 μg of plasmid pL110 in 50 μl of TE buffer were added to 25 μl of 10X HindIII buffer and 170 μl of H$_2$O. About 5 μl (~50 units) of restriction enzyme HindIII were added to the solution of plasmid pL110 DNA, and the resulting reaction was incubated at 37° C. for 2 hours. About 13 µl of 2M Tris-HCl, pH=7.4, and 5 µl (~50 units) of restriction enzyme EcoRI were added to the HindIII-digested plasmid pL110 DNA, and the reaction was incubated for 2 more hours at 37° C. The reaction was stopped by extracting the reaction mixture with TE-saturated phenol; the phenol was removed by chloroform extractions. The EcoRI-HindIII-digested plasmid pL110 DNA was then collected by precipitation and centrifugation, loaded into a 1% agarose gel, and the large ~4.3 kb EcoRI-HindIII restriction fragment was isolated and purified.

About 5 µg of phage m13mp18 (New England Biolabs) were dissolved in 50 µl of TE buffer and then digested with HindIII and EcoRI as described above. The HindIII-EcoRI-cut phage M13mp18 DNA was purified as described for pL110 except that an ~7.25 kb restriction fragment was isolated and purified.

About 100 nanograms of the ~4.3 kb HindIII-EcoRI fragment of plasmid pL110 were mixed with about 100 nanograms of the ~7.25 kb HindIII-EcoRI fragment of phage M13mp18, 2 µl of 10X ligase buffer, 1 µl (~100 units) of T4 DNA ligase, and 14 µl of H₂O. The ligation reaction was incubated at 15° C. for 1.5 hours; the ligated DNA constituted the desired phage m13Tc3 DNA. A restriction site and function map of phage m13Tc3 is presented in FIG. 13 of the accompanying drawings.

One ml of an overnight culture of E. coli K12 JM109 (E. coli K12 JM101, available from New England Biolabs, can be used instead of E. coli K12 JM109) was used to inoculate 50 ml of L broth, and the resulting culture was incubated at 37° C. with aeration until the O.D.$_{660}$ was between 0.3 and 0.4. The cells were resuspended in 25 ml of 10 mM NaCl, incubated on ice for 10 minutes, and collected by centrifugation. The cells were resuspended in 1.25 ml of 75 mM CaCl₂; a 200 µl aliquot of the cells was removed, added to 10 µl of the ligated DNA prepared above, and incubated on ice for about 40 minutes. The cell-DNA mixture was then incubated at 42° C. for 2 minutes, and varying aliquots (1, 10, and 100 µl) were removed and added to 3 ml of top agar (L broth with 0.5% agar kept molten at 45° C.) that also contained 50 µl of 2% X-Gal, 50 µl of 100 mM IPTG, and 200 µl of E. coli K12 JM109 in logarithmic growth phase. The cell-top agar mixture was then plated on L-agar plates containing 40 µg/ml X-Gal (5-bromo-4-chloro-3-indolyl-β-D-thiogalactoside) and 0.1 mM IPTG (isopropyl-β-D-thiogalactoside), and the plates were incubated at 37° C. overnight.

The following morning, several clear, as opposed to blue, plaques were individually used to inoculate 2 ml of L broth, and the resulting cultures were incubated at 37° C. with aeration for 2 hours. The absence of blue color indicates the desired DNA insertion occurred. Then, the cultures were centrifuged, and 200 µl of the resulting supernatant were added to 10 ml cultures (O.D.$_{550}$=0.5) of E. coli K12 JM109 growing at 37° C. with aeration. These cultures were incubated for another 30 minutes at 37° C.; then, the cells were pelleted by centrifugation and used to prepare the replicative form of the recombinant phage they contained. Double-stranded, replicative form phage DNA was isolated from the cells using a scaled-down version of the procedure described in Example 1. Transformants containing phage m13Tc3 DNA were identified by restriction enzyme analysis of their phage DNA.

B(ii) Preparation of Single-Stranded Phage m13Tc3 DNA

One and one-half ml of an overnight culture of E. coli K12 JM109/m13Tc3 were centrifuged, and 100 µl of the phage m13Tc3-containing supernatant were used to inoculate a 25 ml culture of E. coli JM109 at an O.D.$_{660}$ of about 0.4–0.5. The culture was incubated for 6 hours at 37° C. with aeration, at which time the culture was centrifuged and the resulting supernatant, about 20 ml, transferred to a new tube. About 2 ml of a solution containing 20% polyethylene glycol (PEG) 6000 and 14.6% NaCl were added to the supernatant, which was then incubated on ice for 20 minutes.

The supernatant was centrifuged for 25 minutes at 7000 rpm, and the resulting pellet, which contained single-stranded phage m13Tc3 DNA, was resuspended in 500 µl of TE buffer. The DNA solution was extracted twice with TE-saturated phenol and twice with chloroform. The single-stranded DNA was then precipitated using NaOAc and ethanol and centrifuged. The resulting pellet was washed with 70% ethanol, dried, and then dissolved in 60 µl of H₂O.

B(iii) Mutagenesis

The single-stranded DNA fragment used in the mutagenesis was synthesized on an automated DNA synthesizer. The fragment has the sequence, 5'-CCCGTCCTGTGGATACTCTACGCCGA-3', and is homologous to the region surrounding the BamHI site (5'-GGATCC-3') in the tetracycline resistance-conferring gene from plasmid pBR322, except that the A residue second from the 5' end (or third from the 3' end) is a C in plasmid pBR322. This change does not alter the amino acid composition of the tetracycline resistance-conferring protein but eliminates the BamHI site.

About 10 picomoles of the mutagenic primer and the M13 universal primer (Bethesda Research Laboratories (BRL), P.O. Box 6009, Gaithersburg, Md. 20760) were individually treated with 10 units (BRL) of T4 polynucleotide kinase in 20 µof 1X kinase buffer (60 mM Tris-HCl, pH=7.8; 15 mM 2-mercaptoethanol; 10 mM MgCl₂; and 0.41 µM ATP) for 30 minutes at 37° C. The kinase-treated DNAs were used in the mutagenesis procedure described below.

The annealing reaction was carried out mixing together 300 nanograms (1.2 µl) of single-stranded phage m13Tc3, 1 picomole (2 µl) of the universal primer, 1 picomole (2 µl) of the mutagenic primer, 2 µl of 10X annealing buffer (100 mM Tris-HCl, pH=7.5; 1 mM EDTA; and 500 mM NaCl), and 12.8 µl of H₂O. The reaction was incubated at 80° C. for 2 minutes, at 50° C. for 5 minutes, and then allowed to cool to room temperature.

The extension reaction was carried out by adding 5 µl of 10X extension buffer (500 mM Tris-HCl, pH=8; 1 mM EDTA; and 120 mM MgCl₂); 5 µl of 2 mM dATP; 1 µl of a solution 6 mM in each of dGTP, TTP, and dCTP; 1 µl (~2 units, Pharmacia P-L Biochemicals, 800 Centennial Avenue, Piscataway, N.J. 08854) of Klenow enzyme; 1 µl (100 units) of T4 DNA ligase; and 17 µl of H₂O to the mixture of annealed DNA. The extension reaction was incubated at room temperature for 1 hour, then at 37° C. for 2.5 hours, and then overnight at 4° C.

The reaction was stopped by two extractions with TE-saturated phenol, which were followed by two extractions with CHCl$_3$. The DNA was precipitated with ethanol and NaOAc. The DNA was collected by centrifugation and resuspended in 50 μl of H$_2$O, and 6 μl of 10X S1 buffer were then added to the solution of DNA.

The solution of DNA was split equally into three tubes. About 200 units (Miles Laboratories) of S1 nuclease were added to two of the tubes. One S1 reaction was incubated at room temperature for 5 minutes, the other for 10 minutes. The reactions were stopped by extracting the reaction mixture twice with TE-saturated phenol. The phenol extractions were followed by two extractions with chloroform; then, the DNA was precipitated from the reaction mixture with NaOAc and ethanol. The untreated sample of DNA served as a negative control. The S1-treated samples were kept separate from each other throughout the remainder of the procedure but gave similar results.

The DNA pellets were resuspended in 20 μl of H$_2$O, and 10 μl of the resulting solution were used to transform E. coli K12 JM109 (E. coli K12 JM101 could also be used) in accordance with the procedure used during the construction of phage m13Tc3, except that no IPTG or X-Gal was added to the plates.

Double-stranded replicative form DNA from about 48 plaques was isolated as described above and screened for the presence of a BamHI restriction site. Isolates without a BamHI site were further screened by preparing single-stranded DNA as described above. The single-stranded DNA was sequenced using the dideoxy sequencing method (J. H. Smith, 1980, Methods in Enzymology 65: 560–580). The desired isolate was designated pL110B (FIG. 13).

C. Construction of Plasmid pL110C

About 50 μg of the replicative form of phage pL110B DNA were digested in 250 μl of 1X NheI buffer (50 mM NaCl; 6 mM Tris-HCl, pH=7.5; 6 mM MgCl$_2$; and 6 mM β-mercaptoethanol) containing ~50 units of NheI restriction enzyme at 37° C. for 2 hours. Five μl of 5M NaCl were then added to the NheI-digested phage pL110B DNA, followed by 5 μl (~50 units) of SalI restriction enzyme. Digestion was continued for 2 hours at 37° C. The desired ~422 bp NheI-SalI fragment containing the mutated region of the tetracycline resistance-conferring gene was then isolated from an acrylamide gel, according to the teaching of Example 11.

Plasmid pL110A DNA was digested with NheI and SalI under identical conditions, except that plasmid pL110A was substituted for phage pL110B. The ~6.1 kb NheI-SalI restriction fragment of plasmid pL110A was purified from agarose.

The desired plasmid pL110C was constructed by ligating together 100 nanograms each of the NheI-SalI fragments of pL110A (~6.1 kb) and pL110B (~422 bp) using conventional procedures. A restriction site and function map of plasmid pL110C is presented in FIG. 13 of the accompanying drawings. The desired plasmid pL110C confers tetracycline resistance to 10 μg/ml tetracycline in E. coli but lacks a BamHI site in the tetracycline resistance-conferring gene.

EXAMPLE 11

Construction of E. coli K12 RV308/pGAG1317

A. Isolation of the ~200 bp EcoRI-SstII fragment of Plasmid pAG932

E. coli K12 DH5/pAG932 can be obtained from the Northern Regional Resesarch Laboratory in lyophilized or under the accession number NRRL B-18266. A restriction site and function map of pAG932 is presented in FIG. 14 of the accompanying drawings. Plasmid DNA is extracted from the culture in substantial accordance with the teaching of Example 1, except that the temperature of incubation is 37° C.

About 10 μg of plasmid pAG932 were dissolved in 20 μl 10X SstII buffer (500 mM Tris-HCl (pH 8.0), 100 mM MgCl$_2$ and 500 mM NaCl), 20 μl 1 mg/ml BSA, 5 μl (~50 units) restriction enzyme SstII, and 155 μl H$_2$O, and the resulting reaction was incubated at 37° C. for two hours. Next, 20 μl of 10X EcoRI buffer and 5 μl (~50 units) of restriction enzyme EcoRI were added and the reaction was left at 37° C. for 2 hours. The DNA was precipitated and resuspended, then ran over a 3.5% polyacrylamide gel as taught in Maniatis et al., 1982, Molecular Cloning (Cold Spring Harbor Laboratory). The DNA was visualized by ethidium bromide staining and the ~205 base pair EcoRI-SstII fragment was excised from the gel, crushed and left overnight at 37° C. in 300 μ 1 0.5M ammonium acetate, 10 mM magnesium acetate, 0.1% SDS, and 1 mM EDTA (pH 8.0). The sample was centrifuged 10 minutes at 10,000 g and the supernatant was collected and passed through a plug of glass wool. Two volumes of cold 100% ethanol were added to the supernatant and the DNA precipitated. The pellet was dissolved first in 200 μl of TE and 25 μl 3M sodium acetate then 600 μl 100% EtOH was added. After 10 minutes at −70° C., the DNA was spun at 15,000 g for 15 minutes. The supernatant was removed and the pellet was air dried, then resuspended in 10 μl TE.

B. Isolation of the ~1100 bp SstII-BglII fragment of Plasmid pAG1338

E. coli K12 DH5/pAG1338 can be obtained from the Northern Regional Research Laboratory in lyophilized form under the accession number NRRL B-18265. A restriction site and function map of pAG1338 is presented in FIG. 15 of the accompanying drawings. Plasmid DNA is extracted from the culture in substantial accordance with the teaching of Example 1, except that the temperature of incubation is 37° C.

About 10 μg of plasmid pAG1338 were dissolved in 20 μl SstII buffer, 20 μl 1 mg/ml BSA, 5 μl (~50 units) restriction enzyme SstII, 5 μl (~50 units) of restriction enzyme BglII and 150 μl H$_2$O. After incubating the reaction at 37° C. for 2 hours, the reaction mixture was electrophoresed on a 1% agarose gel for ~2 hours at 100 V.

The gel was stained in a dilute solution of ethidium bromide, and the desired ~1111 bp SstII-BglII band, which was visualized with long-wave UV light, was excised as a small gel segment. The gel segment was cut into very small pieces, put into an Eppendorf tube, mixed with an equal volume of buffer-saturated phenol, vortexed well, and kept at −70° C. for 10 minutes. After centrifugation for 10 minutes at 4° C., the aqueous layer was further extracted 2 times with an equal volume of buffer-saturated phenol and 2 times with an equal volume of chloroform. The desired SstII-BglII DNA fragment was ethanol precipitated and resuspended in 10 μl TE.

C. Construction of Plasmid pGAG1317

Plasmid pGEM ™ -4 was purchased from Promega Biotec (2800 S. Fish Hatchery Road, Madison, Wis. 53711). A restriction site and function map of plasmid pGEM ™ -4 is presented in FIG. 16 of the accompanying drawings. One μl of plasmid pGEM ™ -4 was digested in substantial accordance with the teaching of Example 2, except ~50 units of restriction enzyme EcoRI and 10X EcoRI buffer (1M Tris-HCl (pH 7.5), 500 mM NaCl and 100 mM MgCl₂) were used. After 2 hours at 37° C., 5 μl of restriction enzyme BamHI and 20 μl 10X BamHI buffer (200 mM Tris-HCl (pH 8.0), 1M NaCl and 70 mM MgCl₂) were added and the reaction was left for 2 more hours at 37° C. The reaction was stopped and the large vector fragment was isolated from a gel in substantial accordance with the teaching of Example 11B. This fragment was resuspended in 10 μl TE.

About 2 μl of the EcoRI-BamHI cut vector of pGEM ™ -4, 3 μof the ~200 bp EcoRI-SstII fragment of pAG932, 3 μl of the ~1100 bp SStII-BglII fragment of pAG1338, 2.5 μl ligase buffer, 2.5 μl of 1 mg/ml BSA, 7 μl of 5 mM ATP, 2.5 μl of T4 DNA ligase, 2.5 μl of 10 mM Spermidine and 8 μl of water were mixed in a ligation reaction in substantial accordance with the teaching of Example 2. The resultant plasmid was designated plasmid pGAG1317. This plasmid was next transformed into E. coli RV308 cells in substantial accordance with the teaching of Example 3. A restriction site and function map of plasmid pGAG1317 is presented in FIG. 17 of the accompanying drawings.

EXAMPLE 12

Construction of E. coli K12 RV308/pLKSA

Plasmid pGAG1317 was isolated in substantial accordance with the teaching of Example 1. About 10 μl of plasmid pGAG1317 were digested in substantial accordance with the teaching of Example 2, except restriction enzyme ApaI and 10X ApaI buffer (60 mM Tris-HCl (pH 7.4), 60 mM NaCl and 60 mM MgCl₂) were used. After incubating at 37° C. for 2 hours, the reaction was stopped, ethanol precipitated, and resuspended in 5 μl 10X calf intestine alkaline phosphatase (CIAP) buffer (5M Tris-HCl (pH 9.0), 100 mM MgCl₂, 10 mM ZnCl₂, 100 mM spermidine), 44 μl H₂O, 1 μl CIAP (~7 units). This reaction was incubated for 15 minutes at 37° C. and then for 15 minutes at 56° C. Another 1 μl of CIAP was added and the reaction was again incubated for 15 minutes at 37° C. and for 15 minutes at 56° C. The reaction was terminated and the DNA vector was then precipitated in substantial accordance with the teaching of Example 2.

A DNA linker with an ApaI end and an XbaI end was synthesized in substantial accordance with the teaching of Example 4. This linker has the following structure:

The linker was kinased and ligated into the ApaI digested plasmid pGAG1317 in substantial accordance with the teaching of Example 2. The resulting ligation reaction was incubated at 4° C. overnight. After the ligation reaction, the reaction mixture was adjusted to have the composition of XbaI buffer (6 mM Tris-HCl (pH 7.4), 100 mM NaCl and 6 mM MgCl₂). About 10 μl (100 units) of restriction enzyme XbaI were added to the mixture, and the resulting reaction was incubated at 37° C. for 2 hours.

The reaction was terminated, and the XbaI-digested DNA was precipitated, resuspended and digested with restriction enzyme EcoRI in substantial accordance with the teaching of Example 11C. After 2 hours at 37° C., the reaction mixture was precipitated and ran through a polyacrylamide gel, then the ~500 bp XbaI-EcoRI fragment was isolated, eluted and purified in substantial accordance with the teaching of Example 11A.

About 1 μg of plasmid pL110C (from Example 10) was digested with restriction enzyme EcoRI in substantial accordance with the teaching of Example 11C. After 1 hour at 37° C., 20 μl of 10X XbaI buffer and 5 μl of restriction enzyme XbaI were added to the reaction, which was then incubated another hour at 37° C. The reaction was stopped and the DNA was run through an agarose gel and the large vector band was isolated in substantial accordance with the teaching of Example 11B. The EcoRI-ApaI/XbaI fragment isolated above was then ligated into the XbaI-EcoRI-digested pL110C, and the resultant plasmid was transformed into E. coli K12 RV308 in substantial accordance with the teaching of Examples 2 and 3. The resultant plasmid is designated plasmid pLKSA-B. A restriction site and function map of plasmid pLKSA-B is presented in FIG. 18 of the accompanying drawings.

10 μg of plasmid pLKSA-B, isolated in substantial accordance with the teaching of Example 2, were digested with restriction enzyme EcoRI in substantial accordance with the teaching of Example 11C, and dephosphorylated in substantial accordance with the teaching of Example 12. The DNA was then precipitated, washed and resuspended in 5 μl TE in substantial accordance with the teaching of Example 2. About 600 picomoles of the 5'-3' strand of EcoRI-BamHI linkers were kinased in substantial accordance with the teaching of Example 2. These linkers have the following structure:

After a one hour incubation at 37° C., the reaction mixture was placed at 90° C. for 10 minutes to heat-kill the kinase. About 0.1 μg of the EcoRI digested, phosphatased pLKSA-B were added to the reaction mix along with the unphosphorylated complementary strand of the EcoRI-BamHI linkers. This strand has the structure:

The reaction mixture was allowed to slowly cool to room temperature, thereby allowing all complementary strands to anneal. This results in a linker with the following structure:

5'-AATTCTCAATGCAGGGTCTAAAATAAG-3'
3'-GAGTTACGTCCCAGATTTTATTCCTAG-5'

The only base which is phosphorylated on this linker is the adenyl at the 5' end. All DNA fragments were next ligated together in substantial accordance with the teaching of Example 2. After the ligation reaction, the reaction mixture was adjusted to have the composition of high-salt buffer. About 10 μl (100 units) of restriction enzyme XbaI were added to the mixture, and the resulting reaction was incubated at 37° C. for 2 hours. The DNA was electrophoresed through a polyacrylamide gel and the ~500 bp XbaI-EcoRI/BamHI fragment was isolated and purified in substantial accordance with the teaching of Example 11A.

About 1 μg of plasmid pL110C was digested with restriction enzymes XbaI and BamHI in high-salt buffer in substantial accordance with the teaching of Example 2. The DNA was isolated and the large vector fragment was purified from an agarose gel in substantial accordance with the teaching of Example 11B. The XbaI-EcoRI/BamHI fragment of pLKSA-B was next ligated into the XbaI-BamHI digested pL110C. The resultant plasmid was designated pLKSA. A restriction site and function map of plasmid pLKSA is presented in FIG. 19 of the accompanying drawings.

Plasmid pLKSA was transformed into E. coli RV308 in substantial accordance with the teaching of Examples 2 and 3. A single colony was grown overnight in 50 mls of LB broth plus 15 μg/ml tetracycline at 30° C. The temperature was then shifted to 42° C. and the culture was allowed to shake in the incubator for three more hours. The cells were then pelleted and resuspended in 4 parts LB broth and 1 part lysis mix. Lysis mix is 1 mM EDTA, 0.17 mg/ml lysozyme and 6 μg/ml DNA in water. The culture was left on ice for 1 hour, then alternatively frozen at −70° C. and thawed at 37° C. This freeze-thawing regimen was repeated two more times, then the cellular debris/KSA was blotted onto nitrocellulose. Polyclonal antibodies, raised against the KSA isolated from UCLA-P3 cells, react specifically with those cultures which express recombinant KSA.

EXAMPLE 13

Preparation of BK Virus DNA

BK virus is obtained from the American Type Culture Collection under the accession number ATCC VR-837. The virus is delivered in freeze-dried form and resuspended in Hank's balanced salts (Gibco, 3175 Staley Road, Grand Island, N.Y. 14072) to a titer of about $10^5$ plaque-forming units (pfu)/ml. The host of choice for the preparation of BK virus DNA is primary human embryonic kidney (PHEK) cells, which can be obtained from Flow Laboratories, Inc., 7655 Old Springhouse Road, McLean, Va. 22101, under catalogue number 0-100 or from M. A. Bioproducts under catalogue number 70-151.

About five 75 mm² polystyrene flasks comprising confluent monolayers of about $10^6$ PHEK cells are used to prepare the virus. About 1 ml of BK virus at a titer of $10^5$ pfu/ml is added to each flask, which is then incubated at 37° C. for one hour, and then, fresh culture medium (Dulbecco's Modified Eagle's Medium, Gibco, supplemented with 10% fetal bovine serum) is added, and the infected cells are incubated at 37° C. for 10–14 days or until the full cytopathogenic effect of the virus is noted. This cytopathogenic effect varies from cell line to cell line and from virus to virus but usually consists of cells rounding up, clumping, and sloughing off the culture disk.

The virus is released from the cells by three freeze-thaw cycles, and the cellular debris is removed by centrifugation at 5000 Xg. The virus in 1 liter of supernatant fluid is precipitated and collected by the addition of 100 g of PEG-6000, incubation of the solution for 24 hours at 4° C., and centrifugation at 5000 Xg for 20 minutes. The pellet is dissolved in 0.1X SSC buffer (1XSSC=0.15M NaCl and 0.015M NaCitrate, pH=7) at 1/100th of the original volume. The virus suspension is layered onto a 15 ml solution of saturated KBr in a tube, which is centrifuged at 75,000 Xg for 3 hours. Two bands are evident in the KBr solution after centrifugation. The lower band, which contains the complete virion, is collected and desalted on a Sephadex ® G-50 column (Sigma Chemical Co., P.O. Box 14508, St. Louis, Mo. 63178) using TE (10 mM Tris-HCl, pH=7.8, and 1 mM EDTA) as an elution buffer.

Sodium dodecyl sulfate (SDS) is added to the solution of purified virions obtained from the column to a concentration of 1%; pronase is added to a concentration of 100 μg/ml, and the solution is incubated at 37° C. for 2 hours. Cesium chloride is then added to the solution to a density of 1.56 g/ml, and ethidium bromide is added to the solution to a final concentration of 100 μg/ml. The solution is centrifuged in a Sorvall (DuPont-Inst. Products, Biomedical Division, Newton, Conn. 06470) 865 rotor or similar vertical rotor at 60,000 Xg for 24 hours. After centrifugation, the band of virus DNA is isolated and extracted five times with isoamyl alcohol saturated with 100 mM Tris-HCl, pH=7.8. The solution of BK virus DNA is then dialyzed against TE buffer until the 260 nm/280 nm absorbance ratio of the DNA is between 1.75 and 1.90. The DNA is precipitated by adjusting the NaCl concentration to 0.15M, adding two volumes of ethanol, incubating the solution at −70° C. for at least 2 hours, and centrifuging the solution at 12,000Xg for 10 minutes. The resulting pellet of BK virus DNA is suspended in TE buffer at a concentration of 1 mg/ml.

EXAMPLE 14

Construction of Plasmids pBKneo1 and pBKneo2

E. coli K12 HB101/pdBPV-MMTneo cells are obtained in lyophil form from the American Type Culture Collection under the accession number ATCC 37224. The lyophilized cells are plated on L-agar plates containing 100 μg/ml ampicillin and incubated at 37° C. to obtain single colony isolates.

One liter of L broth (10 g tryptone, 10 g NaCl, and 5 g yeast extract per liter) containing 50 μg/ml ampicillin was inoculated with a colony of E. coli K12 HB101/pdBPV-MMTneo and incubated in an air-shaker at 37° C. until the O.D.$_{590}$ was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

Plasmid DNA was then isolated from this culture in substantial accordance with the teaching of Example 1 and the ~1 mg of plasmid pdBPV-MMTneo DNA obtained by this procedure was suspended in 1 ml of TE buffer and stored at −20° C.

About 5μg (5μl) of the plasmid pdBPV-MMTneo DNA prepared above and five μg (5 μl) of the BK virus DNA prepared in Example 13 were each digested at 37° C. for 2 hours in a solution containing 2 μl of 10X BamHI buffer (1.5 M NaCl; 60 mM Tris-HCl, pH=7.9; 60 mM MgCl$_2$; and 1 mg/ml BSA), 1 μl of restriction enzyme BamHI, and 7 μl of H$_2$O. The reaction was stopped by an extraction with an equal volume of phenol, followed by two extractions with chloroform. Each BamHI-digested DNA was then precipitated, collected by centrifugation, and resuspended in 5 μl of H$_2$O.

About 1 μl of 10X ligase buffer was added to a mixture of BamHI-digested plasmid pdBPV-MMTneo (1 μl) and BamHI-digested BK virus DNA (1μl). After 1 μl (~1000 units) of T4 DNA ligase and 6 μl of H$_2$O were added to the mixture of DNA, the resulting reaction was incubated at 16° C. overnight. The ligated DNA constituted the desired plasmids pBKneo1 and pBKneo2, which differ only with respect to the orientation of the BK virus DNA. Plasmid pBKneo1 contains an ~2.1 kb SalI-HindIII restriction fragment.

*E. coli* K12 HB101 cells are available in lyophilized form from the Northern Regional Research Laboratory under the accession number NRRL B-15626. *E. coli* K12 HB101 cells were cultured, made competent for transformation, and transformed with the ligated DNA prepared above in substantial accordance with the procedure of Example 3. The transformed cells were plated on L-agar plates containing 100 μg/ml ampicillin. *E. coli* K12 HB101/pBKneo1 and *E. coli* K12/pBKneo2 transformants were identified by their ampicillin-resistant phenotype and by restriction enzyme analysis of their plasmid DNA.

EXAMPLE 15

Construction of Plasmid pBLcat

A. Construction of Intermediate Plasmid pLPcat

The virion DNA of adenovirus 2 (Ad2) is a double-stranded linear molecule about 35.94 kb in size. The Ad2 late promoter can be isolated on an ~0.316 kb AccI-PvuII restriction fragment of the Ad2 genome; this ~0.32 kb restriction fragment corresponds to the sequence between nucleotide positions 5755 and 6071 of the Ad2 genome. To isolate the desired ~0.32 kb AccI-PvuII restriction fragment, Ad2 DNA is first digested with restriction enzyme BalI, and the ~2.4 kb BalI restriction fragment that comprises the entire sequence of the ~0.32 kb AccI-PvuII restriction fragment is isolated. Then, the ~2.4 kb BalI restriction fragment is digested with AccI and PvuII to obtain the desired fragment.

About 50 μg of Ad2 DNA (available from BRL or ATCC VR-2) are dissolved in 80 μl of H$_2$O and 10 μl of 10X BalI buffer (100 mM Tris-HCl, pH=7.6; 120 mM MgCl$_2$; 100 mM DTT; and 1 mg/ml BSA). About 10 μl (~20 units) of restriction enzyme BalI are added to the solution of Ad2 DNA, and the resulting reaction is incubated at 37° C. for 4 hours.

The BalI-digested DNA is loaded onto an agarose gel and electrophoresed until the restriction fragments are well separated. Visualization of the electrophoresed DNA is accomplished by staining the gel in a dilute solution (0.5 μg/ml) of ethidium bromide and exposing the stained gel to long-wave ultraviolet (UV) light. One method to isolate DNA from agarose is as follows. A small slit is made in the gel in front of the desired fragment, and a small piece of NA-45 DEAE membrane (Schleicher and Schuell, Keene, N.H. 03431) is placed in each slit. Upon further electrophoresis, the DNA non-covalently binds to the DEAE membrane. After the desired fragment is bound to the DEAE membrane, the membrane is removed and rinsed with low-salt buffer (100 mM KCl; 0.1 mM EDTA; and 20 mM Tris-HCl, pH=8). Next, the membrane is placed in a small tube and immersed in high-salt buffer (1M NaCl; 0.1 mM EDTA; and 20 mM Tris-HCl, pH=8) and then incubated at 65° C. for one hour to remove the DNA from the DEAE paper. After the 65° C. incubation, the incubation buffer is collected and the membrane rinsed with high-salt buffer. The high-salt rinse solution is pooled with the high-salt incubation buffer.

The volume of the high salt-DNA solution is adjusted so that the NaCl concentration is 0.25M, and then three volumes of cold, absolute ethanol are added to the solution. The resulting solution is mixed and placed at −70° C. for 10-20 minutes. The solution is then centrifuged at 15,000 rpm for 15 minutes. After another precipitation to remove residual salt, the DNA pellet is rinsed with ethanol, dried, resuspended in 20 μl of TE buffer, and constitutes about 3 μg of the desired restriction fragment of Ad2. The purified fragment obtained is dissolved in 10 μl of TE buffer.

About 6 μl of H$_2$O and 2 μl of 10X AccI buffer (60 mM NaCl; 60 mM Tris-HCl, pH=7.5; 60 mM MgCl$_2$; 60 mM DTT; and 1 mg/ml BSA) are added to the solution of the ~2.4 kb BalI restriction fragment of Ad2. After the addition of about 2 μl (~10 units) of restriction enzyme AccI to the solution of DNA, the reaction is incubated at 37° C. for 2 hours. After the AccI digestion, the DNA is collected by ethanol precipitation and resuspended in 16 μl of H$_2$O and 2 μl of 10X PvuII buffer (600 mM NaCl; 60 mM Tris-HCl, pH=7.5; 60 mM MgCl$_2$; 60 mM DTT; and 1 mg/ml BSA). After the addition of about 2 μl (about 10 units) of restriction enzyme pvuII to the solution of DNA, the reaction is incubated at 37° C. for 2 hours.

The AccI-PvuII-digested, ~2.4 kb BalI restriction fragment of Ad2 is loaded onto an ~6% polyacrylamide gel and electrophoresed until the ~0.32 kb AccI-PvuII restriction fragment that comprises the Ad2 late promoter is separated from the other digestion products. The gel is stained with ethidium bromide and viewed using UV light, and the segment of gel containing the ~0.32 kb AccI-PvuII restriction fragment is cut from the gel, crushed, and soaked overnight at room temperature in ~250 μl of extraction buffer (500 mM NH$_4$OAc; 10 mM MgOAc; 1 mM EDTA; and 0.1% SDS). The following morning, the mixture is centrifuged, and the pellet is discarded. The DNA in the supernatant is precipitated with ethanol; about 2 μg of tRNA are added to ensure complete precipitation of the desired fragment. About 0.2 μg of the ~0.32 kb AccI-PvuII restriction fragment are obtained and suspended in 7 μl of H$_2$O.

About 0.25 μg (in 0.5 μl) of BclI linkers (5'-CTGAT-CAG-3', available from New England Biolabs), which had been kinased in substantial accordance with the procedure described in Example 2 was added to the solution of the ~0.32 kb AccI-PvuII restriction fragment, and then, 1 μl (~1000 units) of T4 DNA ligase and 1 μl of 10X ligase buffer were added to the solution of DNA, and the resulting reaction was incubated at 16° C. overnight. The BclI linkers could only ligate to the PvuII end of the AccI-PvuII restriction fragment.

DNA sequencing later revealed that four BclI linkers attached to the PvuII end of the AccI-PvuII restriction fragment. These extra BclI linkers can be removed by BclI digestion and religation; however, the extra BclI linkers were not removed as the linkers do not interfere with the proper functioning of the vectors that comprise the extra linkers.

*E. coli* K12 HB101/pSV2cat cells are obtained in lyophilized form from the ATCC under the accession number ATCC 37155, and plasmid pSV2cat DNA was isolated from the cells in substantial accordance with the procedure of Example 1. About 1 mg of plasmid pSV2cat DNA is obtained and dissolved in 1 ml of TE buffer. About 3 μg (3 μl) of the plasmid pSV2cat DNA were added to 2 μl of 10X AccI buffer and 16 μl of $H_2O$, and then, 3 μl (about 9 units) of restriction enzyme AccI were added to the solution of pSV2cat DNA, and the resulting reaction was incubated at 37° C. for 2 hours. The AccI-digested plasmid pSV2cat DNA was then digested with restriction enzyme StuI by adding 3 μl of 10X StuI buffer (1.0M NaCl; 100 mM Tris-HCl, pH=8.0; 100 mM $MgCl_2$; 60 mM DTT; and 1 mg/ml BSA), 5 μl of $H_2O$, and about 2 μl (about 10 units) of restriction enzyme StuI. The resulting reaction was incubated at 37° C. for 2 hours. The reaction was terminated by extracting the reaction mixture once with phenol, then twice with chloroform. About 0.5 μg of the desired fragment was obtained and dissolved in 20 μl of TE buffer.

About 4 μl of the AccI-StuI-digested plasmid pSV2cat DNA were mixed with about 7 μl of the ~0.32 kb AccI-PvuII (with BclI linkers attached) restriction fragment of Ad2, and after the addition of 3 μl of 10X ligase buffer, 15 μl of $H_2O$, and 2 μl (about 1000 units) of T4 DNA ligase, the ligation reaction was incubated at 16° C. overnight. The ligated DNA constituted the desired plasmid pLPcat, a plasmid that comprises the Ad2 late promoter positioned so as to drive transcription, and thus expression, of the chloramphenicol acetyltransferase gene.

The ligated DNA was used to transform *E. coli* K12 HB101 cells in substantial accordance with the procedure of Example 3. The transformed cells were plated on L agar containing 50 μg/ml ampicillin; restriction enzyme analysis of plasmid DNA was used to identify the *E. coli* K12 HB101/pLPcat transformants. Plasmid pLPcat DNA was isolated from the transformants for use in subsequent constructions in substantial accordance with the plasmid isolation procedure described in Example 1.

B. Final Construction of Plasmid pBLcat

About 88 μg of plasmid pBKneo1 DNA in 50 μl of TE buffer were added to 7.5 μl of 10X AccI buffer, 30 μl of $H_2O$, and 15 μl (about 75 units) of restriction enzyme AccI, and the resulting reaction was incubated at 37° C. for 2 hours. The AccI-digested BK virus DNA was loaded on an agarose gel, and the ~1.4 kb fragment that contains the BK enhancer was separated from the other digestion products. The ~1.4 kb AccI restriction fragment was then isolated in substantial accordance with the procedure described in Example 15A. About 5 μg of the fragment were resuspended in 5 μl of 10X PvuII buffer, 45 μl of $H_2O$, and 5 μl (about 25 units) of restriction enzyme PvuII, and the resulting reaction was incubated at 37° C. for 2 hours. The PvuII-digested DNA was then isolated and prepared for ligation in substantial accordance with the procedure of Example 15A. About 2 μg of the desired ~1.28 kb AccI-pVuII fragment were obtained and dissolved in 5 μl of TE buffer.

About 1 μg of plasmid pLPcat DNA was dissolved in 5 μl of 10X AccI buffer and 40 μl of $H_2O$. About 5 μl (~25 units) of restriction enzyme AccI were added to the solution of plasmid pLPcat DNA, and the resulting reaction was incubated at 37° C. The AccI-digested plasmid pLPcat DNA was precipitated with ethanol and resuspended in 5 μl of 10X StuI buffer, 40 μl of $H_2O$, and 5 μl (about 25 units) of restriction enzyme StuI, and the resulting reaction was incubated at 37° C. for 2 hours. The AccI-StuI-digested plasmid pLPcat DNA was precipitated with ethanol several times to purify the ~4.81 kb AccI-StuI restriction fragment that comprises the *E. coli* origin of replication and Ad2 late promoter away from the other digestion product, a restriction fragment about 16 bp in size. About 1 μg of the desired ~4.81 kb restriction fragment was obtained and dissolved in 20 μl of TE buffer.

The 5 μl of ~4.81 kb AccI-StuI restriction fragment of plasmid pLPcat were added to 5 μl of ~1.28 kb AccI-PvuII restriction fragment of BK virus. After the addition of 3 μl of 10X ligase buffer, 15 μl of $H_2O$, and 2 μl (about 1000 units) of T4 DNA ligase to the mixture of DNA, the resulting ligation reaction was incubated at 16° C. overnight. The ligated DNA constituted the desired plasmid pBLcat.

The ligated DNA was used to transform *E. coli* K12 HB101 cells in substantial accordance with the procedure described in Example 3. *E. coli* K12 HB101/pBLcat transformants were identified by restriction enzyme analysis of their plasmid DNA. Plasmid pBLcat DNA was prepared for use in subsequent constructions in substantial accordance with the procedure of Example 3.

EXAMPLE 16

Construction of Plasmid pL133

A. Construction of Intermediate Plasmid pSV2-HPC8

Plasmid pHC7 comprises a DNA sequence that encodes human protein C. One liter of L-broth containing 15 μg/ml tetracycline was inoculated with a culture of *E. coli* K12 RR1/pHC7 (NRRL B-15926), and plasmid pHC7 DNA was isolated and purified in substantial accordance with the procedure of Example 1. About 1 mg of plasmid pHC7 DNA was obtained by this procedure, suspended in 1 ml of TE buffer, and stored at −20° C.

Fifty μl of the plasmid pHC7 DNA were mixed with 5 μl (~50 units) of restriction enzyme BanI, 10 μl of 10X BanI reaction buffer (1.5M NaCl; 60 mM Tris-HCl, pH=7.9; 60 mM $MgCl_2$; and 1 mg/ml BSA), and 35 μl of $H_2O$ and incubated until the digestion was complete. The BanI-digested plasmid pHC7 DNA was then electrophoresed on a 3.5% polyacrylamide gel (29:1, acrylamide:bisacrylamide), until the ~1.25 kb BanI restriction fragment was separated from the other digestion products.

The region of the gel containing the ~1.25 kb BanI restriction fragment was cut from the gel, placed in a test tube, and broken into small fragments. One ml of extraction buffer (500 mM $NH_4OAc$, 10 mM MgOAc, 1 mM EDTA 1% SDS and 10 mg/ml tRNA) was added to the tube containing the fragments, and the tube was placed at 37° C. overnight. Centrifugation was used to pellet the debris, and the supernatant was transferred to a new tube. The debris was washed once with 200 μl of extraction buffer; the wash supernatant was combined with the first supernatant from the overnight extraction. After passing the supernatant through a plug of glass wool, two volumes of ethanol were added to and mixed with the supernatant. The resulting solution was placed in a dry ice-ethanol bath for ~10 minutes, and then, the DNA was pelleted by centrifugation.

Approximately 8 μg of the ~1.25 kb BanI restriction fragment were obtained by this procedure. The purified fragment was suspended in 10 μl of TE buffer and stored at −20° C. The BanI restriction fragment had to be modified by the addition of a linker to construct plasmid pSV2-HPC8.

Five hundred picomoles of each single strand of the linker were kinased in 20 μl of reaction buffer, which contained 15 units (~0.5 μl) T4 polynucleotide kinase, 2 μl 10X ligase buffer, 10 μl of 500 μM ATP, and 7.5 μl of H₂O. The kinase reaction was incubated at 37° C. for 30 minutes, and the reaction was terminated by incubation at 100° C. for 10 minutes. In order to ensure complete kination, the reaction was chilled on ice, 2 μl of 0.2M dithiothreitol, 2.5 μl of 5 mM ATP, and 15 units of T4 polynucleotide kinase were added to the reaction mixture and mixed, and the reaction mixture was incubated another 30 minutes at 37° C. The reaction was stopped by another 10 minute incubation at 100° C. and then chilled on ice.

Although kinased separately, the two single strands of the DNA linker were mixed together after the kinase reaction. To anneal the strands, the kinase reaction mixture was incubated at 100° C. for 10 minutes in a water bath containing ~150 ml of water. After this incubation, the water bath was shut off and allowed to cool to room temperature, a process taking about 3 hours. The water bath, still containing the tube of kinased DNA, was then incubated at 4° C. overnight. This process annealed the single strands. The linker constructed had the following structure:

The linker was stored at −20° C. until use.

The ~8 μg of ~1.25 kb BanI fragment were added to and mixed with the ~50 μl of linker (~500 picomoles), 1 μl of T4 DNA ligase (~500 units), 10 μl of 10X ligase buffer, and 29 μl of H₂O, and the resulting ligation reaction was incubated at 4° C. overnight. The ligation reaction was stopped by a 10 minute incubation at 65° C. The DNA was pelleted by adding NaOAc to a final concentration of 0.3M, adding 2 volumes of ethanol, chilling in a dry ice-ethanol bath, and then centrifuging the solution.

The DNA pellet was dissolved in 10 μl of 10X ApaI reaction buffer (60 mM NaCl; 60 mM Tris-HCl, pH=7.4; 60 mM MgCl₂; and 60 mM 2-mercaptoethanol), 5 μl (~50 units) of restriction enzyme ApaI, and 85 μl of H₂O, and the reaction was placed at 37° C. for two hours. The reaction was then stopped and the DNA pelleted as above. The DNA pellet was dissolved in 10 μl of 10X HindIII reaction buffer, 5 μl (~50 units) of restriction enzyme HindIII, and 85 μl of H₂O, and the reaction was placed at 37° C. for two hours. After the HindIII digestion, the reaction mixture was loaded onto a 3.5% polyacrylamide gel, and the desired ~1.23 kb HindIII-ApaI restriction fragment was isolated in substantial accordance with the procedure described in Example 15A. Approximately 5 μg of the desired fragment were obtained, suspended in 10 μl of TE buffer, and stored at −20° C.

Fifty μl of plasmid pHC7 DNA were mixed with 5 μl (~50 units) of restriction enzyme PstI, 10 μl of 10X PstI reaction buffer (1.0M NaCl; 100 mM Tris-HCl, pH=7.5; 100 mM MgCl₂; and 1 mg/ml BSA), and 35 μl of H₂O and incubated at 37° C. for two hours. The PstI-digested plasmid pHC7 DNA was then electrophoresed on a 3.5% polyacrylamide gel, and the desired ~0.88 kb fragment was purified in substantial accordance with the procedure described above. Approximately 5 μg of the desired fragment were obtained, suspended in 10 μl of TE buffer, and stored at −20° C.

The ~5 μg of ~0.88 kb pstI fragment were added to and mixed with ~50 μl of the following linker, which was constructed on an automated DNA synthesizer:

About 1 μl of T4 DNA ligase (~10 units), 10 μl 10X ligase buffer, and 29 μl H₂O were added to the mixture of DNA, and the resulting ligation reaction was incubated at 4° C. overnight.

The ligation reaction was stopped by a 10 minute incubation at 65° C. After precipitation of the ligated DNA, the DNA pellet was dissolved in 10 μl of 10X ApaI reaction buffer, 5 μl (~50 units) of restriction enzyme ApaI, and 85 μl of H₂O, and the reaction was placed at 37° for two hours. The reaction was then stopped and the DNA pelleted once again. The DNA pellet was dissolved in 10 μl 10X BglII reaction buffer (1M NaCl; 100 mM Tris-HCl, pH=7.4; 100 mM MgCl₂; 100 mM 2-mercaptoethanol; and 1 mg/ml BSA), 5 μl (~50 units) of restriction enzyme BglII, and 85 μl H₂O, and the reaction was placed at 37° C. for two hours. After the BglII digestion, the reaction mixture was loaded onto a 3.5% polyacrylamide gel, and the desired ~0.19 kb ApaI-BglII restriction fragment was isolated in substantial accordance with the procedure described above. Approximately 10 μg of the desired fragment was obtained, suspended in 10 μl of TE buffer, and stored at −20° C.

Approximately 10 μg of plasmid pSV2gpt DNA (ATCC 37145) were dissolved in 10 μl of 10X HindIII reaction buffer, 5 μl (~50 units) of restriction enzyme HindIII, and 85 μl of H₂O, and the reaction was placed at 37° C. for 2 hours. The reaction mixture was then made 0.25M in NaOAc, and after the addition of two volumes of ethanol and incubation in a dry ice-ethanol bath, the DNA was pelleted by centrifugation. The DNA pellet was dissolved in 10 μl of 10X BglII buffer, 5 μl (~50 units) of restriction enzyme BglII, and 85 μl of H₂O, and the reaction was placed at 37° C. for two hours. After the BglII digestion, the reaction mixture was loaded onto a 1% agarose gel, and the fragments were separated by electrophoresis. The gel was stained with ethidium bromide and viewed under ultraviolet light, and the band containing the desired ~5.1 kb HindIII-BglII fragment was cut from the gel and placed in dialysis tubing, and electrophoresis was continued until the DNA was out of the agarose. The buffer containing the DNA from the dialysis tubing was extracted with phenol and CHCl₃, and then, the DNA was precipitated. The pellet was resuspended in 10 μl of TE buffer and constituted ~5 μg of the desired ~5.1 kb HindIII-BglII restriction fragment of plasmid pSV2gpt.

Two μl of the μ1.23 kb HindIII-ApaI restriction fragment, 3 μl of the ~0.19 kb ApaI-BglII fragment, and 2 μl of the ~5.1 kb HindIII-BglII fragment were mixed together and then incubated with 10 μl of 10X ligase buffer, 1 μl of T4 DNA ligase (~500 units), and 82 μl of H₂O at 16° C. overnight. The ligated DNA constituted the desired plasmid pSV2-HPC8. 10 *E. coli* K12 RR1 (NRRL B-15210) cells were made competent for transformation in substantial accordance with the procedure described in Example 3. The ligated DNA prepared above was used to transform the cells, and aliquots of the transformation mix were plated on L-agar plates containing 100 μg/ml ampicillin. The plates were then incubated at 37° C. *E. coli* K12 RR1/pSV2-HPC8 transformants were verified by restriction enzyme analysis of their plasmid DNA.

B. Final Construction of Plasmid pL133

Fifty μg of plasmid pSV2-HPC8 were dissolved in 10 μl of 10X HindIII reaction buffer, 5 μl (~50 units) of restriction enzyme HindIII, and 85 μl of H₂O, and the reaction was incubated at 37° C. for two hours. After the HindIII digestion, the DNA was precipitated, and the DNA pellet was dissolved in 10 μl 10X SalI reaction buffer (1.5M NaCl; 60 mM Tris-HCl, pH=7.9; 60 mM MgCl₂; 60 mM 2-mercaptoethanol; and 1 mg/ml BSA), 5 μl (~50 units) of restriction enzyme SalI, and 85 μl of H₂O. The resulting SalI reaction mixture was incubated for 2 hours at 37° C. The HindIII-SalI-digested plasmid pSV2-HPC8 was loaded onto a 3.5% polyacrylamide gel and electrophoresed until the desired ~0.29 kb HindIII-SalI restriction fragment was separated from the other reaction products. The desired fragment was isolated from the gel; about 2 μg of the fragment were obtained and suspended in 10 μl of TE buffer.

Fifty μg of plasmid pSV2-HPC8 were dissolved in 10 μl of 10X BglII reaction buffer, 5 μl (50 units) of restriction enzyme BglII, and 85 μl of H₂O, and the reaction was incubated at 37° C. for two hours. After the BglII digestion, the DNA was precipitated, and the DNA pellet was dissolved in 10 μl of 10X SalI reaction buffer, 5 μl (~50 units) of restriction enzyme SalI, and 85 μl of H₂O. The resulting SalI reaction mixture was incubated for 2 hours at 37° C. The SalI-BglII-digested plasmid pSV2-HPC8 was loaded onto a 3.5% polyacrylamide gel and electrophoresed until the desired ~1.15 kb SalI-BglII restriction fragment was separated from the other reaction products. The ~1.15 kb SalI-BglII restriction fragment was isolated from the gel; about 8 μg of fragment were obtained and suspended in 10 μl of TE buffer.

Approximately 10 μg of plasmid pSV2-β-globin DNA (NRRL B-15928) were dissolved in 10 μl of 10X HindIII reaction buffer, 5 μl (~50 units) of restriction enzyme HindIII, and 85 μl of H₂O, and the reaction was placed at 37° C. for 2 hours. The reaction mixture was then made 0.25M in NaOAc, and after the addition of two volumes of ethanol and incubation in a dry ice-ethanol bath, the DNA was pelleted by centrifugation. The HindIII-digested plasmid pSV2-β-globin was dissolved in 10 μl of 10X BglII buffer, 5 μl (~50 units) of restriction enzyme BglII, and 85 μl of H₂O, and the reaction was placed at 37° C. for two hours. After the BglII digestion, the reaction mixture was loaded onto a 1% agarose gel, and the fragments were separated by electrophoresis. The desired ~4.2 kb HindIII-BglII restriction fragment was isolated from the gel; about 5 μg of the desired fragment were obtained and suspended in 10 μl of TE buffer.

Two μl of the ~0.29 kb HindIII-SalI fragment of plasmid pSV2-HPC8, 2 μl of the ~1.15 kb SalI-BglII fragment of plasmid pSV2-HPC8, and 2 μl of the ~4.2 kb HindIII-BglII fragment of plasmid pSV2-β-globin were mixed together and ligated in substantial accordance with the procedure of Example 16A. The ligated DNA constituted the desired plasmid pL133. The desired *E. coli* K12 RR1/pL133 transformants were constructed in substantial accordance with the teaching of Example 16A, with the exception that plasmid pL133, rather than plasmid pSV2-HPC8, was used as the transforming DNA.

EXAMPLE 17

Construction of Plasmid pLPC

About 20 μg of plasmid pBLcat DNA were dissolved in 10 μl of 10X HindIII buffer and 80 μl of H₂O. About 10 μl (~100 units) of restriction enzyme HindIII were added to the solution of plasmid pBLcat DNA, and the resulting reaction was incubated at 37° C. for 2 hours. The HindIII-digested plasmid pBLcat DNA was loaded onto an agarose gel and electrophoresed until the ~0.87 kb HindIII restriction fragment that comprises the BK enhancer and Ad2 late promoter was separated from the other digestion products; then, the ~0.87 kb fragment was isolated and prepared for ligation in substantial accordance with the procedure of Example 15A. About 2 μg of the desired fragment were obtained and dissolved in 5 μl of TE buffer.

About 1.5 μg of plasmid pL133 DNA was dissolved in 2 μl of 10X HindIII buffer and 16 μl of H₂O. About 1 μl (~10 units) of restriction enzyme HindIII was added to the solution of DNA, and the resulting reaction was incubated at 37° C. for 2 hours. The DNA was then diluted to 100 μl with TE buffer and treated with calf-intestinal alkaline phosphatase in substantial accordance with the procedure in Example 12. The HindIII-digested plasmid pL133 DNA was extracted twice with phenol and once with chloroform, precipitated with ethanol, and resuspended in 10 μl of TE buffer.

About 5 μl of the ~0.87 kb HindIII restriction fragment of plasmid pBLcat were added to the 1.5 μl of HindIII-digested plasmid pL133, and then, 1 μl of 10X ligase buffer, 1 μl (~1000 units) of T4 DNA ligase, and 1.5 μl of H₂O were added to the solution of DNA, and the resulting reaction was incubated at 16° C. overnight. The ligated DNA constituted the desired plasmid pLPC.

The ligated DNA was used to transform *E. coli* K12 HB101 in substantial accordance with the procedure of Example 3. The transformed cells were plated on L agar containing ampicillin, and the plasmid DNA of the ampicillin-resistant transformants was examined by restriction enzyme analysis to identify the *E. coli* K12 HB101/pLPC transformants. The ~0.87 kb HindIII restriction fragment that encodes the BK enhancer and Ad2 late promoter could insert into HindIII-digested plasmid pL133 in one of two orientations, only the construction which contains an ~1.0 kb NdeI-StuI fragment yields pLPC.

EXAMPLE 18

Construction of Plasmids pLPChyg1 and pLPChyg

E. coli K12 RR1/pSV2hyg cells are obtained from the Northern Regional Research Laboratory under the accession number NRRL B-18039. Plasmid pSV2hyg DNA is obtained from the cells in substantial accordance with the procedure of Example 1.

About 10 μg (in 10 μl of TE buffer) of plasmid pSV2hyg were added to 2 μl of 10X BamHI buffer and 6 μl of H$_2$O. About 2 μl (about 20 units) of restriction enzyme BamHI were added to the solution of DNA, and the resulting reaction was incubated at 37° C. for 2 hours. The reaction was extracted first with phenol and then was extracted twice with chloroform. The BamHI-digested plasmid pSV2hyg DNA was loaded onto an agarose gel, and the hygromycin resistance gene-containing, ~2.5 kb restriction fragment was isolated in substantial accordance with the procedure described in Example 15A.

About 5 μl of 10X Klenow buffer (0.2 mM in each of the four dNTPs; 0.5M Tris-HCl, pH=7.8; 50 mM MgCl$_2$; 0.1M 2-mercaptoethanol; and 100 μg/ml BSA) and 35 μl of H$_2$O were added to the solution of BamHI-digested plasmid pSV2hyg DNA, and then, about 25 units of Klenow enzyme (about 5 μl, as marketed by BRL) were added to the mixture of DNA, and the resulting reaction was incubated at 16° C. for 30 minutes. The Klenow-treated, BamHI-digested plasmid pSV2hyg DNA was extracted once with phenol and once with chloroform and then precipitated with ethanol. About 2 μg of the desired fragment were obtained and suspended in 5 μl of TE buffer.

About 10 μg (10 μl) of plasmid pLPC DNA were added to 2 μl of 10X StuI buffer and 6 μl of H$_2$O. About 2 μl (~10 units) of restriction enzyme StuI were added to the solution of DNA, and the resulting reaction was incubated at 37° C. for 2 hours. The StuI-digested plasmid pLPC DNA was precipitated with ethanol, collected by centrifugation, and resuspended in 2 μl of 10X NdeI buffer (1.5M NaCl; 0.1M Tris-HCl, pH=7.8; 70 mM MgCl$_2$; 60 mM 2-mercaptoethanol; and 1 mg/ml BSA) and 16 μl of H$_2$O. About 2 μl (~10 units) of restriction enzyme NdeI were added to the solution of StuI-digested DNA, and the resulting reaction was incubated at 37° C. for 2 hours.

The NdeI-StuI-digested plasmid pLPC DNA was precipitated with ethanol, collected by centrifugation, and resuspended in 5 μl of 10X Klenow buffer and 40 μl of H$_2$O. About 5 μl (~25 units) of Klenow enzyme were added to the solution of DNA, and the resulting reaction was incubated at 16° C. for 30 minutes. After the Klenow reaction, the reaction mixture was loaded onto an agarose gel, and the ~5.82 kb NdeI-StuI restriction fragment was isolated from the gel. About 5 μg of the desired fragment were obtained and suspended in 5 μl of TE buffer.

About 2 μl of the ~2.5 kb Klenow-treated BamHI restriction fragment of plasmid pSV2hyg were mixed with about 1 μl of the ~5.82 kb Klenow-treated NdeI-StuI restriction fragment of plasmid pLPC, and about 3 μl of 10X ligase buffer, 2 μl of T4 DNA ligase (~1000 units), 1 μl of T4 RNA ligase (~1 unit), and 14 μl of H$_2$O were added to the solution of DNA. The resulting reaction was incubated at 16° C. overnight. The ligated DNA constituted the desired plasmids pLPChyg1 and pLPChyg2, which differ only with respect to the orientation of the ~2.5 kb Klenow-treated, BamHI restriction fragment of plasmid pSV2hyg. The ligated DNA was used to transform E. coli K12 HB101 in substantial accordance with the procedure of Example 3. The desired E. coli K12 HB101/pLPChyg1 and E. coli K12 HB101/pLPChyg2 transformants were plated on L agar containing ampicillin and identified by restriction enzyme analysis of their plasmid DNA.

EXAMPLE 19

Construction of Plasmid pBW32

A. Construction of Intermediate Plasmid pTPA103

Plasmid pTPA102 comprises the coding sequence of human tissue plasminogen activator (TPA). Plasmid pTPA102 can be isolated from E. coli K12 MM294/pTPA102, a strain available from the Northern Regional Research Laboratory under the accession number NRRL B-15834. Plasmid pTPA102 DNA is isolated from E. coli K12 MM294/pTPA102 in substantial accordance with the procedure of Example 1.

About 50 μg of plasmid pTPA102 (in about 50 μl of TE buffer) were added to 10 μl of 10X Tth111I buffer (0.5M NaCl; 80 mM Tris-HCl, pH=7.4; 80 mM MgCl$_2$; 80 mM 2-mercaptoethanol; and 1 mg/ml BSA) and 80 μl of H$_2$O. About 10 μl (~50 units) of restriction enzyme Tth111I were added to the solution of DNA, and the resulting reaction was incubated at 65° C. for 2 hours. The reaction mixture was loaded onto an agarose gel, and the ~4.4 kb Tth111I restriction fragment that comprises the TPA coding sequence was isolated from the gel. The other digestion products, 3.1 kb and 0.5 kb restriction fragments, were discarded. About 10 μg of the desired ~4.4 kb Tth111I restriction fragment were obtained and suspended in 10 μl of TE buffer.

About 5 μl of 10X Klenow buffer and 30 μl of H$_2$O were added to the solution comprising the ~4.4 kb Tth111I restriction fragment, and after the further addition of about 5 μl of Klenow enzyme (~5 units), the reaction mixture was incubated at 16° C. for 30 minutes. After the Klenow reaction, the DNA was precipitated with ethanol and resuspended in 3 μl of 10X ligase buffer and 14 μl of H$_2$O.

BamHI linkers (New England Biolabs), which had the following sequence:

were kinased and prepared for ligation by the following procedure. Four μl of linkers (~2 μg) were dissolved in 20.15 μl of H$_2$O and 5 μl of 10X kinase buffer (500 mM Tris-HCl, pH=7.6 and 100 mM MgCl$_2$), incubated at 90° C. for two minutes, and then cooled to room temperature. Five μl of γ-$^{32}$P-ATP (~20 μCi), 2.5 μl of 1M DTT, and 5 μl of polynucleotide kinase (~10 units) were added to the mixture, which was then incubated at 37° C. for 30 minutes. Then, 3.35 μl of 0.01M ATP and 5 μl of kinase were added, and the reaction was continued for another 30 minutes at 37° C. The radioactive ATP aids in determining whether the linkers have ligated to the target DNA.

About 10 μl of the kinased BamHI linkers were added to the solution of ~4.4 kb Tth111I restriction fragment, and after the addition of 2 μl of T4 DNA ligase (~1000 units) and 1 μl of T4 RNA ligase (~2 units), the ligation reaction was incubated overnight at 4° C. The ligated DNA was precipitated with ethanol and resuspended in 5 µl of 10X HindIII buffer and 40 µl of H₂O. About 5 µl (~50 units) of restriction enzyme HindIII were added to the solution of DNA, and the resulting reaction was incubated at 37° C. for 2 hours.

The HindIII-digested DNA was precipitated with ethanol and resuspended in 10 µl of 10X BamHI buffer and 90 µl of H₂O. About 10 µl (~100 units) of restriction enzyme BamHI were added to the solution of DNA, and the resulting reaction was incubated at 37° C. for 2 hours. After the BamHI digestion, the reaction mixture was loaded onto an agarose gel, and the ~2.0 kb BamHI-HindIII restriction fragment was isolated from the gel. About 4 µg of the desired fragment were obtained and suspended in about 5 µl of TE buffer.

To construct plasmid pTPA103, the ~2.0 kb BamHI-HindIII restriction fragment derived from plasmid pTPA102 was inserted into BamHI-HindIII-digested plasmid pRC. Plasmid pRC was constructed by inserting an ~288 bp EcoRI-ClaI restriction fragment that comprises the promoter and operator (trpPO) sequences of the *E. coli* trp operon into EcoRI-ClaI-digested plasmid pKC7. Plasmid pKC7 can be obtained from the American Type Culture Collection in *E. coli* K12 N100/pKC7 under the accession number ATCC 37084. The ~288 bp EcoRI-ClaI restriction fragment that comprises the trpPO can be isolated from plasmid pTPA102, which can be isolated from *E. coli* K12 MM294/pTPA102 (NRRL B-15834). Plasmid pKC7 and plasmid pTPA102 DNA can be obtained from the aforementioned cell lines in substantial accordance with the procedure of Example 1. This ~0.29 kb EcoRI-ClaI restriction fragment of plasmid pTPA102 comprises the transcription activating sequence and most of the translation activating sequence of the *E. coli* trp gene and has the sequence depicted below:

10X EcoRI buffer and 16 µl of H₂O. About 2 µl (~10 units) of restriction enzyme EcoRI were added to the solution of ClaI-digested plasmid pKC7 DNA, and the resulting reaction was incubated at 37° C. for 2 hours.

The EcoRI-ClaI-digested plasmid pKC7 DNA was extracted once with phenol and then twice with chloroform. The DNA was then precipitated with ethanol and resuspended in 3 µl of 10X ligase buffer and 20 µl of H₂O. A restriction site and function map of plasmid pKC7 can be obtained from Maniatis et al., *Molecular Cloning* (Cold Spring Harbor Laboratory, 1982), page 8.

About 20 µg of plasmid pTPA102 in about 20 µl of TE buffer were added to 10 µl of 10X ClaI buffer and 60 µl of H₂O. About 10 µl (~50 units) of restriction enzyme ClaI were added to the solution of plasmid pTPA102 DNA, and the resulting reaction was incubated at 37° C. for 2 hours. The ClaI-digested plasmid pTPA102 DNA was precipitated with ethanol and resuspended in 10 µl of 10X EcoRI buffer and 80 µl of H₂O. About 10 µl (~50 units) of restriction enzyme EcoRI were added to the solution of ClaI-digested plasmid pTPA102 DNA, and the resulting reaction was incubated at 37° C. for 2 hours.

The EcoRI-ClaI-digested plasmid pTPA102 DNA was extracted once with phenol loaded onto a 7% polyacrylamide gel, and electrophoresed until the ~288 bp EcoRI-ClaI restriction fragment that comprises the trpPO was separated from the other digestion products. The ~288 bp EcoRI-ClaI restriction fragment was isolated from the gel; about 1 µg of the desired fragment was obtained, suspended in 5 µl of TE buffer, and added to the solution of EcoRI-ClaI-digested plasmid pKC7 DNA prepared as described above. About 2 µl (~1000 units) of T4 DNA ligase were then added to the mixture

```
            10         20         30         40         50
5'-AATTCACGCT GTGGTGTTAT GGTCGGTGGT CGCTAGGGTG CCGACGCGCA
   |||||| |||||||||| |||||||||| |||||||||| ||||||||||
3'-GTGCGA CACCACAATA CCAGCCACCA GCGATCCCAC GGCTGCGCGT 60         70         80         90        100
   TCTCGACTGC ACGGTGCACC AATGCTTCTG GCGTCAGGCA GCCAATCGGA
   |||||||||| |||||||||| |||||||||| |||||||||| ||||||||||
   AGAGCTGACG TGCCACGTGG TTACGAAGAC CGCAGTCCGT CGGTTAGCCT 110        120        130        140        150
   AGCTGTGGTA TGGCTGTGCA GGTCGTATAA TCACCGCATA ATTCGAGTCG
   |||||||||| |||||||||| |||||||||| |||||||||| ||||||||||
   TCGACACCAT ACCGACACGT CCAGCATATT AGTGGCGTAT TAAGCTCAGC 160        170        180        190        200
   CTCAAGGCGC ACTCCCGTTC CGGATAATGT TTTTTGCTCC GACATCATAA
   |||||||||| |||||||||| |||||||||| |||||||||| ||||||||||
   GAGTTCCGCG TGAGGGCAAG GCCTATTACA AAAAACGAGG CTGTAGTATT 210        220        230        240        250
   CGGTTCCGGC AAATATTCTG AAATGAGCTG TTGACAATTA ATCATCGAAC
   |||||||||| |||||||||| |||||||||| |||||||||| ||||||||||
   GCCAAGGCCG TTTATAAGAC TTTACTCGAC AACTGTTAAT TAGTAGCTTG 260        270        280    287
   TAGTTAACTA GTACGCAAGT TCTCGTAAAA AGGGTAT-3'
   |||||||||| |||||||||| |||||||||| ||||||||
   ATCAATTGAT CATGCGTTCA AGAGCATTTT TCCCATAGC-5'
```

Thus, to construct plasmid pRC, about 2 µg of plasmid pKC7 in 10 µl of TE buffer were added to 2 µl of 10X ClaI buffer (0.5M NaCl; 60 mM Tris-HCl, pH=7.9, 60 mM MgCl₂; and 1 mg/ml BSA) and 6 µl of H₂O. About 2 µl (~10 units) of restriction enzyme ClaI were added to the solution of plasmid pKC7 DNA, and the resulting reaction was incubated at 37° C. for 2 hours. The ClaI-digested plasmid pKC7 DNA was precipitated with ethanol and resuspended in 2 µl of of DNA, and the resulting ligation reaction was incubated at 16° C. for 2 hours. The ligated DNA constituted the desired plasmid pRC DNA.

The ligated DNA was used to transform *E. coli* K12 HB101 competent cells in substantial accordance with the procedure of Example 2. The transformed cells were plated on L agar containing 100 µg/ml ampicillin, and the ampicillin-resistant transformants were screened by restriction enzyme analysis of their plasmid DNA to identify the desired *E. coli* K12 HB101/pRC colonies. Plasmid pRC DNA was obtained from the *E. coli* K12 HB101/pRC transformants in substantial accordance with the procedure of Example 1.

About 2 μg of plasmid pRC DNA in 2 μl of TE buffer were added to 2 μl of 10X HindIII buffer and 16 μl of H₂O. About 2 μl (~10 units) of restriction enzyme HindIII were added to the solution of plasmid pRC DNA, and the resulting reaction was incubated at 37° C. for two hours. The HindIII-digested plasmid pRC DNA was precipitated with ethanol and resuspended in 2 μl of 10X BamHI buffer and 16 μl of H₂O. About 2 μl (~10 units) of restriction enzyme BamHI were added to the solution of HindIII-digested plasmid pRC DNA, and the resulting reaction was incubated at 37° C. for 2 hours.

The BamHI-HindIII-digested plasmid pRC DNA was extracted once with phenol and then twice with chloroform. The DNA was precipitated with ethanol and resuspended in 3 μl of 10X ligase buffer and 20 μl of H₂O. The ~4 μg (in ~5 μl of TE buffer) of ~2.0 kb HindIII-BamHI restriction fragment of plasmid pTPA102 were then added to the solution of BamHI-HindIII-digested plasmid pRC DNA. About 2 μl (~1000 units) of T4 DNA ligase were added to the mixture of DNA, and the resulting reaction was incubated at 16° C. for 2 hours. The ligated DNA constituted the desired plasmid pTPA103 DNA.

To reduce undesired transformants, the ligated DNA was digested with restriction enzyme NcoI, which cuts plasmid pRC but not plasmid pTPA103. Thus, digestion of the ligated DNA with NcoI reduces undesired transformants, because linearized DNA transforms *E. coli* at a lower frequency than closed, circular DNA. To digest the ligated DNA, the DNA was first precipitated with ethanol and then resuspended in 2 μl of 10X NcoI buffer (1.5M NaCl; 60 mM Tris-HCl, pH=7.8; 60 mM MgCl₂; and 1 mg/ml BSA) and 16 μl of H₂O. About 2 μl (~10 units) of restriction enzyme NcoI were added to the solution of DNA, and the resulting reaction was incubated at 37° C. for 2 hours.

The ligated and then NcoI-digested DNA was used to transform *E. coli* K12 RV308 (NRRL B-15624). *E. coli* K12 RV308 cells were made competent and transformed in substantial accordance with the procedure of Example 3. The transformation mixture was plated on L agar containing 100 μg/ml ampicillin. The ampicillin-resistant transformants were tested for sensitivity to kanamycin, for though plasmid pRC confers kanamycin resistance, plasmid pTPA103 does not. The ampicillin-resistant, kanamycin-sensitive transformants were then used to prepare plasmid DNA, and the plasmid DNA was examined by restriction enzyme analysis to identify the *E. coli* K12 RV308/pTPA103 transformants. Plasmid pTPA103 DNA was isolated from the *E. coli* K12 RV308/pTPA103 cells in substantial accordance with the procedure of Example 1.

B. Construction of Intermediate Plasmid pBW25

About 1 μg of plasmid pTPA103 DNA in 1 μl of TE buffer was added to 2 μl of 10X BglII buffer and 16 μl of H₂O. About 1 μl (~5 units) of restriction enzyme BglII was added to the solution of plasmid pTPA103 DNA, and the resulting reaction was incubated at 37° C. for 2 hours. The BglII-digested plasmid pTPA103 DNA was precipitated with ethanol and resuspended in 5 μl of 10X Klenow buffer and 44 μl of H₂O. About 1 μl of Klenow enzyme (~1 unit) was added to the solution of BglII-digested plasmid pTPA103 DNA, and the resulting reaction was incubated at 16° C. for 2 hours. The Klenow-treated, BglII-digested plasmid pTPA103 DNA was precipitated with ethanol and resuspended in 3 μl of 10X ligase buffer and 22 μl of H₂O.

About 2 μl (0.2 μg) of unkinased NdeI linkers (New England Biolabs) of sequence:

were added to the solution of Klenow-treated, BglII-digested plasmid pTPA103 DNA, together with 2 μl (~1000 units) of T4 DNA ligase and 1 μl (~2 units) of T4 RNA ligase, and the resulting ligation reaction was incubated at 4° C. overnight. The ligated DNA constituted plasmid pTPA103derNdeI, which is substantially similar to plasmid pTPA103, except plasmid pTPA10-3derNdeI has an NdeI recognition sequence where plasmid pTPA103 has a BglII recognition sequence.

The ligated DNA was used to transform *E. coli* K12 RV308 competent cells in substantial accordance with the procedure described in Example 2. The transformed cells were plated on L-agar containing ampicillin, and the *E. coli* K12 RV308/pTPA103derNdeI transformants were identified by restriction enzyme analysis of their plasmid DNA. Plasmid pTPA103derNdeI DNA was isolated from the transformants for use in subsequent constructions in substantial accordance with the procedure of Example 1.

About 10 μg of plasmid pTPA103derNdeI DNA in 10 μl of TE buffer were added to 2 μl of 10X AvaII buffer (0.6M NaCl; 60 mM Tris-HCl, pH=8.0; 0.1M MgCl₂; 60 mM 2-mercaptoethanol; and 1 mg/ml BSA) and 6 μl of H₂O. About 2 μl (~10 units) of restriction enzyme AvaII were added to the DNA, and the resulting reaction was incubated at 37° C. for 2 hours. The AvaII-digested DNA was loaded onto an agarose gel and electrophoresed until the ~1.4 kb restriction fragment was separated from the other digestion products. The ¾1.4 kb AvaII restriction fragment of plasmid pTPA103derNdeI was isolated from the gel; about 2 μg of the desired fragment were obtained and suspended in 5 μl of TE buffer.

About 5 μl of 10X Klenow buffer, 35 μl of H₂O, and 5 μl (~5 units) of Klenow enzyme were added to the solution of ~1.4 kb AvaII restriction fragment, and the resulting reaction was incubated at 16° C. for thirty minutes. The Klenow-treated DNA was precipitated with ethanol and resuspended in 3 μl of 10X ligase buffer and 14 μl of H₂O.

About 2 μg of HpaI linkers of sequence:

were kinased in substantial accordance with the procedure of Example 10A. About 10 μl of the kinased linkers were added to the solution of Klenow-treated, ~1.4 kb AvaII restriction fragment of plasmid PTPA10-3derNdeI together with 2 μl (~1000 units) of T4 DNA ligase and 1 μl (~1 unit) of T4 RNA ligase, and the resulting reaction was incubated at 16° C. overnight.

The ligated DNA was extracted once with phenol, extracted twice with chloroform, precipitated with ethanol, and resuspended in 2 μl of 10X EcoRI buffer and 16 μl of H₂O. About 2 μl (~10 units) of restriction enzyme EcoRI were added to the solution of DNA, and the resulting reaction was incubated at 37° C. for 2 hours. The EcoRI-digested DNA was extracted once with phenol, extracted twice with chloroform, precipitated with ethanol, and resuspended in 3 μl of 10X ligase buffer and 20 μl of H₂O. The fragment, which is about 770 bp in size and encodes the trpPO and the amino-terminus of TPA, thus prepared had one EcoRI-compatible end and one blunt end and was ligated into EcoRI-SmaI-digested plasmid pUC19 to form plasmid pUC19TPAFE.

About 2 μl of plasmid pUC19 (available from Bethesda Research Laboratories) were dissolved in 2 μl of 10X SmaI buffer (0.2M KCl; 60 mM Tris-HCl, pH=8.0; 60 mM MgCl₂; 60 mM 2-mercaptoethanol; and 1 mg/ml BSA) and 16 μl of H₂O. About 2 μl (~10 units) of restriction enzyme SmaI were added to the solution of DNA, and the resulting reaction was incubated at 25° C. for 2 hours. The SmaI-digested plasmid pUC19 DNA was precipitated with ethanol, collected by centrifugation, and resuspended in 2 μl of 10X EcoRI buffer and 16 μl of H₂O. About 2 μl (~10 units) of restriction enzyme EcoRI were added to the solution of SmaI-digested plasmid pUC19 DNA, and the resulting reaction was incubated at 37° C. for 2 hours. The EcoRI-SmaI-digested plasmid pUC19 DNA was extracted once with phenol, extracted twice with chloroform, and resuspended in 5 μl of TE buffer.

The EcoRI-SmaI-digested plasmid pUC19 DNA was added to the solution containing the ~770 bp EcoRI-blunt end restriction fragment derived from plasmid pTPA103derNdeI. About 2 μl (~1000 units) of T4 DNA ligase were added to the mixture of DNA, and the resulting reaction was incubated at 16° C. overnight. The ligated DNA constituted the desired plasmid pUC19TPAFE.

The multiple-cloning site of plasmid pUC19, which comprises the EcoRI and SmaI recognition sequences utilized in the construction of plasmid pUC19TPAFE, is located within the coding sequence for the lacZ α fragment. Expression of the lacZ α fragment in cells that contain the lacZ ΔM15 mutation, a mutation in the lacZ gene that encodes β-galactosidase, allows those cells to express a functional β-galactosidase molecule and thus allows those cells to hydrolyze X-Gal (5-bromo-4-chloro-3-indolyl-β-D-galactopyranoside), a colorless compound, to its indigo-colored hydrolysis product. Insertion of DNA into the multiple-cloning site of plasmid pUC19 interrupts the coding sequence for the lacZ α fragment, and cells with the lacZ ΔM15 mutation that host such a plasmid are unable to hydrolyze X-Gal. The ligated DNA that constituted plasmid pUC19TPAFE was used to transform $E.$ $coli$ K12 RR1ΔM15 (NRRL B-15440) cells made competent for transformation in substantial accordance with the procedure of Example 3.

The transformed cells were plated on L agar containing 100 Mg/ml ampicillin; 40 Mg/ml X-Gal; and 1 mM IPTG. Colonies that failed to exhibit the indigo color were subcultured and used to prepare plasmid DNA; the $E.$ $coli$ K12 RR1ΔAM15/pUC19TPAFE transformants were identified by restriction enzyme analysis of their plasmid DNA. Plasmid pUC19TPAFE DNA was isolated from the $E.$ $coli$ K12 RR1ΔM15/pUC19-TPAFE cells for use in subsequent constructions in substantial accordance with the procedure of Example 1.

About 7 Mg of plasmid pUC19TPAFE in 20 μl of TE buffer were added to 10 μl of 10X HpaI buffer (0.2M KCl; 0.1M Tris-HCl, pH=7.4; and 0.1M MgCl₂) and 70 μl of H₂O. About 3 μl (~6 units) of restriction enzyme HpaI were added to the solution of plasmid pUC19-TPAFE DNA, and the resulting reaction was incubated at 37° C. for 20 minutes; the short reaction period was designed to yield a partial HpaI digest. The reaction was adjusted to 150 μl of 1X BamHI buffer (150 mM NaCl; 10 mM Tris-HCl, pH=8.0; and 10 mM MgCl₂; raising the salt concentration inactivates HpaI). About 1 μl (~16 units) of restriction enzyme BamHI were added to the solution of partially-HpaI-digested DNA, and the resulting reaction was incubated at 37° C. for 90 minutes.

The BamHI-partially-HpaI-digested plasmid pUC19-TPAFE DNA was concentrated by ethanol precipitation loaded onto a 1.5% agarose gel and the ~3.42 kb HpaI-BamHI restriction fragment that comprises the replicon, β-lactamase gene, and all of the TPA-encoding DNA of plasmid pUCATPAFE was isolated from the gel by cutting out the segment of the gel that contained the desired fragment, freezing the segment, and then squeezing the liquid from the segment. The DNA was precipitated from the liquid by an ethanol precipitation. About 1 μg of the desired fragment was obtained and suspended in 20 μl of TE buffer.

About 10 μg of plasmid pTPA103 in 10 μl of TE buffer were dissolved in 10 μl of 10X ScaI buffer (1.0M NaCl; 60 mM Tris-HCl, pH=7.4; and 60 mM MgCl₂) 10 mM DTT; and 1 mg/ml BSA) and 80 μl of H₂O. About 3 μl (~18 units) of restriction enzyme ScaI were added to the solution of plasmid pTPA103 DNA, and the resulting reaction was incubated at 37° C. for 90 minutes. The reaction volume was adjusted to 150 μl of 1X BamHI buffer, and about 1 μl (~16 units) of restriction enzyme BamHI was added to the mixture, which was then incubated at 37° C. for 90 minutes. The DNA was precipitated with ethanol, collected by centrifugation, and resuspended in preparation for electrophoresis. The ScaI-BamHI-digested plasmid pTPA103 DNA was loaded onto a 1.5% agarose gel and electrophoresed until the ~1.015 kb ScaI-BamHI restriction fragment was separated from the other digestion products. The ~1.015 ScaI-BamHI restriction fragment that comprises the TPA carboxy-terminus-encoding DNA of plasmid pTPA103 was isolated from the gel; about 0.5 μg of the desired fragment were obtained and dissolved in 20 μl of glass-distilled H₂O.

About 2 μl of the ~3.42 kb BamHI-HpaI restriction fragment of plasmid pUC19TPAFE were added to 2 μl of the ~1.015 kb ScaI-BamHI restriction fragment of plasmid pTPA103 together with 2 μl of 10X ligase buffer and 1 μl (~1 Weiss unit; the ligase was obtained from Promega Biotec, 2800 S. Fish Hatchery Road, Madison, Wis. 53711) of T4 DNA ligase, and the resulting reaction was incubated at 16° C. overnight. The ligated DNA constituted the desired plasmid pBW25.

The ligated DNA was used to transform $E.$ $coli$ K12 JM105 (available from BRL) that were made competent for transformation in substantial accordance with the procedure of Example 3, except that 50 mM CaCl₂ was used in the procedure. The transformed cells were plated on BHI (Difco Laboratories, Detroit, Mich.) containing 100 μg/ml ampicillin, and the $E.$ $coli$ K12

JM105/pBW25 transformants were identified by restriction enzyme analysis of their plasmid DNA. Digestion of plasmid pBW25 with restriction enzyme EcoRI yields ~3.38 kb and ~1.08 kb restriction fragments. Plasmid pBW25 is prepared for use in subsequent constructions in substantial accordance with the procedure of Example 1.

C. Site-Specific Mutagenesis of the TPA coding Region and Construction of Plasmid pBW28

About 5 μg of plasmid pBW25 in 10 μl of glass-distilled H₂O were added to about 10 μl of 10X HindIII reaction buffer and 80 μl of H₂O. About 1 μl (~20 units) of restriction enzyme HindIII was added to the solution of plasmid pBW25 DNA, and the resulting reaction was incubated at 37° C. for 90 minutes. About 3 μl (~24 units) of restriction enzyme EcoRI and 10 μl of 1M Tris.HCl, pH=7.6, were added to the solution of HindIII-digested plasmid pBW25 DNA, and the resulting reaction was incubated at 37° C. for 90 minutes. The EcoRI-HindIII-digested plasmid pBW25 DNA was concentrated by ethanol precipitation, loaded onto a 1.5% agarose gel, and electrophoresed until the ~810 bp EcoRI-HindIII restriction fragment was separated from the other digestion products. About 0.5 μg of the ~810 bp EcoRI-HindIII restriction fragment was isolated from the gel, prepared for ligation, and resuspended in 20 μl of glass-distilled H₂O.

About 4.5 μg of the replicative form (RF) of M13mp8 DNA (available from New England Biolabs) in 35 μl of glass-distilled H₂O were added to 10 μl of 10X HindIII buffer and 55 μl of H₂O. About 1 μl (~20 units) of restriction enzyme HindIII was added to the solution of M13mp8 DNA, and the resulting reaction was incubated at 37° C. for 1 hour. About 3 μl (~24 units) of restriction enzyme EcoRI and about 10 μl of 1M Tris-HCl, pH=7.6, were added to the solution of HindIII-digested M13mp8 DNA, and the resulting reaction was incubated at 37° C. for 1 hour. The HindIII-EcoRI-digested M13mp8 DNA was collected by ethanol precipitation, resuspended in preparation for agarose gel electrophoresis, and the large restriction fragment isolated by gel electrophoresis. About 1 μg of the large EcoRI-HindIII restriction fragment of M13mp8 was obtained and suspended in 20 μl of glass-distilled H₂O. About 2 μl of the large EcoRI-HindIII restriction fragment of M13mp8, 2 μl of 10X ligase buffer, 12 μl of H₂O and 1 μl (~1 Weiss unit) of T4 DNA ligase were added to 3 μl of the ~810 bp EcoRI-HindIII restriction fragment of plasmid pBW25, and the resulting ligation reaction was incubated at 16° C. overnight.

E. coli JM103 cells, available from BRL, were made competent and transfected with the ligation mix in substantial accordance with the procedure described in the BRL M13 Cloning/'Dideoxy' Sequencing Instruction Manual, except that the amount of DNA used per transfection was varied. Recombinant plaques were identified by insertional inactivation of the β-galactosidase α-fragment-encoding gene, which results in the loss of the ability to cleave X-gal to its indigo-colored cleavage product. For screening purposes, six white plaques were picked into 2.5 ml of L broth, to which was added 0.4 ml of E. coli K12 JM103, cultured in minimal media stock to insure retention of the F episome that carries proAB, in logarithmic growth phase. The plaque-containing solutions were incubated in an air-shaker at 37° C. for 8 hours. Cells from 1.5 ml aliquots were pelleted and RF DNA isolated in substantial accordance with the alkaline miniscreen procedure of Birnboim and Doly, 1979, Nuc. Acids Res. 7:1513. The remainder of each culture was stored at 4° C. for stock. The desired phage, designated pM8BW26, contained the ~810 bp EcoRI-HindIII restriction fragment of plasmid pBW25 ligated to the ~7.2 kb EcoRI-HindIII restriction fragment of M13mp8.

About fifty ml of log phase E. coli JM103 were infected with pM8BW26 and incubated in an air-shaker at 37° C. for 18 hours. The infected cells were pelleted by low speed centrifugation, and single-stranded pM8BW26 DNA was prepared from the culture supernatant by scaling up the procedure given in the Instruction manual. Single-stranded pM8BW26 was mutagenized in substantial accordance with the teaching of Adelman et al., 1983, DNA 2(3): 183–193, except that the Klenow reaction was done at room temperature for 30 minutes, then at 37° C. for 60 minutes, then at 10° C. for 18 hours. In addition, the S1 treatment was done at 20° C., the salt concentration of the buffer was one-half that recommended by the manufacturer, and the M13 sequencing primer (BRL) was used. The synthetic oligodeoxyribonucleotide primer used to delete the coding sequence for amino acid residues 87 through 261 of native TPA was

5'-
GGGAAGTGCTGTGAAATATCCACCTGCGGCCTGAGA-
3'.

The resulting mutagenesis mix was used to transfect E. coli K12 JM103 in substantial accordance with the infection procedure described above. Desired mutants were identified by restriction enzyme analysis of RF DNA and by Maxam and Gilbert DNA sequencing. The desired mutant, which had the coding sequence for amino acid residues 87 through 261 of native TPA deleted, was designated pM8BW27.

To construct plasmid pBW28, a variety of DNA fragments are needed. The first of these fragments was obtained by adding ~20 μg of RF pM8BW27 DNA in 20 μl of glass-distilled H₂O to 10 μl of 10X NdeI buffer and 60 μl of H₂O. About 10 μl (~50 units) of restriction enzyme NdeI were added to the mixture of plasmid pM8BW27 DNA, and the resulting reaction was incubated at 37° C. for two hours. The NdeI-digested plasmid pM8BW27 DNA was precipitated with ethanol, collected by centrifugation, and resuspended in 10 μl of 10X EcoRI buffer and 90 μl of H₂O. About 10 μl (~50 units) of restriction enzyme EcoRI were added to the solution of NdeI-digested plasmid pM8BW27 DNA, and the resulting reaction was incubated at 37° C. for 2 hours. The EcoRI-NdeI-digested plasmid pM8BW27 DNA was electrophoresed on an agarose gel until the ~560 bp NdeI-EcoRI restriction fragment, which contains the portion of TPA coding sequence that spans the site of deletion, was separated from the other digestion products. The ~560 bp NdeI-EcoRI restriction fragment was isolated from the gel; about 0.5 μg of the desired fragment was obtained and suspended in 20 μl of glass-distilled H₂O.

The second fragment needed to construct plasmid pBW28 is synthesized one strand at a time on an automated DNA synthesizer. The two complementary strands, which will hybridize to form a double-stranded DNA segment with XbaI and NdeI overlaps, are kinased and annealed in substantial accordance with the procedure of Example 2. The linker has the following structure:

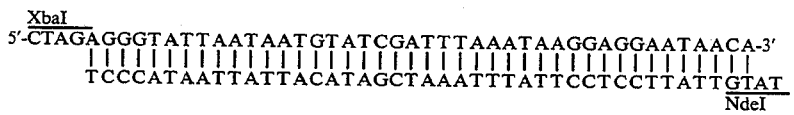

The third fragment needed to construct plasmid pBW28 was prepared by adding ~20 μg of plasmid pTPA103 in 20 μl of TE buffer to 10 μl of 10X BamHI buffer and 60 μl of H₂O. About 10 μl (~50 units) of restriction enzyme BamHI were added to the solution of plasmid pTPA103 DNA, and the resulting reaction was incubated at 37° C. for 2 hours. The BamHI-digested plasmid pTPA103 DNA was precipitated with ethanol, collected by centrifugation, and resuspended in 10 μl of 10X EcoRI buffer and 80 μl of H₂O. About 10 μl (~50 units) of restriction enzyme EcoRI were added to the solution of BamHI-digested plasmid pTPA103 DNA, and the resulting reaction was incubated at 37° C. for 2 hours. The BamHI-EcoRI-digested plasmid pTPA103 DNA was loaded onto an agarose gel and electrophoresed until the ~689 bp EcoRI-BamHI restriction fragment, which comprises the coding sequence for the carboxy-terminus of TPA, was separated from the other digestion products. About 0.5 μg of the ~689 bp fragment was isolated from the gel and then resuspended in 10 μl of glass-distilled H₂O.

The final fragment necessary to construct plasmid pBW28 was isolated from plasmid pL110, the construction of which was disclosed in Example 9. About 25 μg of plasmid pL110 in 25 μl of TE buffer were added to 10 μl of 10X XbaI buffer (0.5M NaCl; 60 mM Tris-HCl, pH=7.9; 60 mM MgCl₂; and 1 mg/ml BSA) and 55 μl of H₂O. About 10 μl (~50 units) of restriction enzyme XbaI were added to the solution of plasmid pL110 DNA, and the resulting reaction was incubated at 37° C. for 2 hours. The XbaI-digested plasmid pL110 DNA was precipitated with ethanol, collected by centrifugation, and resuspended in 10 μl of 10X BamHI buffer and 89 μl of H₂O. About 1 μl (~5 units) of restriction enzyme BamHI was added to the solution of XbaI-digested plasmid pL110 DNA, and the resulting reaction was incubated at 37° C. for 30 minutes to obtain a partial BamHI digest. The XbaI-partially-BamHI-digested plasmid pL110 DNA was loaded onto an agarose gel and electrophoresed until the ~6.0 kb XbaI-BamHI fragment was clearly separated from the other digestion products. The ~6.0 kb restriction fragment was isolated from the gel; about 0.5 μg of the ~6.0 kb XbaI-BamHI restriction fragment was obtained and suspended in about 40 μl of glass-distilled H₂O. This ~6.0 kb XbaI-BamHI restriction fragment comprises all of plasmid pL110 except the EK-BGH-encoding DNA.

To construct plasmid pBW28, the following fragments are mixed together: about 0.1 μg (~8 μl) of the ~6.0 kb BamHI-XbaI restriction fragment of plasmid pL110; about 0.05 μg (~2 μl) of the ~560 bp NdeI-EcoRI restriction fragment of plasmid pM8BW27; about 0.1 μg (~2 μl) of the ~689 bp EcoRI-BamHI restriction fragment of pTPA103; and about 0.02 μg (~1 μl) of the ~45 bp XbaI-NdeI synthetic linker. About 2 μl of 10X ligase buffer and 1 μl (~1 Weiss unit) of T4 DNA ligase are added to the mixture of DNA, and the resulting ligation reaction is incubated at 4° C. overnight. The ligated DNA constituted the desired plasmid pBW28.

The ligated DNA was used to transform E. coli K12 MM294 (NRRL B-15625) made competent in substantial accordance with the procedure of Example 3, except that 50 mM CaCl₂ was used in the procedure. Due to the presence of the lambda pL promoter and the gene encoding the temperature-sensitive lambda pL repressor on plasmid pBW28, the transformation procedure and culturing of transformants were varied somewhat. The cells were not exposed to temperatures greater than 32° C. during transformation and subsequent culturing. The desired E. coli K12 MM294/pBW28 transformants were identified by their tetracycline-resistant, ampicillin-sensitive phenotype and by restriction enzyme analysis of their plasmid DNA.

D. Final Construction of Plasmid pBW32

Approximately 10 μg of plasmid pSV2-β-globin DNA (NRRL B-15928) were dissolved in 10 μl 10X HindIII reaction buffer, 5 μl (~50 units) restriction enzyme HindIII, and 85 μl H₂O, and the reaction was placed at 37° C. for 2 hours. The reaction mixture was then made 0.15M in LiCl, and after the addition of 2.5 volumes of ethanol and incubation in a dry ice-ethanol bath, the DNA was pelleted by centrifugation.

The DNA pellet was dissolved in 10 μl 10X BglII buffer, 5 μl (~50 units) restriction enzyme BglII, and 85 μl H₂O, and the reaction was placed at 37° C. for two hours. After the BglII digestion, the reaction mixture was loaded onto a 0.85% agarose gel and the fragments were separated by electrophoresis. The gel was visualized using ethidium bromide and ultraviolet light, and the band containing the desired ~4.2 kb HindIII-BglII fragment was excised from the gel as previously described. The pellet was resuspended in 10 μl of H₂O and constituted ~5 μg of the desired ~4.2 kb HindIII-BglII restriction fragment of plasmid pSV2 -β-globin. The ~2.0 kb HindIII-BamHI restriction fragment of plasmid pTPA103 that encodes TPA was isolated from plasmid pTPA103 in substantial accordance with the foregoing teaching. About 5 μg of the ~2.0 kb HindIII-BamHI restriction fragment of plasmid pTPA103 were obtained, suspended in 10 μl of H₂O, and stored at −20° C.

Two μl of the ~4.2 kb BglII-HindIII restriction fragment of plasmid pSV2-β-globin and 4 μl of the ~2.0 kb HindIII-BamHI fragment of plasmid pTPA103 were mixed together and then incubated with 2 μl of 10X ligase buffer, 11 μl of H₂O, and 1 μl of T4 DNA ligase (~500 units) at 4° C overnight. The ligated DNA constituted the desired plasmid pTPA301. The ligated DNA was used to transform E. coli K12 RR1 cells (NRRL B-15210) made competent for transformation in substantial accordance with the teaching of Example 3. Plasmid DNA was obtained from the E. coli K12 RR1/pTPA301 transformants in substantial accordance with the procedure of Example 1.

Plasmid pSV2-dhfr comprises a dihydrofalate reductase (dhfr) gene useful for selection of transformed eukaryotic cells and amplification of DNA covalently linked to the dhfr gene. Ten μg of plasmid pSV2-dhfr (isolated from *E. coli* K12 HB101/pSV2-dhfr, ATCC 37146) were mixed with 10 μl 10X PvuII buffer, 2 μl (~20 units) PvuII restriction enzyme, and 88 μl of H$_2$O, and the resulting reaction was incubated at 37° C. for two hours. The reaction was terminated by phenol and chloroform extractions, and then, the PvuII-digested plasmid pSV2-dhfr DNA was precipitated and collected by centrifugation.

BamHI linkers (5'-CGGATCCCG-3') were kinased and prepared for ligation by the following procedure. To 1 μg of linker in 5 μl H$_2$O was added: 10 μl 5X Kinase salts (300 mM Tris-HCl, pH=7.8; 50 mM MgCl$_2$; and 25 mM DTT), 5 μl of 5 mM ATP, 5 μl of BSA (1 mg/ml), 5 μl of 10 mM spermidine, 19 μl of H$_2$O, and 1 μl of poly-nucleotide Kinase (10 units/μl). This reaction was then incubated at 37° for 60 minutes and stored at −20° C. Five μl (~5 μg) of the PvuII-digested plasmid pSV2-dhfr and 12 μl (~0.25 μg) of the kinased BamHI linkers were mixed and incubated with 11 μl of H$_2$O, 2 μl 10X ligase buffer, and 1 μl (~1000 units) of T4 DNA ligase at 16° C. overnight.

Ten μl of 10X BamHI reaction buffer, 10 μl (~50 units) of BamHI restriction enzyme, and 48 μl of H$_2$O were added to the ligation reaction mixture, which was then-incubated at 37° C. for 3 hours. The reaction was loaded onto a 1% agarose gel, and the desired ~1.9 kb fragment, which comprises the dhfr gene, was isolated from the gel. All linker additions performed in these examples were routinely purified on an agarose gel to reduce the likelihood of multiple linker sequences in the final vector. The ~3 μg of fragment obtained were suspended in 10 μl of TE buffer.

Next, approximately 15 μl (~1 μg) of plasmid pTPA301 were digested with BamHI restricton enzyme as taught above. Because there is a unique BamHI site in plasmid pTPA301, this BamHI digestion generates linear plasmid pTPA301 DNA. The BamHI-digested plasmid pTPA301 was precipitated with ethanol and resuspended in 94 μl of H$_2$O and phosphatased using 1 μl of Calf-Intestinal Alkaline Phosphatase (Collaborative Research, Inc., 128 Spring Street, Lexington, Mass. 02173), and 5 μl of 1M Tris-HCl, pH=9.0, at 65° C. for 45 min. The DNA was extracted with phenol:-chloroform, then extracted with chloroform:isoamyl alcohol, ethanol precipitated, and resuspended in 20 μl H$_2$O. Ten μl (~0.25 g) of phosphatased plasmid pTPA301 were added to 5 μl of the BamHI, dhfr-gene-containing restriction fragment (~1.5 μg), 3 μl of 10X ligase buffer, 3 μl (~1500 units) of T4 DNA ligase, and 9 μl H$_2$O. This ligation reaction was incubated at 15° C. overnight; the ligated DNA constituted the desired plasmid pTPA303 DNA.

Plasmid pTPA303 was used to transform *E. coli* K12 RR1 (NRRL B-15210), and the resulting *E. coli* K12 RR1/pTPA303 transformants were identified by their ampicillin-resistant phenotype and by restriction enzyme analysis of their plasmid DNA. Plasmid pTPA303 was isolated from the transformants in substantial accordance with the procedure of Example 1.

To isolate the ~2.7 kb EcoRI-BglII restriction fragment that encodes the pBR322 replicon and β-lactamase gene from plasmid pTPA301, about 10 μg of plasmid pTPA301 are digested to completion in 400 μl total reaction volume with 20 units BglII restriction enzyme in 1X BglII buffer at 37° C.. After the BglII digestion, the Tris-HCl concentration is adjusted to 110 mM, and 20 units of EcoRI restriction enzyme are added to the BglII-digested DNA. This reaction is allowed to incubate at 37° C. for 2 hours. The EcoRI-BglII-digested DNA is loaded onto an agarose gel and electrophoresed until the ~2.7 kb EcoRI-BglII restriction fragment is separated from the other digestion products, and then, the ~2.7 kb fragment is isolated and prepared for ligation.

To isolate a restriction fragment that comprises the dhfr gene, plasmid pTPA303 was double-digested with HindIII and EcoRI restriction enzymes, and the ~2340 bp EcoRI-HindIII restriction fragment that comprises the dhfr gene was isolated and recovered.

To isolate the ~2 kb HindIII-SstI restriction fragment of plasmid pTPA303 that comprises the coding region for the carboxy-terminus of TPA and the SV40 promoter, plasmid pTPA303 was double digested with HindIII and SstI restriction enzymes in 1X HindIII buffer. The ~1.7 kb fragment was isolated from the gel and prepared for ligation.

To isolate the ~680 bp XhoII (compatible for ligation with the BglII overlap)-SstI restriction fragment of plasmid pBW28 that comprises the coding region for the amino terminus of modified TPA, about 10 μg of plasmid pBW28 were digested with XhoII enzyme to completion in 1X XhoII buffer (0.1M Tris-HCl, pH=8.0; 0.1 M MgCl$_2$; 0.1% Triton X-100; and 1 mg/ml BSA). The XhoII-digested DNA was recovered by ethanol precipitation and subsequently digested to completion with SstI enzyme. The XhoII-SstI-digested DNA was loaded onto an acrylamide gel, and the desired fragment was isolated from the gel and prepared for ligation.

About 0.1 μg of each of the above fragments: the ~2.7 kb EcoRI-BglII restriction fragment of plasmid pTPA301; the ~2.34 kb EcoRI-HindIII restriction fragment of plasmid pTPA303; the ~1.7 kb SstI-HindIII restriction fragment of plasmid pTPA303; and the ~0.68 kb SstI-XhoII restriction fragment of plasmid pBW28 were ligated together to form plasmid pBW32. The ligation mix was used to transform *E. coli* K12 MM294 as taught in Example 3, except that 50 mM CaCl$_2$ was used in the procedure. Transformants were identified by their ampicillin-resistant phenotype and by restriction analysis of their plasmid DNA. Plasmid pBW32 DNA was obtained from the *E. coli* K12 MM294/pBW32 transformants in substantial accordance with the procedure of Example 1.

EXAMPLE 20

Construction of Plasmids pLPChd1 and pLPChd2

About 20 μg of plasmid pBW32 in 20 μl of TE buffer were added to 10 μl of 10X BamHI buffer and 60 of H$_2$O. About 10 μl (~50 units) of restriction enzyme BamHI were added to the solution of plasmid pBW32 DNA, and the resulting reaction was incubated at 37° C. for two hours. The BamHI-digested plasmid pBW32 DNA was precipitated with ethanol, collected by centrifugation, and resuspended in 5 μl of 10X Klenow buffer, 45 μl of H$_2$O, and 2 μl (~100 units) of Klenow enzyme. The reaction was incubated at 16° C. for 30 minutes; then, the reaction mixture was loaded onto an agarose gel and electrophoresed until the digestion products were clearly separated. The ~1.9 kb Klenow-treated, BamHI restriction fragment of plasmid pBW32 that comprises the dhfr gene was isolated from the gel and prepared for ligation in substantial accordance with the procedure of Example 15A. About 4 μg of the desired fragment were obtained and suspended in 5 μl of TE buffer.

About 200 μg of plasmid pLPChyg1 in 100 μl of TE buffer were added to 15 μl of 10X EcoRI buffer and 30 μl of H$_2$O. About 5 μl (~50 units) of restriction enzyme EcoRI were added to the solution of plasmid pLPChyg1 DNA, and the resulting reaction was incubated at 37° C. for about 10 minutes. The short reaction time was calculated to produce a partial EcoRI digestion. Plasmid pLPChyg1 has two EcoRI restriction sites, one of which is within the coding sequence of the hygromycin resistance-conferring (HmR) gene, and it was desired to insert the dhfr-gene-containing restriction fragment into the EcoRI site of plasmid pLPChyg1 that is not in the HmR gene. The partially-EcoRI-digested plasmid pLPChyg1 DNA was loaded onto an agarose gel and electrophoresed until the singly-cut plasmid pLPChyg1 DNA was separated from uncut plasmid DNA and the other digestion products. The singly-cut DNA was isolated from the gel and prepared for ligation in substantial accordance with the procedure of Example 15A. About 2 μg of the singly-EcoRI-cut plasmid pLPChyg1 were obtained and suspended in 25 μl of TE buffer. To this sample, about 5 μl (~25 units) of Klenow enzyme, 5 μl of 10X Klenow buffer, and 40 μl of H$_2$O were added, and the resulting reaction was incubated at 16° C. for 60 minutes. The Klenow-treated, partially-EcoRI-digested DNA was then extracted twice with phenol and then once with chloroform, precipitated with ethanol, and resuspended in 25 μl of TE buffer.

About 5 μl of the ~1.9 kb Klenow-treated BamHI restriction fragment of plasmid pBW32 and about 5 μl of the singly-EcoRI-cut plasmid pLPChyg1 DNA were mixed together, and 1 μl of 10X ligase buffer, 5 μl of H$_2$O, 1 μl (~500 units) of T4 DNA ligase, and 1 μl (~2 units) of T4 RNA ligase were added to the mixture of DNA, and the resulting reaction was incubated at 16° C. overnight. The ligated DNA constituted the desired plasmids pLPChd1 and pLPChd2, which differ only with respect to the orientation of the ~1.9 kb fragment that comprises the dhfr gene.

The ligated DNA was used to transform *E. coli* K12 HB101 cells made competent for transformation in substantial accordance with the procedure of Example 3. The transformed cells were plated onto L agar containing 100 μg/ml ampicillin, and the ampicillin-resistant transformants were analyzed by restriction enzyme analysis of their plasmid DNA to identify the *E. coli* K12 HB101/pLPChd1 and *E. coli* K12 HB101/pLPChd2 transformants. For the purposes of this disclosure, plasmid pLPChd1 has been designated plasmid pLChd. A restriction site and function map of plasmid pLPChd is presented in FIG. 20 of the accompanying drawings. Plasmid pLPChd1 and plasmid pLPChd2 DNA were isolated from the appropriate transformants in substantial accordance with the procedure of Example 1.

EXAMPLE 21

Construction of Expression Vector pALPKSA

Ten μg of plasmid pGAG1317 are digested in substantial accordance with the teaching of Example 2, except restriction enzyme BssHII and 10X BssHII buffer (250 mM NaCl, 60 mM Tris-HCl (pH 7.4) and 60 mM MgCl$_2$) is used. The 5' overlap of this restriction site is then filled-in using Klenow in substantial accordance with the teaching of Example 5. The reaction is stopped and the DNA precipitated. The DNA is next digested in substantial accordance with the teaching of Example 2, except restriction enzyme HincII and 10X HincII buffer (100 mM Tris-HCl (pH 7.4), 1M NaCl and 70 mM MgCl$_2$) are used. After 2 hours at 37° C., the DNA is precipitated, and electrophoresed through an agarose gel, then the ~1200 bp HincII-BssHII cut, filled-in fragment is isolated and purified in substantial accordance with the teaching of Example 11B.

About 10 μg of plasmid pLHChd are digested in substantial accordance with the teachings of Example 2 except restriction enzyme BclI and 10X BClI buffer (60 mM Tris-HCl (pH 7.4), 750 mM KCl and 100 mM MgCl$_2$) are used. After 2 hours at 37° C., the 5' overlap of the restriction are are filled-in using Klenow in substantial accordance with the teaching of Example 5. Next, the DNA is treated with calf intestine alkaline phosphatase in substantial accordance with the teaching of Example 12. The DNA is next electrophoresed through an agarose gel and the large BclI-BclI vector fragment is isolated and purified in substantial accordance with the teaching of Example 11B.

The HincII-BssHII cut, filled-in, ~1200 bp fragment of pGAG1317 is then ligated into the BclI cut vector of pLPChd in substantial accordance with the teaching of Example 2. The resultant plasmid is then transformed into *E. coli* K12 RV308 in substantial accordance with the teaching of Example 3. The ligation yields two plasmids which differ only in the orientation of the antigen. Restriction mapping discloses the desired plasmid pALPKSA, which contains the antigen fragment driven by the Late Promoter of pLPChd. A restriction site and function map of plasmid pALPKSA is presented in FIG. 21 of the accompanying drawings.

EXAMPLE 22

Construction of Eukaryotic Host Cell Transformants of Expression Vector pALPKSA

The expression vector pALPKSA contains the BK enhancer described in U.S. patent application No. 07/129,028, Attorney Docket X-6606A, filed Dec. 4, 1987, the teaching of which is incorporated herein by reference. The BK enhancer stimulates gene expression in the presence of the E1A gene product. Because 293 cells constitutively express the E1A gene product, 293 cells are the preferred host for the eukaryotic expression vectors of the present invention. 293 cells are human embryonic kidney cells transformed with adenovirus type 5 (note that any particular type of adenovirus can be used to supply the E1A gene product in the method of the present invention) and are available from the ATCC under the accession number CRL 1573. However, the expression vectors of the present invention function in a wide variety of host cells, even if the E1A gene product is not present. Furthermore, the E1A gene product can be introduced into a non-E1A-producing cell line either by transformation with a vector that comprises the E1A gene, or with sheared adenovirus DNA, or by infection with adenovirus.

The transformation procedure described below refers to 293 cells as the host cell line; however, the procedure is generally applicable to most eukaryotic cell lines. 293 cells are obtained from the ATCC under the accession number CRL 1573 in a 25 mm$^2$ flask containing a confluent monolayer of about $5.5 \times 10^6$ cells in Eagle's Minimum Essential Medium with 10% heat-inactivated horse serum. The flask is incubated at 37° C.; medium is changed twice weekly. The cells are subcultured by removing the medium, rinsing with Hank's Balanced Salts solution (Gibco), adding 0.25% trypsin for 1–2 minutes, rinsing with fresh medium, aspirating, and dispensing into new flasks at a subcultivation ratio of 1:5 or 1:10.

One day prior to transformation, cells are seeded at $0.7 \times 10^6$ cells per dish. The medium is changed 4 hours prior to transformation. Sterile, ethanol-precipitated plasmid DNA dissolved in TE buffer is used to prepare a 2X DNA-CaCl$_2$ solution containing 40 μg/ml DNA and 250 mM CaCl$_2$. 2X HBS is prepared containing 280 mM NaCl, 50 mM Hepes, and 1.5 mM sodium phosphate, with the pH adjusted to 7.05–7.15. The 2X DNA-CaCl$_2$ solution is added dropwise to an equal volume of sterile 2X HBS. A one ml sterile plastic pipette with a cotton plug is inserted into the mixing tube that contains the 2X HBS, and bubbles are introduced by blowing while the DNA is being added. The calcium-phosphate-DNA precipitate is allowed to form without agitation for 30–45 minutes at room temperature.

The precipitate is then mixed by gentle pipetting with a plastic pipette, and one ml (per plate) of precipitate is added directly to the 10 ml of growth medium that covers the recipient cells. After 4 hours of incubation at 37° C., the medium is replaced with DMEM with 10% fetal bovine serum and the cells allowed to incubate for an additional 72 hours before providing selective pressure. For plasmids that do not comprise a selectable marker that functions in eukaryotic cells, the transformation procedure utilizes a mixture of plasmids: an expression vector that lacks a selectable marker; and an expression vector that comprises a selectable marker that functions in eukaryotic cells. This co-transformation technique allows for the identification of cells that comprise both of the transforming plasmids.

For cells transfected with plasmids containing the hygromycin resistance-conferring gene, hygromycin is added to the growth medium to a final concentration of about 200 to 400 μg/ml. The cells are then incubated at 37° C. for 2–4 weeks with medium changes at 3 to 4 day intervals. The resulting hygromycin-resistant colonies are transferred to individual culture flasks for characterization. The selection of neomycin (G418 is also used in place of neomycin)-resistant colonies is performed in substantial accordance with the selection procedure for hygromycin-resistant cells, except that neomycin is added to a final concentration of 400 μg/ml rather than hygromycin. 293 cells are dhfr positive, so 293 transformants that contain plasmids comprising the dhfr gene are not selected solely on the basis of the dhfr-positive phenotype, which is the ability to grow in media that lacks hypoxanthine and thymine. Cell lines that do lack a functional dhfr gene and are transformed with dhfr-containing plasmids can be selected for on the basis of the dhfr+ phenotype.

The use of the dihydrofolate reductase (dhfr) gene as a selectable marker for introducing a gene or plasmid into a dhfr-deficient cell line and the subsequent use of methotrexate to amplify the copy number of the plasmid has been well established in the literature. Although the use of dhfr as a selectable and amplifiable marker in dhfr-producing cells has not been well studied, evidence in the literature would suggest that dhfr can be used as a selectable marker in dhfr-producing cells and for gene amplification. The use of the present invention is not limited by the selectable marker used. Moreover, amplifiable markers such as metallothionein genes, adenosine deaminase genes, or members of the multigene resistance family, exemplified by P-glycoprotein, can be utilized.

We claim:

1. A recombinant DNA encoding mature KSA wherein the coding strand is:

5'-GCA AAA CCT GAA GGG GCC

CTC CAG AAC AAT GAT GGG CTT TAT GAT

CCT GAC TGC GAT GAG AGC GGG

CTC TTT AAG GCC AAG CAG TGC AAC

GGC ACC TCC ACG TGC TGG TGT

GTG AAC ACT GCT GGG GTC AGA AGA

ACA GAC AAG GAC ACT GAA ATA

ACC TGC TCT GAG CGA GTG AGA ACC

TAC TGG ATC ATC ATT GAA CTA

AAA CAC AAA GCA AGA GAA AAA CCT

TAT GAT AGT AAA AGT TTG CGG

ACT GCA CTT CAG AAG GAG ATC ACA

ACG CGT TAT CAA CTG GAT CCA

AAA TTT ATC ACG AGT ATT TTG TAT

GAG AAT AAT GTT ATC ACT ATT

GAT CTG GTT CAA AAT TCT TCT CAA

AAA ACT CAG AAT GAT GTG GAC

ATA GCT GAT GTG GCT TAT TAT TTT

GAA AAA GAT GTT AAA GGT GAA

TCC TTG TTT CAT TCT AAG AAA ATG

GAC CTG ACA GTA AAT GGG GAA

CAA CTG GAT CTG GAT CCT GGT CAA

ACT TTA ATT TAT TAT GTT GAT

GAA AAA GCA CCT GAA TTC TCA ATG

CAG GGT CTA AAA GCT GGT GTT

ATT GCT GTT ATT GTG GTT GTG GTG

ATG GCA GTT GTT GCT GGA ATT

GTT GTG CTG GTT ATT TCC AGA AAG

AAG AGA ATG GCA AAG TAT GAG

AAG GCT GAG ATA AAG GAG ATG GGT

GAG ATG CAT AGG GAA CTC AAT GCA-3' wherein A is deoxyadenyl, G is deoxyguanyl, C is deoxycytidyl, and T is thymidyl.

2. A recombinant DNA encoding pro KSA wherein the coding strand is:

5'-GCA GCT CAG GAA GAA TGT GTC TGT GAA AAC TAC AAG CTG GCC GTA

```
AAC TGC TTT GTG AAT AAT AAT CGT CAA TGC CAG TGT ACT TCA GTT
TTG GTG ATG AAG GCA GAA ATG AAT GGC TCA AAA CTT GGG AGA AGA
GCA AAA CCT GAA GGG GCC CTC CAG AAC AAT GAT GGG CTT TAT GAT
CCT GAC TGC GAT GAG AGC GGG CTC TTT AAG GCC AAG CAG TGC AAC
GGC ACC TCC ACG TGC TGG TGT GTG AAC ACT GCT GGG GCT AGA AGA
ACA GCA AAG GAC ACT GAA ATA ACC TGC TCT GAG CGA GTG AGA ACC
TAC TGG ATC ATC ATT GAA CTA AAA CAC AAA GCA AGA GAA AAA CCT
TAT GAT AGT AAA AGT TTG CGG ACT GCA CTT CAG AAG GAG ATC ACA
ACG CGT TAT CAA CTG GAT CCA AAA TTT ATC ACG AGT ATT TTG TAT
GAG AAT AAT GTT ATC ACT ATT GAT CTG GTT CAA AAT TCT TCT CAA
AAA ACT CAG AAT GAT GTG GAC ATA GCT GAT GTG GCT TAT TAT TTT
GAA AAA GAT GTT AAA GGT GAA TCC TTG TTT CAT TCT AAG AAA ATG
GAC CTG ACA GTA AAT GGG GAA CAA CTG GAT CTG GAT CCT GGT CAA
ACT TTA ATT TAT TAT GTT GAT GAA AAA GCA CCT GAA TTC TCA ATG
CAG GGT CTA AAA GCT GGT GTT ATT GCT GTT ATT GTG GTT GTG GTG
ATG GCA GTT GTT GCT GGA ATT GTT GTG CTG GTT ATT TCC AGA AAG
AAG AGA ATG GCA AAG TAT GAG AAG GCT GAG ATA AAG GAG ATG GGT
GAG ATG CAT AGG GAA CCT AAT GCA-3'
``` wherein A is deoxyadenyl, G is deoxyguanyl, C is deoxycytidyl, and T is thymidyl.

3. A recombinant DNA encoding prepro KSA herein the coding strand is:

```
5'-ATG GCG CCC CCG CAG GTC CTC GCG TTC GGG CTT CTG CTT GCC GCG
GCG ACG GCG ACT TTT GCC GCA GCT CAG GAA GAA TGT GTC TGT GAA
AAC TAC AAG CTG GCC GTA AAC TGC TTT GTG AAT AAT AAT CGT CAA
TGC CAG TGT ACT TCA GTT GGT GCA CAA AAT ACT GTC ATT TGC TCA
AAG CTG GCT GCC AAA TGT TTG GTG ATG AAG GCA GAA ATG AAT GGC
TCA AAA CTT GGG AGA AGA GCA AAA CCT GAA GGG GCC CTC CAG AAC
AAT GAT GGG CTT TAT GAT CCT GAC TGC GAT GAG AGC GGG CTC TTT
AAG GCC AAG CAG TGC AAC GGC ACC TCC ACG TGC TGG TGT GTG AAC
ACT GCT GGG GTC AGA AGA ACA GAT AAG GAC ACT GAA ATA ACC TGC
TCT GAG CGA GTG AGA ACC TAC TGG ATC ATC ATT GAA CTA AAA CAC
AAA GCA AGA GAA AAA CCT TAT GAT AGT AAA AGT TTG CGG ACT GCA
CTT CAG AAG GAG ATC ACA ACG CGT TAT CAA CTG GAT CCA AAA TTT
ATC ACG AGT ATT TTG TAT GAG AAT AAT GTT ATC ACT ATT GAT CTG
GTT CAA AAT TCT TCT CAA AAA ACT CAG AAT GAT GTG GAC ATA GCT
GAT GTG GCT TAT TAT TTT GAA AAA CAT GTT AAA GGT GAA TCC TTG
TTT CAT TCT AAG AAA ATG GAC CTG ACA GTA AAT GGG GAA CAA CTG
GAT CTG GAT CCT GGT CCA ACT TTA ATT TAT TAT GTT GAT GAA AAA
GCA CCT GAA TTC TCA ATG CAG GGT CTA AAA GCT GGT GTT ATT GCT
GTT ATT GTG GTT GTG GTG ATG GCA GTT GTT GCT GGA ATT GTT GTG
CTG GTT ATT TCC AGA AAG AAG AGA ATG GCA AAG TAT GAG AAG GCT
GAG ATA AAG GAG ATG GGT GAG ATG CAT AAG GAA CTC AAT GCA-3'
``` wherein A is deoxyadenyl, G is deoxyguanyl, C is deoxycytidyl, and T is thymidyl.

4. A recombinant DNA vector that comprises the DNA of claim 1.

5. A recombinant DNA vector that comprises the DNA of claim 2.

6. A recombinant DNA vector that comprises the DNA of claim 3.

7. The recombinant DNA vector of claim 6 that is plasmid pGAG1317.

8. A recombinant DNA expression vector of claim 4 that further comprises a promoter and translational activating sequence positioned to drive expression of said DNA.

9. A recombinant DNA expression vector of claim 5 that further comprises a promoter and translational activating sequence positioned to drive expression of said DNA.

10. A recombinant DNA expression vector of claim 6 that further comprises a promoter and translational activating sequence positioned to drive expression of said DNA.

11. The recombinant DNA expression vector of claim 8, wherein said promoter functions in a eukaryotic cell.

12. The recombinant DNA expression vector of claim 9, wherein said promoter functions in a eukaryotic cell.

13. The recombinant DNA expression vector of claim 10, wherein said promoter functions in a eukaryotic cell.

14. The recombinant DNA expression vector of claim 11, wherein said promoter is the Adenovirus Late Promoter.

15. The recombinant DNA expression vector of claim 12, wherein said promoter is the Adenovirus Late Promoter.

16. The recombinant DNA expression vector of claim 13, wherein said promoter is the Adenovirus Late Promoter.

17. The recombinant DNA expression vector of claim 8, wherein said promoter functions in a prokaryotic cell.

18. The recombinant DNA expression vector of claim 9, wherein said promoter functions in a prokaryotic cell.

19. The recombinant DNA expression vector of claim 10, wherein said promoter functions in a prokaryotic cell.

20. The recombinant DNA expression vector of claim 17, wherein said promoter is the λpL promoter.

21. The recombinant DNA expression vector of claim 18, wherein said promoter is the λpL promoter.

22. The recombinant DNA expression vector of claim 19, wherein said promoter is the λpL promoter.

23. A recombinant DNA expression vector that is plasmid pLKSA.

24. A recombinant DNA vector selected from the group consisting of plasmids pAG932, pAG1338 and pLKSA-B.

25. The recombinant DNA vector of claim 24 that is pAG932.

26. The recombinant DNA vector of claim 24 that is pAG1338.

27. The recombinant DNA vector of claim 24 that is pLKSA-B.

* * * * *

UNITED STATES PATENT AND TRADEMARK OFFICE
CERTIFICATE OF CORRECTION

PATENT NO.    :   5,348,887

DATED         :   September 20, 1994

INVENTOR(S)   :   Thomas F. Bumol, Robert A. Gadski,
                  Amy E. Hamilton, J. Richard Sportsman,
                  Joann Strnad It is certified that an error appears in the above-identified patent and that said Letters Patent is hereby corrected as shown below:

Column 65, Claim 3, line 1, reads "A recombinant DNA encoding prepro KSA herein.." should read -- A recombinant DNA encoding prepro KSA wherein... --

Column 65, Claim 3, line 9 of the sequence reads "ACT GCT GGG GTC AGA AGA ACA GAT AAG GAC ACT GAA ATA ACC TGC" should read -- ACT GCT GGG GTC AGA AGA ACA GAC AAG GAC ACT GAA ATA ACC TGC --

Column 65, Claim 3, line 15 of the sequence reads "GAT GTG GCT TAT TAT TTT GAA AAA CAT GTT AAA GGT GAA TCC TTG" should read -- GAT GTG GCT TAT TAT TTT GAA AAA GAT GTT AAA GGT GAA TCC TTG --

Column 65, Claim 3, line 21 of sequence reads "GAG ATA AAG GAG ATG GGT GAG ATG CAT AAG GAA CTC AAT GCA-3'" should read -- GAG ATA AAG GAG ATG GGT GAG ATG CAT AGG GAA CTC AAT CGA-3' --

Signed and Sealed this

Eighteenth Day of April, 1995

Attest:

BRUCE LEHMAN

*Attesting Officer*

*Commissioner of Patents and Trademarks*